(12) United States Patent
Chen et al.

(10) Patent No.: US 10,881,515 B2
(45) Date of Patent: Jan. 5, 2021

(54) IMPLANTATION OF CARTILAGE

(75) Inventors: Silvia S. Chen, Virginia Beach, VA (US); Xiaofei Qin, Virginia Beach, VA (US); Jingsong Chen, Virginia Beach, VA (US); Lloyd Wolfinbarger, Jr., Norfolk, VA (US)

(73) Assignee: LifeNet Health, Virginia Beach, VA (US)

( * ) Notice: Subject to any disclaimer, the term of this patent is extended or adjusted under 35 U.S.C. 154(b) by 1024 days.

(21) Appl. No.: 13/537,194

(22) Filed: Jun. 29, 2012

(65) Prior Publication Data

US 2013/0030528 A1 Jan. 31, 2013

Related U.S. Application Data

(63) Continuation of application No. 11/826,530, filed on Jul. 16, 2007, now abandoned, which is a
(Continued)

(51) Int. Cl.
*A61F 2/38* (2006.01)
*A61F 2/30* (2006.01)
(Continued)

(52) U.S. Cl.
CPC ...... *A61F 2/30756* (2013.01); *A61B 17/1604* (2013.01); *A61B 17/1635* (2013.01); *A61F 2/28* (2013.01); *A61F 2/30749* (2013.01); *A61F 2/4644* (2013.01); *A61L 27/3612* (2013.01); *A61L 27/3654* (2013.01); *A61L 27/3683* (2013.01); *A61L 27/3804* (2013.01); *A61B 17/1675* (2013.01); *A61F 2/3094* (2013.01); *A61F 2/38* (2013.01); *A61F 2/3859* (2013.01); *A61F 2002/2817* (2013.01); *A61F 2002/2839* (2013.01); *A61F 2002/30004* (2013.01); *A61F 2002/30224* (2013.01); *A61F 2002/30235* (2013.01); *A61F 2002/30751* (2013.01); *A61F 2002/30759* (2013.01);
(Continued)

(58) Field of Classification Search
CPC ................... A61F 2002/30042; A61F 2/30756
See application file for complete search history.

(56) References Cited

U.S. PATENT DOCUMENTS 4,372,888 A 2/1983 Hjelmeland
4,394,370 A * 7/1983 Jefferies ................ A61L 27/227
106/122

(Continued)

FOREIGN PATENT DOCUMENTS

WO 2006090372 8/2006

OTHER PUBLICATIONS

Canadian Office Action dated Aug. 24, 2015 in Canadian Application No. 2,693,840.
(Continued)

*Primary Examiner* — Christopher D. Prone
(74) *Attorney, Agent, or Firm* — RatnerPrestia

(57) ABSTRACT

The invention is directed towards a process for implanting a cartilage graft into a cartilage defect and sealing the implanted cartilage graft with recipient tissue. The invention is also directed towards a process for repairing a cartilage defect and implanting a cartilage graft into a human or animal. The invention is further directed toward a repaired cartilage defect.

24 Claims, 48 Drawing Sheets

Related U.S. Application Data continuation of application No. 11/826,518, filed on Jul. 16, 2007, now Pat. No. 9,744,043, which is a continuation of application No. 11/826,522, filed on Jul. 16, 2007, which is a continuation of application No. 11/826,523, filed on Jul. 16, 2007, now Pat. No. 9,125,743.

(51) Int. Cl.

| | | |
|---|---|---|
| *A61B 17/16* | (2006.01) | |
| *A61F 2/28* | (2006.01) | |
| *A61F 2/46* | (2006.01) | |
| *A61L 27/36* | (2006.01) | |
| *A61L 27/38* | (2006.01) | |

(52) U.S. Cl.
CPC .......... A61F 2002/30762 (2013.01); A61F 2002/30764 (2013.01); A61F 2002/4646 (2013.01); A61F 2002/4648 (2013.01); A61F 2002/4649 (2013.01); A61F 2230/0069 (2013.01); A61F 2250/0014 (2013.01); A61L 2430/06 (2013.01)

(56) References Cited

U.S. PATENT DOCUMENTS

| | | |
|---|---|---|
| 4,553,974 A | 11/1985 | Dewanjee |
| 4,776,853 A | 10/1988 | Klement et al. |
| 4,801,299 A | 1/1989 | Brendel et al. |
| 4,950,296 A | 8/1990 | McIntyre |
| 5,290,558 A | 3/1994 | O'Leary et al. |
| 5,336,616 A | 8/1994 | Livesey |
| 5,556,379 A | 9/1996 | Wolfinbarger, Jr. |
| 5,624,463 A | 4/1997 | Stone et al. |
| 5,702,446 A * | 12/1997 | Schenck .......... A61F 2/30907 433/226 |
| 5,716,405 A | 2/1998 | Mittelman |
| 5,762,600 A | 6/1998 | Bruchman et al. |
| 5,797,871 A | 8/1998 | Wolfinbarger, Jr. |
| 5,820,581 A | 10/1998 | Wolfinbarger, Jr. |
| 5,855,610 A | 1/1999 | Vacanti et al. |
| 5,879,876 A | 3/1999 | Wolfinbarger, Jr. |
| 5,919,702 A | 7/1999 | Purchio et al. |
| 5,976,104 A | 11/1999 | Wolfinbarger, Jr. |
| 5,977,034 A | 11/1999 | Wolfinbarger, Jr. |
| 5,977,432 A | 11/1999 | Wolfinbarger, Jr. |
| 6,024,735 A | 2/2000 | Wolfinbarger, Jr. |
| 6,030,635 A | 2/2000 | Gertzman et al. |
| 6,039,762 A | 3/2000 | McKay |
| 6,046,379 A | 4/2000 | Stone et al. |
| 6,060,306 A | 5/2000 | Flatt et al. |
| 6,110,209 A | 8/2000 | Stone |
| 6,121,042 A | 9/2000 | Peterson et al. |
| 6,179,872 B1 | 1/2001 | Bell |
| 6,214,054 B1 | 4/2001 | Cunanan et al. |
| 6,293,970 B1 | 9/2001 | Wolfinbarger, Jr. et al. |
| 6,294,187 B1 | 9/2001 | Boyce et al. |
| 6,326,188 B1 | 12/2001 | Wolfinbarger, Jr. |
| 6,340,477 B1 | 1/2002 | Anderson |
| 6,348,069 B1 | 2/2002 | Vacanti et al. |
| 6,371,992 B1 | 4/2002 | Tanagho et al. |
| 6,379,367 B1 | 4/2002 | Vibe-Hansen et al. |
| 6,379,385 B1 | 4/2002 | Kalas et al. |
| 6,398,811 B1 | 6/2002 | McKay |
| 6,416,995 B1 | 7/2002 | Wolfinbarger, Jr. et al. |
| 6,432,712 B1 | 8/2002 | Wolfinbarger, Jr. |
| 6,436,138 B1 | 8/2002 | Dowd et al. |
| 6,437,018 B1 | 8/2002 | Gertzman et al. |
| 6,451,543 B1 | 9/2002 | Kochendoerfer |
| 6,454,804 B1 | 9/2002 | Ferree |
| 6,454,811 B1 | 9/2002 | Sherwood et al. |
| 6,482,584 B1 | 11/2002 | Mills et al. |
| 6,488,033 B1 | 12/2002 | Cerundolo |
| 6,506,386 B1 | 1/2003 | Friede |
| 6,544,289 B2 | 4/2003 | Wolfinbarger, Jr. et al. |
| 6,569,200 B2 | 5/2003 | Wolfinbarger, Jr. et al. |
| 6,648,919 B2 | 11/2003 | Ferree |
| 6,734,018 B2 | 5/2004 | Wolfinbarger, Jr. et al. |
| 6,743,574 B1 | 6/2004 | Wolfinbarger, Jr. et al. |
| 6,780,510 B2 | 8/2004 | Ogle et al. |
| 6,855,169 B2 | 2/2005 | Boyer, II et al. |
| 6,858,042 B2 | 2/2005 | Nadler et al. |
| 6,911,212 B2 | 6/2005 | Gertzman et al. |
| 6,936,271 B1 | 8/2005 | Oliver et al. |
| 6,958,149 B2 | 10/2005 | Yukicevic et al. |
| 6,998,135 B1 | 2/2006 | Sunwoo et al. |
| 7,063,726 B2 | 6/2006 | Crouch et al. |
| 7,067,123 B2 | 6/2006 | Gomes et al. |
| 7,108,721 B2 | 9/2006 | Huckle et al. |
| 7,122,057 B2 | 10/2006 | Beam et al. |
| 7,157,428 B2 | 1/2007 | Kusanagi et al. |
| 2002/0006394 A1* | 1/2002 | Redmond ............ A61F 9/0079 424/93.7 |
| 2002/0012982 A1 | 1/2002 | Blakesley |
| 2002/0106625 A1 | 8/2002 | Hung et al. |
| 2002/0115208 A1 | 8/2002 | Mitchell et al. |
| 2003/0068416 A1 | 4/2003 | Burgess |
| 2003/0087428 A1 | 5/2003 | Wolfinbarger |
| 2003/0130746 A1 | 7/2003 | Ashworth et al. |
| 2003/0219417 A1 | 11/2003 | Wolfinbarger, Jr. et al. |
| 2004/0059364 A1 | 3/2004 | Gaskins et al. |
| 2004/0067582 A1* | 4/2004 | Wolfinbarger, Jr. ..... A01N 1/00 435/366 |
| 2004/0076657 A1 | 4/2004 | Wolfinbarger, Jr. et al. |
| 2004/0219058 A1 | 11/2004 | Shimp et al. |
| 2004/0219182 A1 | 11/2004 | Gomes et al. |
| 2004/0219659 A1 | 11/2004 | Altman et al. |
| 2004/0230303 A1 | 11/2004 | Gomes et al. |
| 2005/0019865 A1 | 1/2005 | Kihm |
| 2005/0064042 A1 | 3/2005 | Vunjak-Novakovic et al. |
| 2005/0112086 A1 | 5/2005 | Swan et al. |
| 2005/0152987 A1 | 7/2005 | Malinin |
| 2005/0196460 A1 | 9/2005 | Malinin |
| 2005/0209705 A1 | 9/2005 | Niederauer et al. |
| 2005/0251268 A1 | 11/2005 | Truncale |
| 2006/0074466 A1 | 4/2006 | Malinin |
| 2006/0173394 A1 | 8/2006 | Stroock et al. |
| 2006/0247790 A1 | 11/2006 | McKay |
| 2007/0038299 A1 | 2/2007 | Stone et al. |
| 2007/0082057 A1 | 4/2007 | Masinaei |
| 2007/0082058 A1 | 4/2007 | Masinaei |
| 2007/0083270 A1 | 4/2007 | Masinaei |
| 2007/0093896 A1 | 4/2007 | Malinin |
| 2007/0098759 A1 | 5/2007 | Malinin |
| 2007/0135917 A1 | 6/2007 | Malinin |
| 2007/0135918 A1 | 6/2007 | Malinin |
| 2007/0135928 A1 | 6/2007 | Malinin |
| 2007/0149982 A1 | 6/2007 | Lyons |
| 2007/0233264 A1 | 10/2007 | Nycz et al. |
| 2007/0233272 A1 | 10/2007 | Boyce et al. |
| 2007/0276506 A1 | 11/2007 | Troxel |
| 2007/0292401 A1 | 12/2007 | Harmon |
| 2008/0255676 A1 | 10/2008 | Semler et al. |
| 2008/0262616 A1* | 10/2008 | McKay ............ A61B 17/1635 623/14.12 |
| 2009/0076606 A1 | 3/2009 | Huerta et al. |

OTHER PUBLICATIONS

Seddon A. et al., "Membrane proteins, lipids, and detergents: not just a soap opera," Biochimica et Biophysica Acta 1666, p. 105-117, 2004.

Non Final Office Action for U.S. Appl. No. 12/404,855, dated Jun. 22, 2016, 16 pages.

Ball et al., "The effects of storage on fresh human osteochondral allografts," Clinical and Orthopedics and Related Research, 418:246-252 (2004).

Denker et al., "Chondrogenic differentiation of murine C3H10T1/2 multipotential mesenchymal cells: I. Stimulation by bone morphogenetic protein-2 in high-density micromass cultures," Differentiation, 64(2): 67-76 (1999).

(56) References Cited

OTHER PUBLICATIONS

Hanada et al., "Stimulatory effects of basic fibroblast growth factor and bone morphogenetic protein-2 on osteogenic differentiation of rat bone marrow-derived mesenchymal stem cells," J. Bone Miner. Res., 12(10): 1606-1614 (1997).
Gao et al., "Osteochondral defect repair by demineralized cortical bone matrix," Clinical Orthopaedics and Related Research, (427 Suppl): S62-66 (2004).
Billings et al., "Cartilage resurfacing of the rabbit knee. The use of an allogeneic demineralized bone matrix-autogeneic perichondrium composite implant," Acta Orthopaedica Scandinavica, 61(3):201-206 (1990).
Rich et al., "Cartilage proteoglycans inhibit fibronectin-mediated adhesion," Nature, 293(5829): 224-226 (1981).
Caplan et al., "Principles of cartilage repair and regeneration," Clinical and Orthopedics and Related Research, 342: 254-269 (1997).
Hunziker et al., "Removal of proteoglycans from the surface of defects in articular cartilage transiently enhances coverage by repair cells," Journal of Bone and Joint Surgery, 80(1): 144-150 (1998).
van de Breevaart Bravenboer et al., "Improved cartilage integration and interfacial strength after enzymatic treatment in a cartilage transplantation model," Arthritis Research and Therapy, 6(5): R469-476 (2004).
Bos et al., "Specific enzymatic treatment of bovine and human articular cartilage: implications for integrative cartilage repair," Arthritis and Rheumatism, 46(4): 976-985 (2002).
Schaefer et al., "Lubricin reduces cartilage-cartilage integration," Biorheology, 41(3-4): 503-508 (2004).
Wayne et al., "A u-p finite element analysis of the behaviors of a repaired cartilage surface," Trans. Orthop. Res. Soc., 37:75 (1991).
Chan et al., "Enhancement of porcine skin graft adherence using a light-activated process," J. Surg. Res., 108(1): 77-84 (2002).
Proano et al., "Photochemical keratodesmos for bonding corneal incisions," Invest. Ophthalmol. Vis. Sci., 45(7): 2177-2181 (2004).
Pollo et al., "Sutureless avascular meniscal repair with a photoactive naphthalimide compound: a preliminary animal study," Arthroscopy, 20(8): 824-830 (2004).
Office Action issued in a corresponding Canadian Patent Application No. 2,693,840, dated Nov. 25, 2014.
Extended Search Report issued in a corresponding European Patent Application No. 08780196.5, dated Mar. 4, 2014.
Final Office Action for U.S. Appl. No. 11/826,518, dated Oct. 19, 2016, 8 pages.
Muco, Mucopolysaccharides, Medline Plus, Web Entry, 2015, 2 pages.
Orsi et al., "Carotid Arteries in the Dog: Structure and Histophysiology", Int. J. Morphol., 2006 vol. 24, No. 2, pp. 239-244.
HBBS, Hanks Balanced Salt Solution Recipe and preparation, ATT Bioquest, downloaded at https://www.aatbio.com/resources/buffer-preparations-and-recipes/hbss-hanks-balanced-salt-solution, 2017, 2 pages.
European Communication for EP Application No. 08780196.5, dated Dec. 23, 2016, 5 pages.
Communication Pursuant to Article 94(3) for European Application No. 08 780 196.5, dated Feb. 7, 2019, 4 pages.
Canadian Office Action for Canadian Application No. 3,003,367, dated Aug. 8, 2019, 4 pages.
European Communication pursuant to Article 94(3) for European Application No. 08 780 196.5, dated Nov. 7, 2019, 6 pages.
European Communication pursuant to Article 94(3) for European Application No. 08 780 196.5, dated Apr. 9, 2020, 4 pages.
Final Office Action for U.S. Appl. No. 11/826,522, dated Oct. 11, 2016, 19 pages.
Final Office Action for U.S. Appl. No. 14/068,308, dated Sep. 22, 2016, 17 pages.
Non Final Office Action for U.S. Appl. No. 14/058,240, dated Sep. 7, 2016, 15 pages.
Canadian Examination Report for Canadian Application No. 3,003,367, dated Oct. 27, 2020, 3 pages.

\* cited by examiner

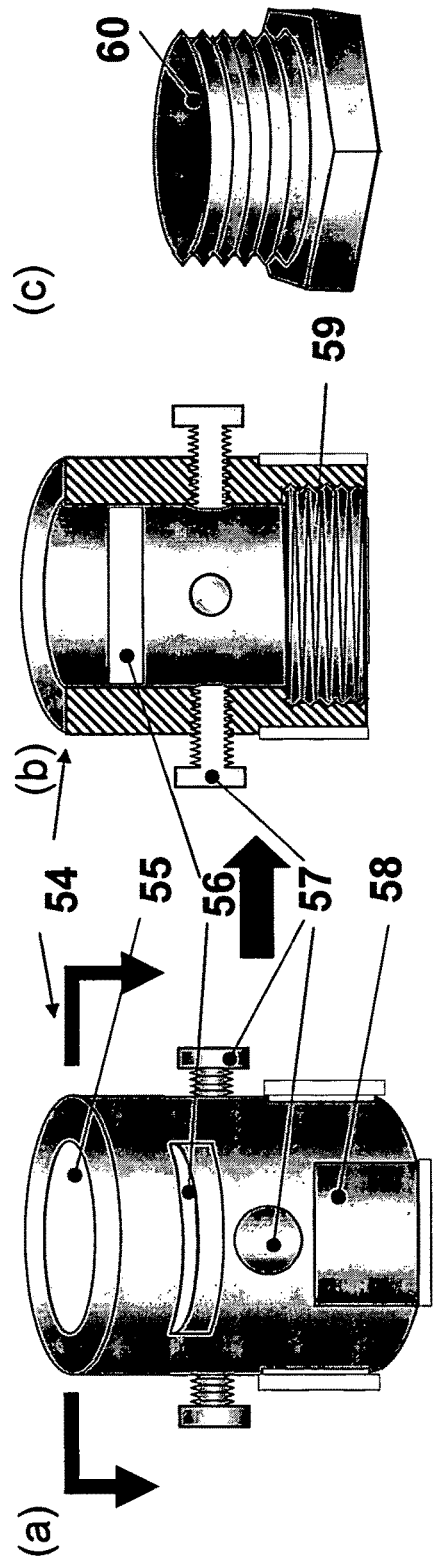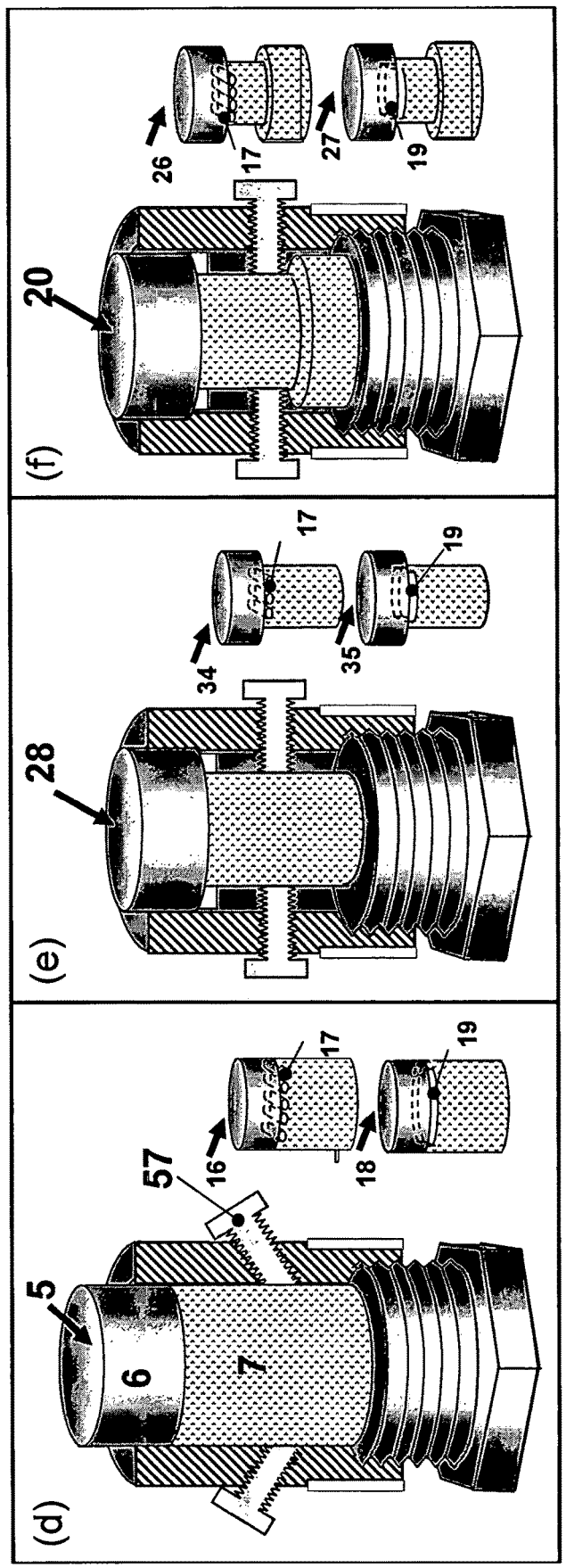
Fig. 9

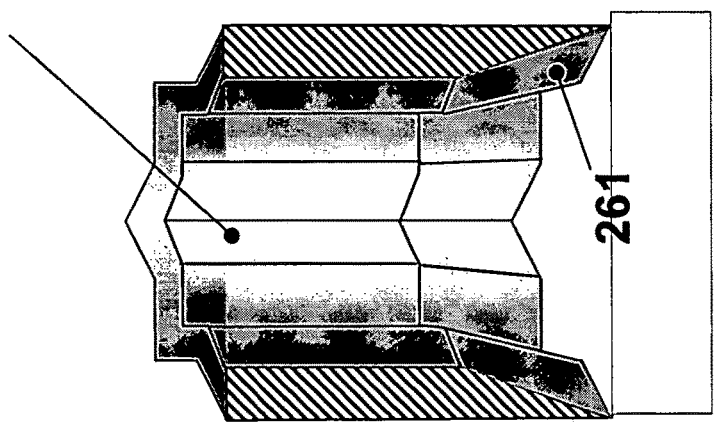
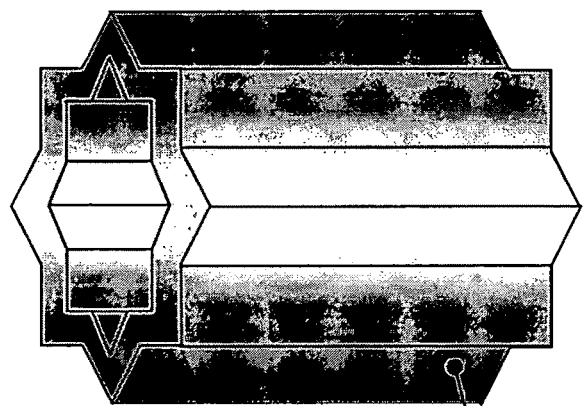
Fig. 32

IMPLANTATION OF CARTILAGE

CROSS-REFERENCE TO R LATER APPLICATIONS

This application is a continuation of and claims priority under 35 U.S.C. § 120 to U.S. application Ser. No. 11/826,518, filed Jul. 16, 2007, now U.S. Pat. No. 9,744,043, U.S. application Ser. No. 11/826,522, filed Jul. 16, 2007, U.S. application Ser. No. 11/826,523, filed Jul. 16, 2007, now U.S. Pat. No. 9,125,743, and U.S. application Ser. No. 11/826,530, filed Jul. 16, 2007, each of which is incorporated herein by reference in its entirety.

FIELD OF THE INVENTION

The invention is directed towards a process for implanting a cartilage graft into a cartilage defect and sealing the implanted cartilage graft with recipient tissue. This application claims priority to 3 cofiled and copending applications, which are incorporated by reference herein in their entireties.

BACKGROUND OF THE INVENTION

Cartilage is a highly hydrated connective tissue with chondrocytes embedded in a dense extracellular matrix made of, for example, collagen, proteoglycan and water. Although the biochemical composition of cartilage differs according to types, there are mainly three types of cartilage present in a mammal, which include: articular or hyaline cartilage, fibrocartilage, and elastic cartilage. Hyaline cartilage is predominantly found on the articulating surfaces of articulating joints and contains type II collagen and proteoglycans. It is found also in epiphyseal plates, costal cartilage, tracheal cartilage, bronchial cartilage, and nasal cartilage. Fibrocartilage is mainly found in menisci, the annulus fibrosis of the intervertebral disc, tendinous and ligamentous insertions, the symphysis pubis, and insertions of joint capsules. The composition of fibrocartilage is similar to hyaline cartilage except that fibrocartilage contains fibrils of type I collagen that add tensile strength to the cartilage. Elastic cartilage is present in the pinna of the ears, the epiglottis, and the larynx and is similar to hyaline cartilage except that it contains fibers of elastin.

One of the most common cartilage injuries is damage to the fibrocartilage in the knee joint. Meniscal tears are common in young individuals due to sports-related injuries, as well as in older population suffering from degenerative joint diseases. Meniscal allograft transplantation is one of the available treatment options for patients with meniscal tear. Despite some positive results, issues with tissue rejection, disease transmission and a lack of long-term data have limited the use of this approach.

Diseased or traumatized intervertebral disc is another common fibrocartilage injury. The damage on the annulus can cause pain and possible disc herniation that can compress nerves or the spinal cord resulting in arm or leg pain and dysfunction. Recent advances in molecular biology, cell biology and material sciences have opened a new emerging field for cartilage repair.

However, the most common cartilage injury is articular cartilage injury often as a result of sports related trauma. Due to its avascular nature, articular cartilage has very limited capacity for repair. Approximately 500,000 arthroplastic or joint repair procedures are performed each year in the United States. These procedures include approximately 125,000 total hip and 150,000 total knee arthroplastic procedures (Chen, et al., Repair of articular cartilage defects: Part 1, Basic Science of Articular Cartilage Healing, Amer. J. Orthopedics 1999:31-33). Articular cartilage is a complex tissue involving biomechanical function and associated physical stimuli inside the articular cartilage. Articular cartilage is an inhomogeneous material (tissue) and surface loading is converted to mechanical and electrochemical signals by the extracellular matrix through hydraulic and osmotic pressures, fluid and solute/ion flows, matrix deformations and electrical fields (Mow, Van C. and C. C-B. Wang, Some bioengineering considerations for tissue engineering of articular cartilage. Clinical and Orthopedics and Related Research. 1999, Number 367s, S204-S223).

Unfortunately, chondral defects may not heal, especially when the defect does not penetrate the subchondral bone. A wide variety of surgical procedures are in current use or have been proposed for use to repair chondral defects attempt to prompt the resident cellular population to become more metabolically active thereby promoting new matrix synthesis, however, for the most part, these surgical procedures do little more than provide temporary relief of pain.

SUMMARY OF THE INVENTION

One aspect of this invention is to produce a devitalized and shaped cartilage graft suitable for recellularizing in vitro, in vivo, or in situ. The devitalized cartilage graft, particularly articular cartilage graft, may be derived from articular cartilage of human or other animal(s). The subchondral bone, i.e., the cancellous bone portion of the graft, if present, may be cleaned and disinfected to remove bone marrow elements, and the cartilage portion of the graft may be made acellular. Furthermore, the subchondral bone portion may be crafted into various sizes and shapes and modified to incorporate gaps, a bore, channels, or slots to render cleaning, disinfection, devitalization, and recellularization. The cartilage part of the graft can be treated to improve recellularization by chemical or physical modification. The cartilage may further be recellularized from devitalized cartilage matrix. Moreover, the cartilage graft may be implanted into a recipient and sealed with recipient tissue.

The present invention relates to process for repairing a cartilage defect and implanting a cartilage graft into a human or animal.

The process of the present invention may be accomplished according to the following steps: selecting an osteochondral plug that matches the size, contour, and location of the defect site, creating a first bore down to the bone portion of the cartilage defect, creating a second shaped bore that may be concentric to and on top of the first bore to match the shape and size of the cartilage cap of the osteochondral plug, treating the first bore and the second shaped bore at the defect site with a first bonding agent, treating the circumferential area of the cartilage cap on the osteochondral plug with a second bonding agent, inserting the osteochondral plug into the defect site using or not using an insertion device so that the superficial surface of the cartilage cap may be at the same height as the surrounding cartilage surface. Moreover, the first and second bonding agents may be activated by applying a stimulation agent to induce sealing, integration, and restoration of the hydrodynamic environments of the recipient tissue.

The process of the present invention may further be accomplished according to the following steps: selecting an osteochondral plug and cartilage slices that matches the size, contour, and location of the defect site, creating a first bore down to the bone portion of the cartilage defect, creating a second shaped bore that may be concentric to and on top of the first bore to match the shape and size of the cartilage cap of the osteochondral plug, tailoring the cartilage slices according to the shape and the sizes of the second shaped bore and the contour of the joint surface at the cartilage defect, treating the first bore and the second shaped bore at the defect site with a first bonding agent, treating the circumferential area of the cartilage cap on the osteochondral plug with a second bonding agent, treating the circumferential area of the cartilage slices with the second bonding agent, inserting the osteochondral plug into the defect site using or not using an insertion device so that the superficial surface of the cartilage cap may be slightly lower than the surrounding cartilage surface, applying a stimulation agent to activate the first and second bonding agents to induce sealing, integration, and restoration of the hydrodynamic environments of the recipient tissue, and stacking the cartilage slices on top of the osteochondral plug in the defect site until it is at the same height as the surrounding cartilage or matches the contour of the surrounding cartilage surface. The first and second bonding agent may be activated by applying a stimulation agent to induce sealing, integration, and restoration of the hydrodynamic environments of the recipient tissue. The cartilage slices may also be bonded between adjacent slices using the first or second bonding agent. Further, the cartilage slices may be bonded with the superficial surface of osteochondral plug the cartilage cap using the first or second bonding agent before or during implantation.

The process of the present invention may further be accomplished according to the following steps: selecting a cartilage disc that matches the size, contour, and location of the defect site, creating a first bore at the cartilage defect site down to a bone portion, creating a second shaped bore that may be concentric to and on top of the first bore to match the size and shape of the cartilage discs, treating the first bore and the second shaped bore at the defect site with a first bonding agent, inserting a bone filler into the bone portion of the first bore to provide support for the cartilage disc, treating the circumferential area of the cartilage disc with a second bonding agent, and inserting the cartilage disc into the defect site using or not using an insertion device so that the superficial surface of the cartilage disc may be at the same height as the surrounding cartilage surface. The first and second bonding agents may be activated by applying a stimulation agent to induce sealing, integration, and restoration of the hydrodynamic environments of the recipient tissue.

The process of the present invention may even further be accomplished according to the following steps: selecting a cartilage disc and cartilage slices that match the size, contour, and location of the defect site, creating a first bore at a cartilage defect site down to a bone portion, creating a second shaped bore that may be concentric to and on top of the first bore to match the size and shape of the cartilage discs, tailoring the cartilage slices according to the shape and the sizes of the second shaped bore and the contour of the joint surface at the cartilage defect site, treating the first bore and the second shaped bore at the defect site with a first bonding agent, treating the circumferential area of the cartilage disc and the cartilage slices with a second bonding agent, inserting a bone filler into the bone portion of the first bore to provide support for the cartilage disc, inserting the cartilage disc into the defect site using or not using an insertion device so that the superficial surface of the cartilage disc may be slightly lower than the surrounding cartilage surface, applying an stimulation agent to activate the first and second bonding agents to induce sealing, integration, and restoration of the hydrodynamic environments of the tissue, and stacking the cartilage slices into the defect site and wherein the stack of cartilage slices may be at the same height or matches the contour of the surrounding cartilage. The first and second bonding agents may be activated by applying a stimulation agent to induce sealing, integration, and restoration of the hydrodynamic environments of the recipient tissue. Moreover, the cartilage slices may be bonded between adjacent slices using the first or second bonding agent, and the cartilage slices may be bonded with the superficial surface of the cartilage disc using the first or second bonding agent before or during implantation.

The process of the present invention may even further be accomplished according to the following steps: selecting cartilage slices that matches the size, contour, and location of the defect, creating a first bore at a cartilage defect site down to a bone portion, creating a second shaped bore that may be concentric to and on top of the first bore to match the size and shape of the cartilage slices, further tailoring the cartilage slices according to the shape and the sizes of the second shaped bore and the contour of the joint surface at the cartilage defect site, treating the first bore and the second shaped bore at the defect site with a first bonding agent, inserting a bone filler into the bone portion of the first blind bore to provide support for the cartilage slices, treating the circumferential area of the cartilage slices with a second bonding agent, and stacking the cartilage slices into the defect and wherein the stack of cartilage slices may be at the same height as the surrounding cartilage. The first and second bonding agent may be activated by applying a stimulation agent to induce the sealing, integration, and restoration of the hydrodynamic environments of the recipient tissue. Moreover, the cartilage slices may be bonded between adjacent slices using the first or second bonding agent before or during implantation.

The process of the present invention may even further be accomplished according to the following steps: selecting cartilage curls or flakes and a cartilage disc that matches the size, contour, and location of the defect site, creating a first bore at a cartilage defect site down to a bone portion, creating a second shaped bore that may be concentric to and on top of the first bore to match the size and shape of the cartilage disc, treating the first bore and the second shaped bore at the defect site with a first bonding agent, inserting a bone filler into the bone portion of the first bore to provide support for the cartilage disc, treating the circumferential area of the cartilage disc with a second bonding agent, inserting the cartilage curls or flakes into the defect site, and inserting the cartilage disc into the defect site with or without an insertion device so that the superficial surface of the cartilage disc may be at the same height as the surrounding cartilage surface. The first and second bonding agents may be activated by applying a stimulation agent to induce sealing, integration, and restoration of the hydrodynamic environments of the recipient tissue. Further, the cartilage curls or flakes can be mixed with or without a carrier before insertion.

The process of the present invention may even further be accomplished according to the following steps: selecting cartilage curls or flakes and cartilage slices that matches the size, contour, and location of the defect site, creating a first bore at a cartilage defect site down to a bone portion, creating a second shaped bore that may be concentric to and on top of the first bore to match the size and shape of the cartilage slices, treating the first bore and the second shaped bore at the defect site with a first bonding agent, inserting a bone filler into the bone portion of the first bore to provide support for the cartilage curls or flakes and cartilage slices, treating the circumferential area of the cartilage slices with a second bonding agent, inserting the cartilage curls or flakes into the defect site, and stacking the cartilage slices on top of the inserted cartilage curls or flakes so that the stack of cartilage slices may be at the same height or matches the contour of the surrounding cartilage. The first and second bonding agents may be activated by applying a stimulation agent to induce sealing, integration, and restoration of the hydrodynamic environments of the recipient tissue. The cartilage curls or flakes can be mixed with a carrier before insertion.

The process of the present invention may even further be accomplished according to the following steps: crafting a cartilage matrix into individual grafts, cleaning and disinfecting the cartilage graft, applying a pretreatment solution to the cartilage graft, removing cellular debris using an extracting solution to produce a devitalized cartilage graft, implanting the cartilage graft into the cartilage defect with or without an insertion device, and sealing the implanted cartilage graft with recipient tissue. The devitalized cartilage graft may be optionally recellularized in vitro, in vivo, or in situ with viable cells to render the tissue vital before or after the implantation. Further, the devitalized cartilage grafts may be optionally stored between the removing cellular debris and recellularizing steps.

The present invention further relates to an implanted cartilage graft whereby the cartilage graft has been prepared and/or implanted according to any of the processes described herein.

Cartilage grafts may be transplanted containing a viable cell population or as a previously preserved tissue that contains a non-viable cell population (or partially viable cell population) and as a matrix structure that is changed only by the preservation and/or incubation process. The present invention relates to removal of the cell population and modification of the matrix structure such that the matrix will not only recellularize post-implantation, but remain cellular, remodeling into a tissue that maintains structural and functional compatibility. Also considered is the means by which the cartilage graft may be made acellular such that the matrix structure may be changed sufficient so as to promote recellularization and be biocompatible so as to restrict subsequent apoptosis of the infiltrating cells. In addition, treatment of the matrix structure to modify the macromolecular composition of the tissues and the molecular suturing of the implanted cartilage graft serves to control the hydraulic environment within the tissue, to restrict loss of fluids around the surgically created implant site, to provide an environment that allows cell infiltration, and to prevent infiltration of small proteoglycans in the synovial fluid at the opposing surfaces of cartilage graft and the recipient tissue.

BRIEF DESCRIPTION OF THE DRAWINGS

FIG. 9 illustrates a view of an osteochondral plug holder for crafting the cylindrical surface of the subchondral bone portion at the cartilage and subchondral bone interface to form multiple parallel through holes or channels or a slot.

FIG. 32 illustrates a star-shaped cutting blade to create a star-shaped bore in the cartilage portion of the recipient defect site.

DESCRIPTION OF THE INVENTION

Figure 1A:
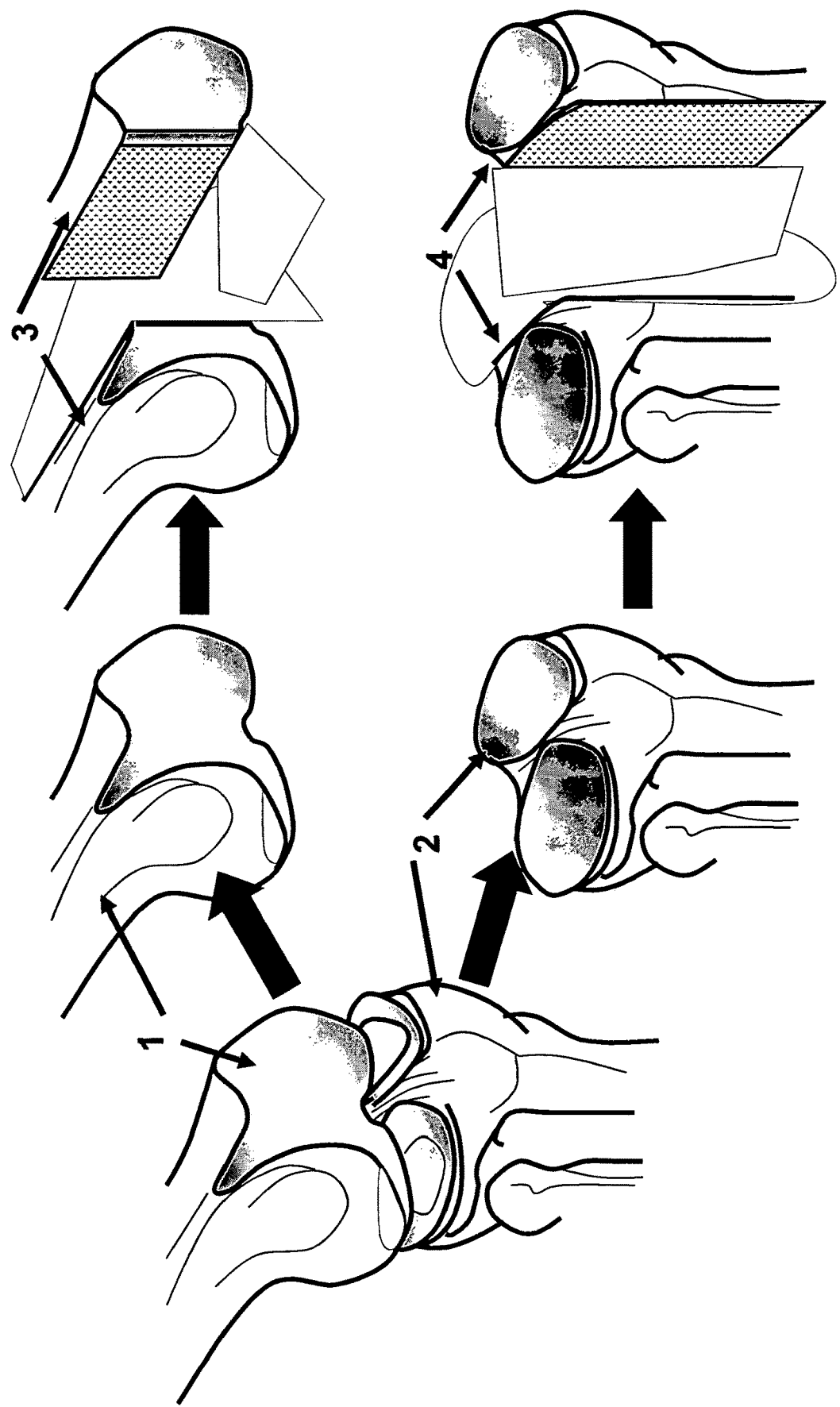
FIG. 1 illustrates a view of a knee joint that is processed to have articular cartilage grafts of (a) whole condyle, whole plateau, hemicondyles, hemiplateaus, or (b) osteochondral plugs.

The terms "autologous" (autograft) and "allogenous" (allograft) are used to describe tissues derived from the individual to receive the tissue and tissues derived from an individual other than the individual from the same species to receive the tissue, respectively.

The phrase "cleaning solution" is used to describe a solution to clean allografts, xenografts, and autografts. The phrase cleaning solution is further meant to describe any cleaning solution which may be used to clean and/or disinfect these tissues.

The phrase "decontaminating agent" is used to describe any substance which can be used to decontaminate bone and/or cartilage. Such substances include, but are not limited to, one or more agents which remove or inactivate/destroy any infectious material. Non-exclusive examples of decontaminating agents include antibacterial agents, antiviral agents, and antimycotic agents. Moreover, the phrase decontaminating agents is also meant to include, but is not limited to substances which may clean bone and/or cartilage by inactivating one or more of bacteria, viruses, and/or fungi such as hydrogen peroxide, detergents, and alcohols. Further examples of decontaminating agents include acids such as hydrochloric acid and bases such as hydrogen peroxide.

The term "devitalized" involves the decellularization, or making tissue acellular, such that minimal cellular remnants remain.

The phrase "recellularizable cells" means cells capable of recellularizing a matrix. Examples of such cells include, but are not limited to autologous or allograft chondrocytes isolated from articular cartilage, fibrocartilage, or elastic cartilage; bone marrow aspirate; or stromal cells from bone marrow, synovium, periostieum, perichondrium, muscle, dermis, umbilical cord blood, adipose tissue, or Warton's jelly; or pericytes.

Integration between the implanted cartilage graft and recipient tissue is important for the success of long-term repair of the cartilage. Adhesion between recipient and grafted cartilage may depend on the cell infiltration and adhesion, the formation of cross-links between the adjacent tissue at the interface, local mechanical environment, and the microenvironment surrounding the tissue. Cell adhesion to cartilage may be inhibited by the presence of proteoglycans. Removal of proteoglycan from cartilage surfaces may expose underlying collagen and other proteins that are known to have cell adhesion properties. Enzymatic treatment of cartilage wounds may increase histological integration and improve biomechanical bonding strength, possibly by increasing the cell density at cartilage wound edges. In addition, lubricin/proteoglycan 4, a lubricating protein physiologically present in the synovial fluid, may reduce the interactive cartilage repair capacity. Therefore, maintaining the opposing surfaces of cartilage graft and the recipient tissue free of small proteoglycans, such as lubricin, may be necessary to enhance the cartilage graft integration with surrounding tissues. Moreover, the inventors found that when the repair tissue in an osteochondral defect was loaded, the soft repair tissue resulted in more deformation in the axial direction and less in the radial direction. This mechanical behavior in the repair tissue increased the stress gradients across the interface and, therefore, created shear force along the interface that could ultimately deteriorate the integration between the healing tissue and the surrounding recipient tissue. Photochemical tissue bonding (PTB) may be used for sealing tissue surfaces using light and a photoactive dye to bond tissue together. PTB may provide a benefit to meniscus repair. A tethered diazopyruvate composition followed by irradiation may create phototriggerable crosslinked proteins, such as collagen, whereby the composition results in the sutureless wound closure.

One aspect of the present invention is directed to the repair of cartilage using cartilage grafts crafted, cleaned, disinfected, devitalized, and optionally recellularized. The devitalized cartilage grafts may be made sterile and preserved using various methodologies. Large devitalized cartilage grafts such as a hemicondyle may be fitted into the surgical site appropriate to the articulation needed to maximize interaction with the opposing cartilage on the bone in apposition to the graft being inserted. Small devitalized osteochondral plugs may be compression fitted into bores drilled into, and covering the cartilage defect such that the cancellous bone part of the graft fits tightly into the bore created using conventional surgical tools and the cartilage part of the graft may be slightly compressed around its perimeter as it is press fitted into the bore. The cartilage part of the graft should be at the same height as the surrounding cartilage of the recipient. The cartilage may be sectioned into slices parallel to the articular surface with various thicknesses. Different sizes and shapes of cartilage can be used to build various contour of the cartilage surface or have cells seeded to regenerate viable cell population in cartilage grafts. The cartilage grafts can also be skived or shaved into curls or flakes with irregular shapes. The cartilage curls and/or cartilage flakes can be mixed with or without a matrix and/or a carrier to become a filler to fill the cartilage defects. In addition, the cartilage curl and/or cartilage flake filler can be applied in combination with a cartilage slice or a cartilage disc or an osteochondral plug to repair a cartilage defect.

The present invention is directed to an cartilage component (part) of a graft which may be made acellular (devitalized) using one or more detergents, enzymes to modify the molecular aspects of the cartilage, and a recombinant endonuclease, for example BENZONASE® (Merk, Inc.). The devitalized graft may be processed to remove residuals of devitalization reagents sufficient to render the graft biocompatible, biohospitable, and recellularizable.

The present invention is also directed to a method and process of clinical use of cartilage components as grafts wherein the surface areas between the recipient and the implanted cartilage graft may be maximized and the interface between the recipient and the implanted cartilage graft may be molecularly cross-linked to control fluid movement when the repaired tissues may be subjected to loading as would occur during normal physiological activities such as, but not restricted to, walking, standing, sitting, running, jogging, or sleeping.

Figure 1B:
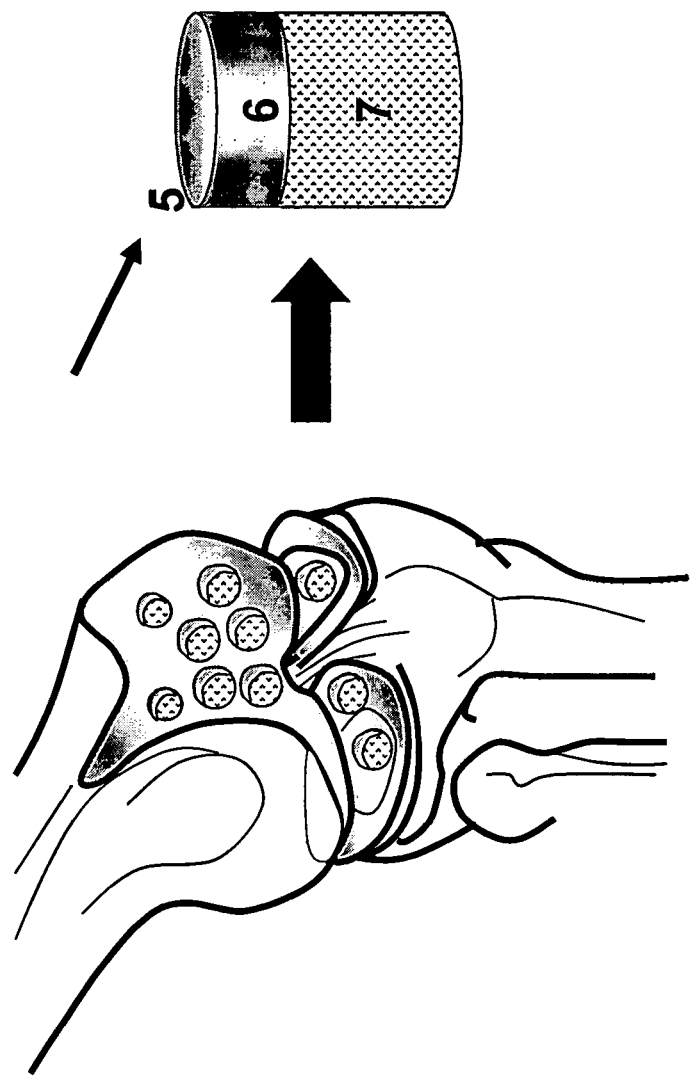
Figure 2:
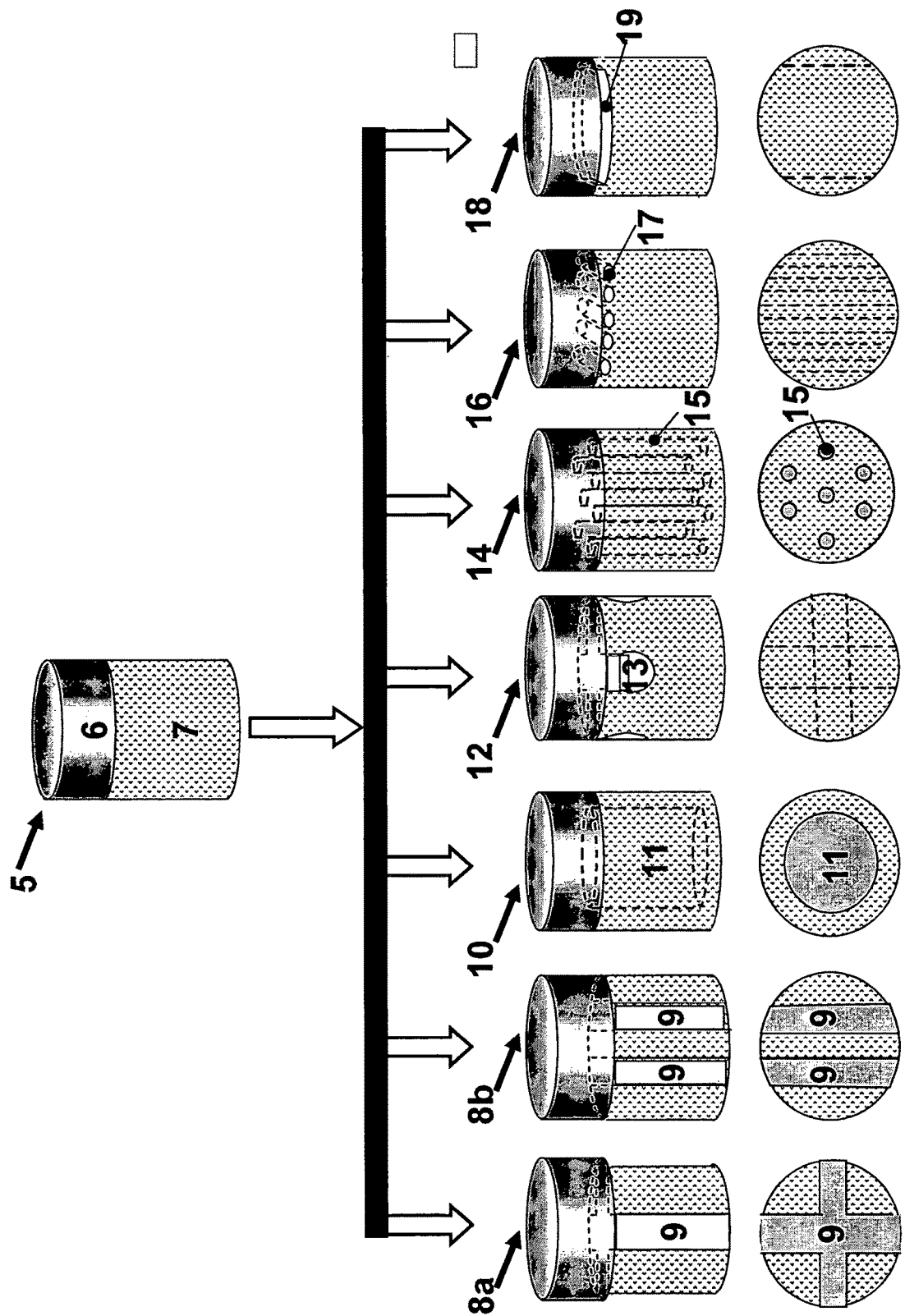
FIG. 2 illustrates an enlarged view of the cylindrical shaped osteochondral plugs with subchondral bone attached. The subchondral bone portion is crafted to have gaps or channels or slots. The last row of the figure shows the bottom view of the osteochondral plug.
Figure 3:
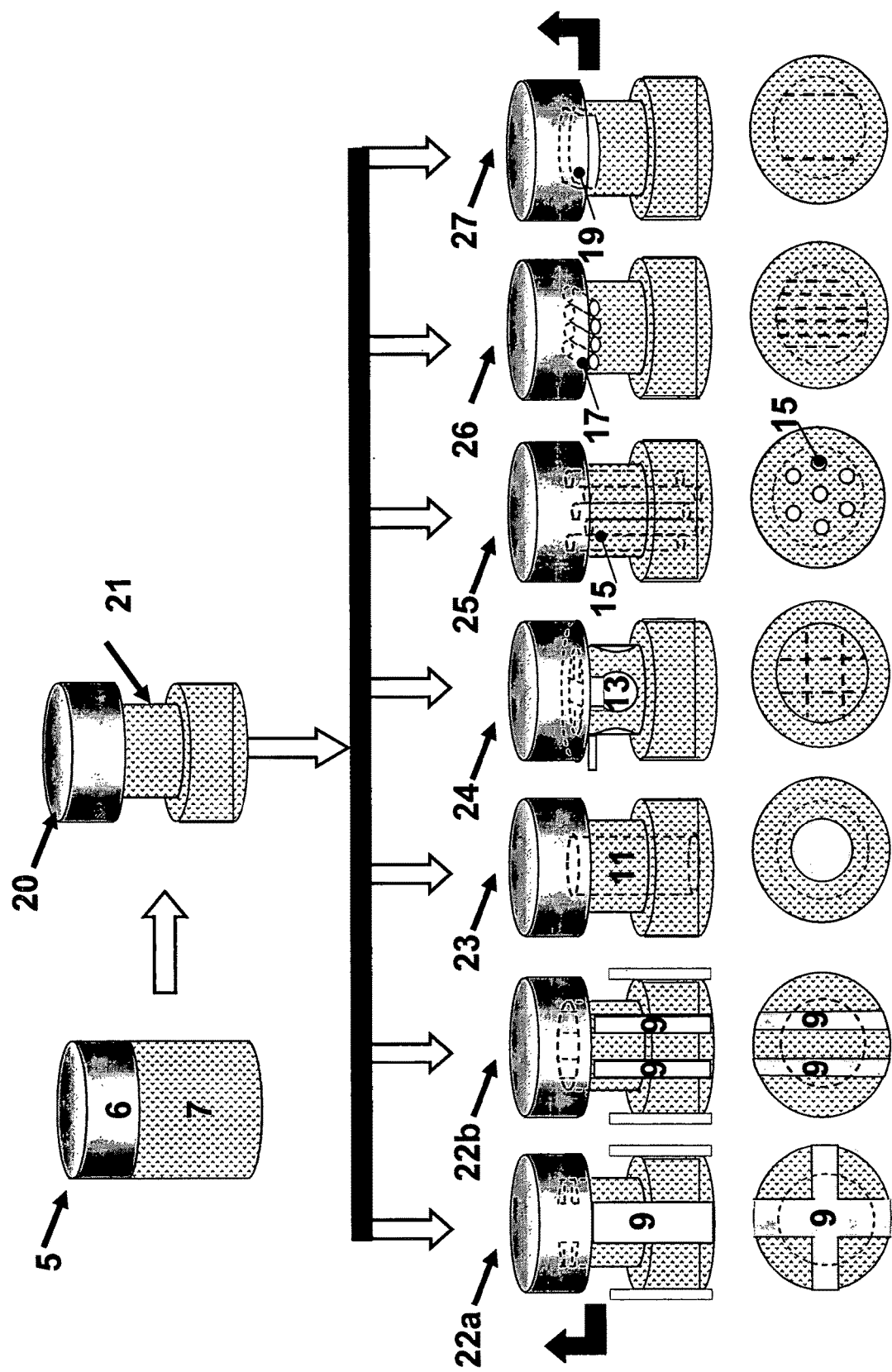
FIG. 3 illustrates an enlarged view of the dumbbell shaped osteochondral plugs with subchondral bone attached. The subchondral bone portion is crafted to have gaps or channels or slots. The last row of the figure shows the bottom view of the osteochondral plug.
Figure 4:
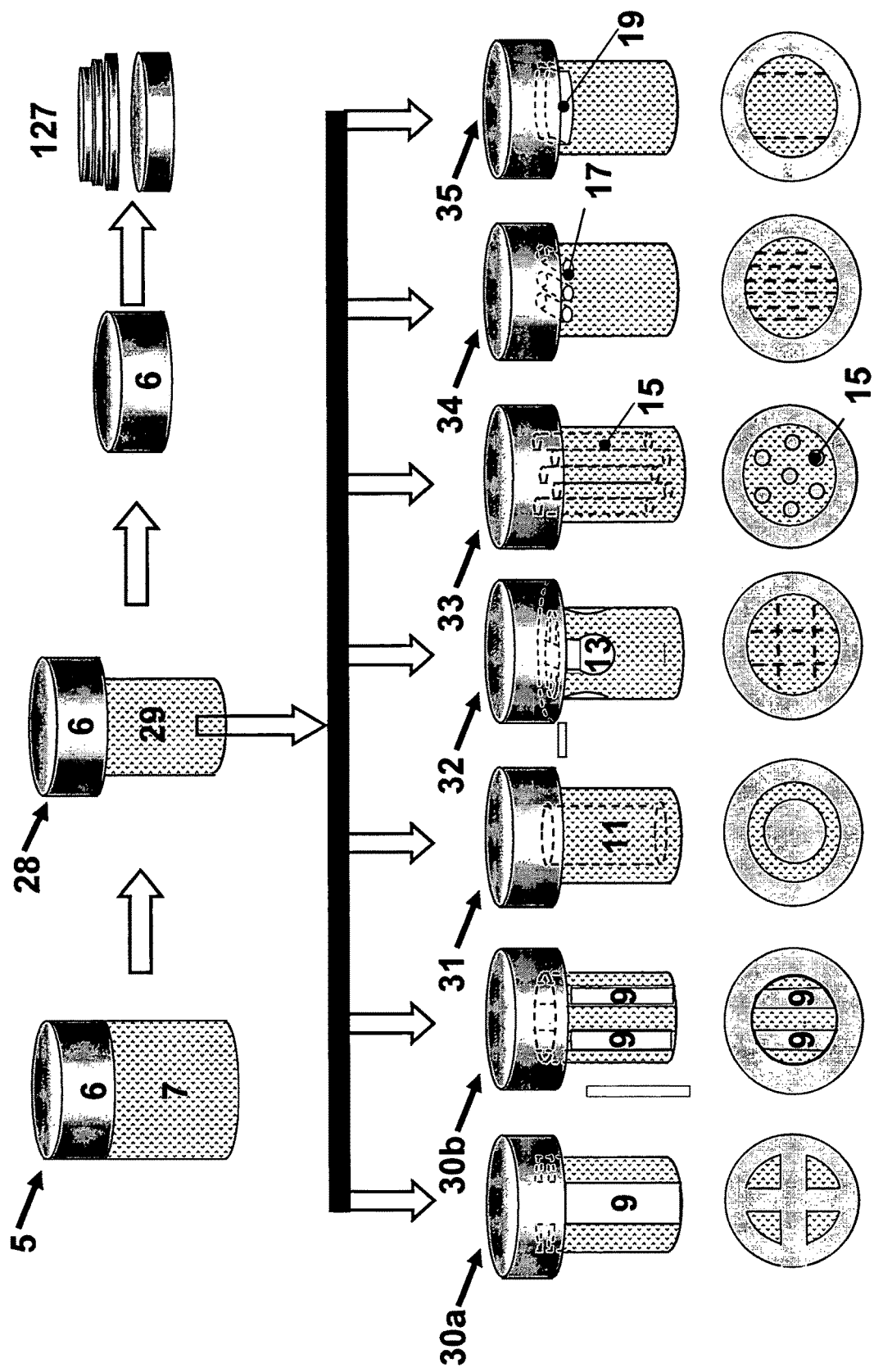
FIG. 4 illustrates an enlarged view of the step cylindrical shaped osteochondral plugs with subchondral bone attached. The subchondral bone portion is crafted to have gaps or channels or slots. The last row of the figure shows the bottom view of the osteochondral plug.

The human femoral condyles, tibial plateaus or femoral heads may be procured from a suitable donor, transported on wet ice to the processing facility, processed as whole or bisected into two hemicondyles or hemiplateaus, or cored out to obtain multiple osteochondral plugs as illustrated in FIG. 1. The orientation and anatomical location of the cartilage graft residing on the donor tissue can be recorded using a grid and a coordinate system so that it can be matched to the orientation and anatomical location of the recipient tissue. The osteochondral plug (5) can be crafted so that the diameter of the subchondral bone portion (7) is the same as that of the cartilage cap (6) to form a straight cylinder as illustrated in FIG. 2. Alternatively, the diameter of the subchondral bone portion (7) right underneath of the cartilage cap can be made to be slightly smaller than the cartilage cap (7) to form a dumbbell shape as illustrated in FIG. 3; or the diameter of the cartilage cap and the portion of the subchondral bone directly contacted with the cartilage cap can be in the same diameter as the bottom part of the subchondral bone portion, and the part of the subchondral bone portion between the bottom part and the portion directly contacted with the cartilage cap of the subchondral bone can be slightly smaller in diameter than the rest of the osteochondral plug to form a dumbbell shape. Furthermore, the diameter of the subchondral bone portion (7) can be made to be slightly smaller than the cartilage cap (6) to form a step cylindrical shape as illustrated in FIG. 4; or the diameter of the cartilage cap and the portion of the subchondral bone directly contacted with the cartilage cap can be slightly larger than the rest of the bone portion to form a step cylindrical shape. In addition, as illustrated in FIG. 2, the osteochondral bone portion (7) of the osteochondral plug (5) can be crafted into plugs (8a, 8b, 10, 12, 14, 16 or 18) to expose one or more portions of the cartilage cap (6) at the cartilage/bone interface. In one embodiment, portion of the tidemark at the cartilage and subchondral bone interface can be removed to expose one or more portions of the cartilage cap at the cartilage/bone interface. In another embodiment, one or more portions of the cartilage at the cartilage and subchondral bone interface can be removed along with the tidemark. In yet another embodiment, the portion of the circumferential area of the cartilage cap that is directly contacting the subchondral bone can be separated from the subchondral bone at the tidemark to allow the cartilage cap to deform laterally during compression in vivo.

Figure 5:
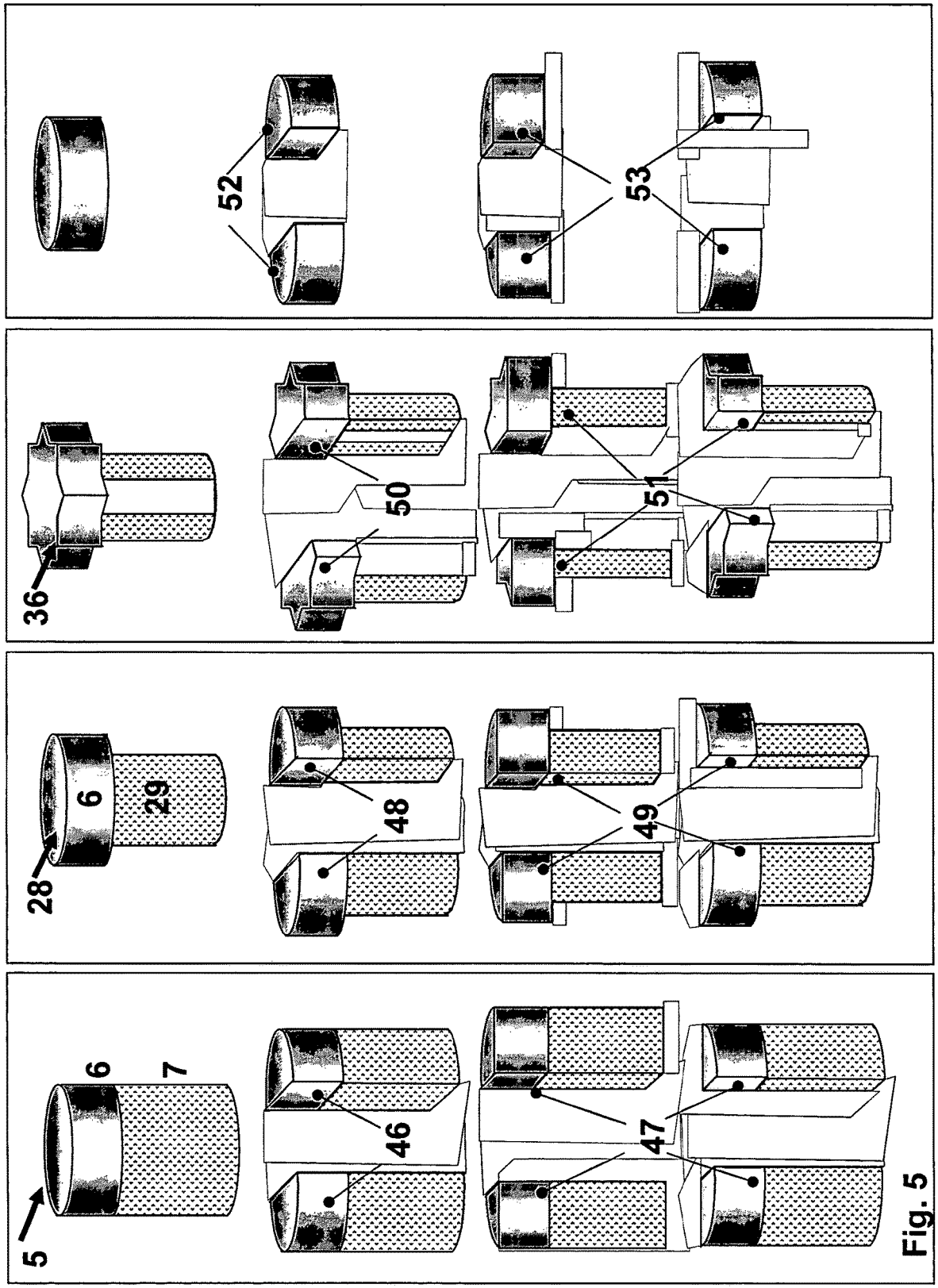
FIG. 5 illustrates an enlarged view of the osteochondral plugs or discs that are cut into two halves or four quarters along the diameter of the plug.
Figure 20:
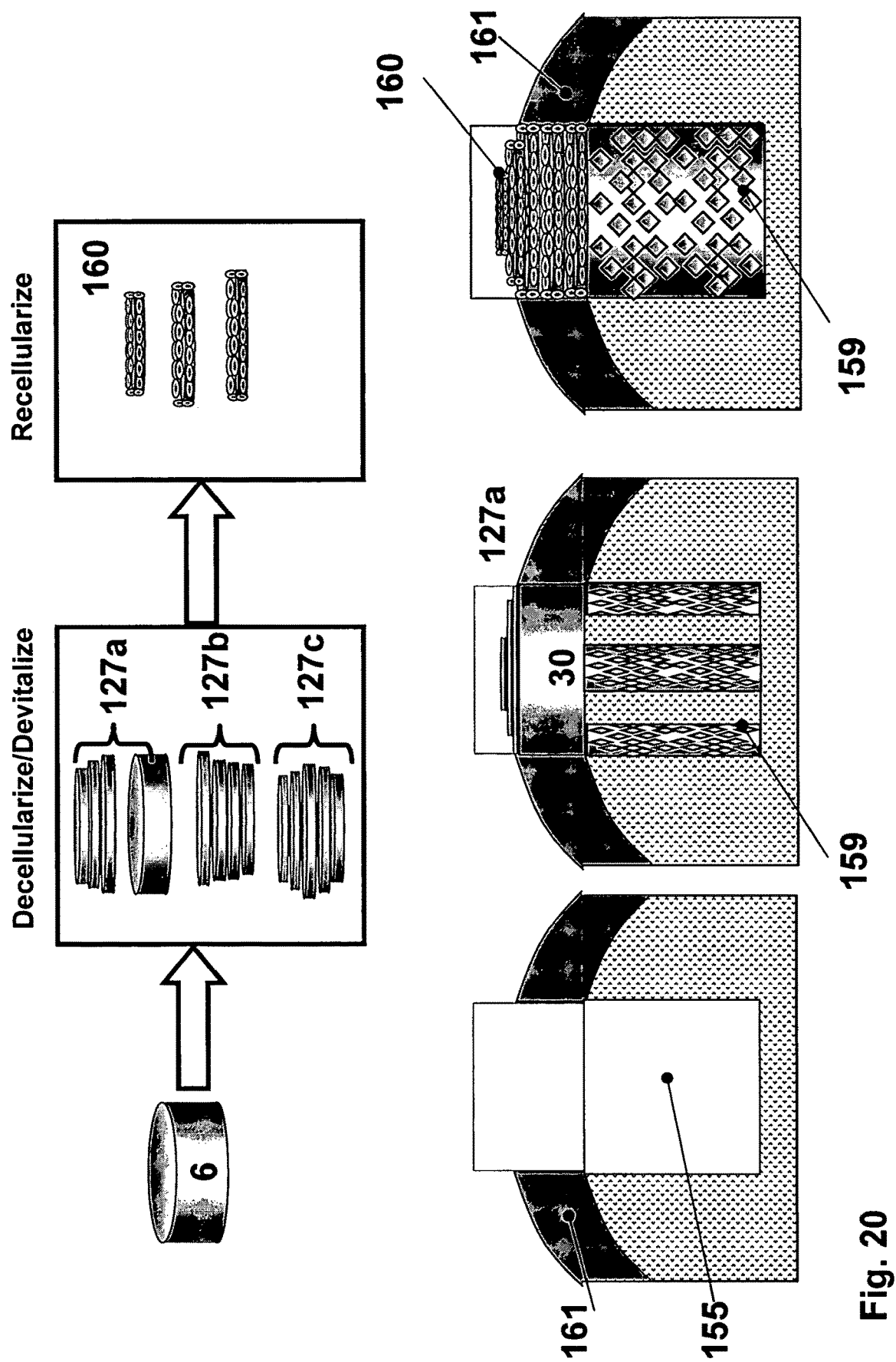
FIG. 20 illustrates an enlarged view of a procedure of creating a contoured cartilage graft. Devitalized and/or recellularized cartilage slides with varying diameters are stacked to match the curvature of the recipient tissue.

Many methods can be used to craft osteochondral plugs, the following examples are representative examples and are not meant to be limiting in any respect. Osteochondral plugs of the present invention may have a length of between about 1 and 20 mm and 8 and 20 mm and may have a diameter at its widest point of between about 8 and 20 mm As illustrated in FIG. 2, the osteochondral plug (8a) can be made by cutting the cylindrical bone portion (7) to obtain one or more gaps (9) that form angles between about 0 to about 180 degrees along the entire length of the bone portion up to the cartilage and osteochondral bone interface. The gaps may occupy one or more portions of the cartilage cap directly in contact with the subchondral bone, and may end at the deep, middle, or superficial zone of the cartilage cap along the cartilage depth direction and do not penetrate the superficial surface of the cartilage cap. The gaps can also be crafted parallel to the center line of the osteochondral plug and parallel to each other (8b). The width of the gaps can be between about ⅒ and about ½ of the diameter of the bone portion (7). The osteochondral plug (10) can be obtained by drilling/milling from bottom of the bone portion (7) along the center line to form a hollow cylinder. The hollow cylinder has a blind end center bore (11) that is along the whole length of the subchondral bone portion and ends at the cartilage and subchondral bone interface. The blind end center bore (11) may also occupy one or more portions of the cartilage cap directly contacted with the subchondral bone and may end at the deep, middle, or superficial zone of the cartilage cap along the cartilage depth direction and may not penetrate the superficial surface of the cartilage cap. The diameter of the blind end center bore (11) of the hollow cylinder ranges from about ½ to about ⅘ of the diameter of the subchondral bone portion of the osteochondral plug. The osteochondral plug (12) can be obtained by drilling/milling on the cylindrical surface of the bone portion (7) at the cartilage/bone interface to form one or more channels (13) that form about 0 to about 90 degree angles. The channel width may be from about ⅒ to about ½ of the diameter of the subchondral bone portion of the osteochondral plug. The channels may occupy one or more portions of the deep and/or middle zone of the cartilage cap along the depth direction and may not occupy the superficial zone of the cartilage cap. The osteochondral plug (14) can be obtained by drilling/milling from bottom of the bone portion (7) to form multiple about 0.5 to about 1 mm diameter channels (15) along the whole length of the bone portion up to the cartilage and osteochondral bone interface. The channels may occupy one or more portions of the cartilage cap directly contacted with the subchondral bone, may end at the deep, middle, or superficial zone of the cartilage cap along the cartilage depth direction, and may not penetrate the superficial surface of the cartilage cap. The osteochondral plug (16) can be obtained by drilling/milling through the cylindrical surface of the bone portion (7) at the cartilage/ bone interface to form multiple parallel about 0.5 to about 1 mm diameter channels (17). The channels have the length going through the entire diameter of the subchondral bone portion. The channels may occupy one or more portions of the deep and/or middle zone of the cartilage cap along the depth direction and may not occupy the superficial zone of said cartilage cap. Osteochondral plug (18) can be obtained by drilling/milling through the cylindrical surface of the bone portion (7) at the cartilage/bone interface to form one or more slots (19). The slots may have the depth going through the entire diameter of the subchondral bone portion, the height being about 0.35 to about 3 mm, and the width being about ⅒ to about ⅘ of the diameter of the subchondral bone of the osteochondral plug. The slots may occupy one or more portions of the deep and/or middle zone of the cartilage cap along the depth direction and may not occupy the superficial zone of the cartilage cap Similarly, as illustrated in FIG. 3, the osteochondral bone portion (21) of the dumbbell shape osteochondral plug (20) can be crafted into plugs (22a, 22b, 23, 24, 25, 26, or 27) to expose one or more portions of cartilage cap (6) at the cartilage/bone interface using the same crafting procedures described above in FIG. 2. In addition, as illustrated in FIG. 4, the osteochondral bone portion (29) of the step cylindrical shape osteochondral plug (28) can be crafted into plugs (22a, 22b, 23, 24, 25, 26, or 27) to expose one or more portions of cartilage cap (6) at the cartilage/bone interface using the same crafting procedures described above in FIG. 2. If desired, a cartilage disc (6) without the subchondral bone portion attached can be obtained by carefully cutting off the bone portion. The cartilage cap (6) of an osteochondral plug can also be sectioned into thin slices (127) with thicknesses ranging from about 50 to about 1000 μm as illustrated in FIG. 4. These cartilage slices can be trimmed to have circular, square, triangular, or star shapes. These slices can also be trimmed to have ascending or descending diameters and may be stacked together to create a contour that matches the contour of the defect site as illustrated in FIG. 20. The osteochondral plugs, cartilage disc, or cartilage slices described above can be further cut into two halves or four quarters along the diameter of the grafts as illustrated in FIG. 5.

The cartilage matrix can also be skived, grated or shaved using a bone fiber shaving device as illustrated in U.S. Patent Application Number 20040059364 to produce cartilage flakes or cartilage curls. This patent application is hereby incorporated by reference in its entirety. The cartilage tissue, such as a femoral condyle, can be fixed on a fixture underneath of a blade mounted in a cutter. The cutter moves horizontally relative to the cartilage tissue during a cutting stroke. The size and thickness of the cartilage flakes or curls can be controlled by adjusting the height of the cutter, the cutting angles, and the distance of each stroke relative to the cartilage tissue. The size of the cartilage flake or curl can be from about 0.001 to about 10 $cm^3$, about 0.001 to about 1 $cm^3$, about 0.01 to about 1 $cm^3$, about 0.1 to about 1 $cm^3$.

Figure 6:
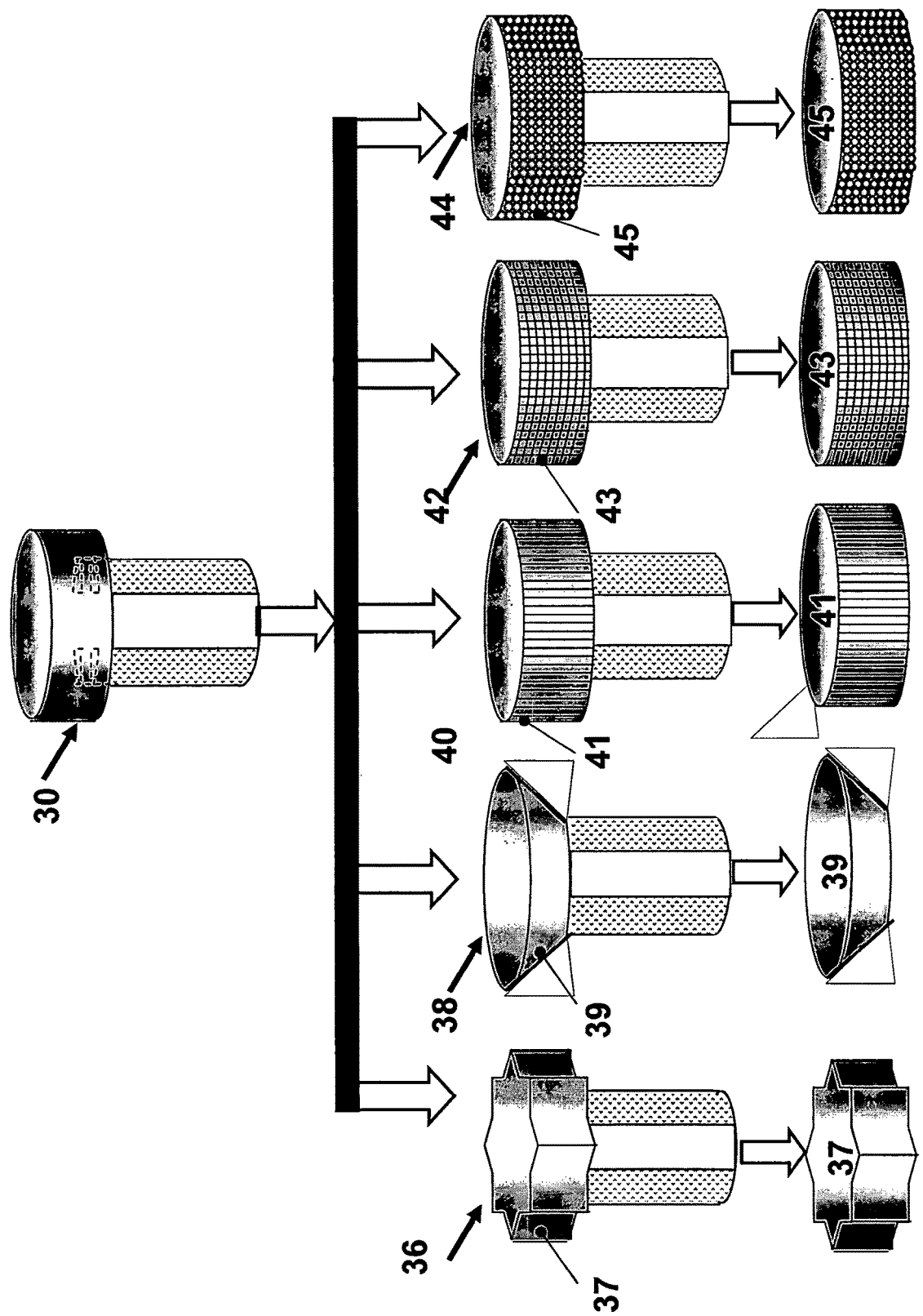
FIG. 6 illustrates an enlarged view of the osteochondral plugs where the circumferential surface of the cartilage caps is crafted to increase the surface area. The cartilage discs of full depth cartilage are obtained by cutting the crafted cartilage caps off the osteochondral plugs.
Figure 10:
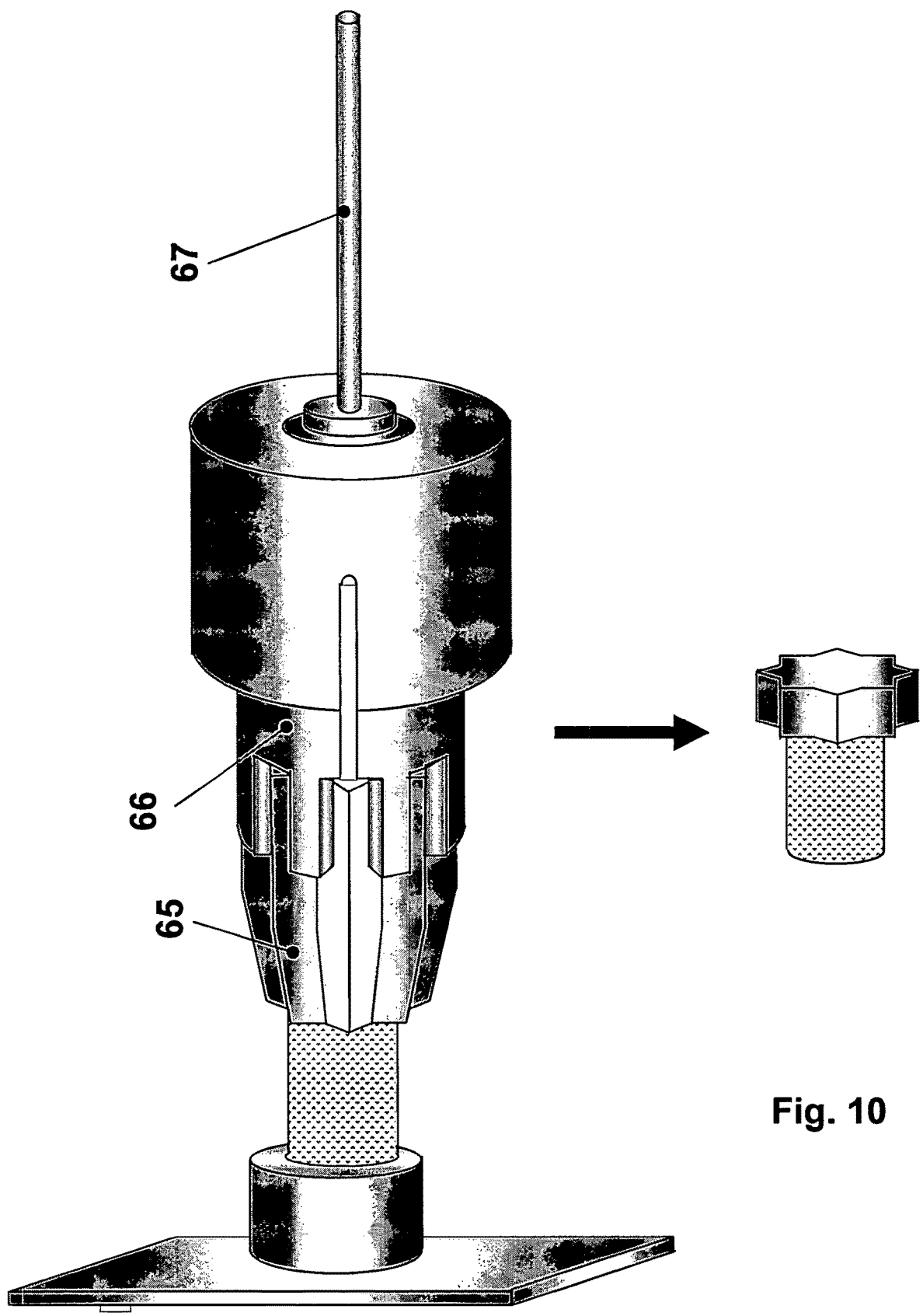
FIG. 10 illustrates an assembly of a cutting device, where a star-shaped cutting blade (65) is fit into an adaptor (66) and used to cut a star-shaped cartilage cap on the osteochondral plug. Then a pushing device (67) is used to push out the osteochondral plug from the adaptor/cutting blade assembly.
Figure 11:
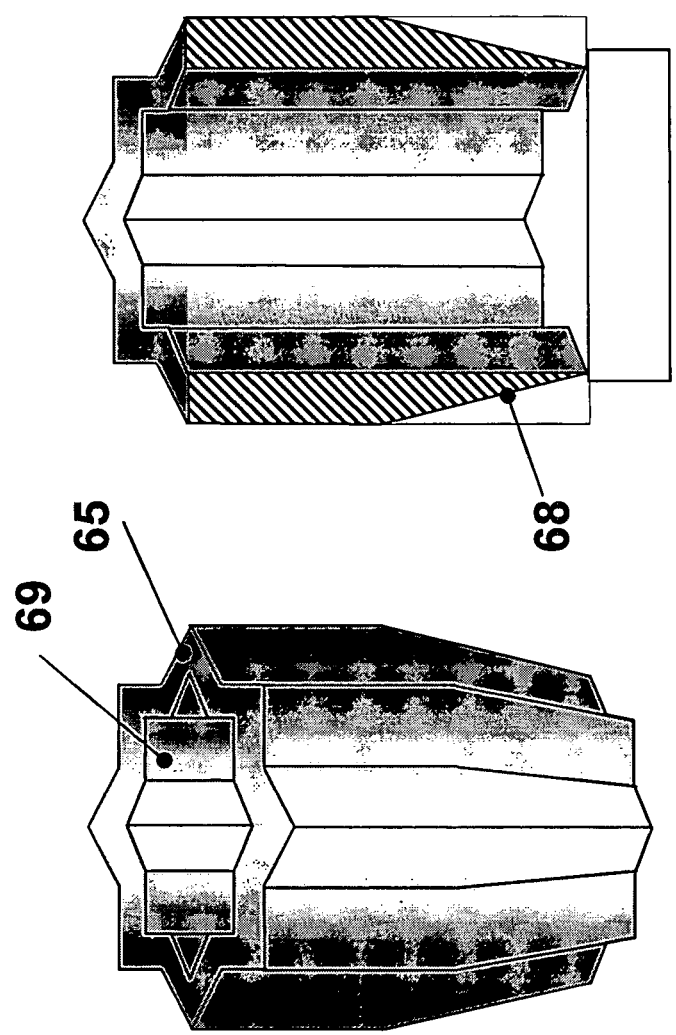
FIG. 11 illustrates a star-shaped cutting blade to cut a star-shaped cartilage cap on an osteochondral plug.
Figure 12:
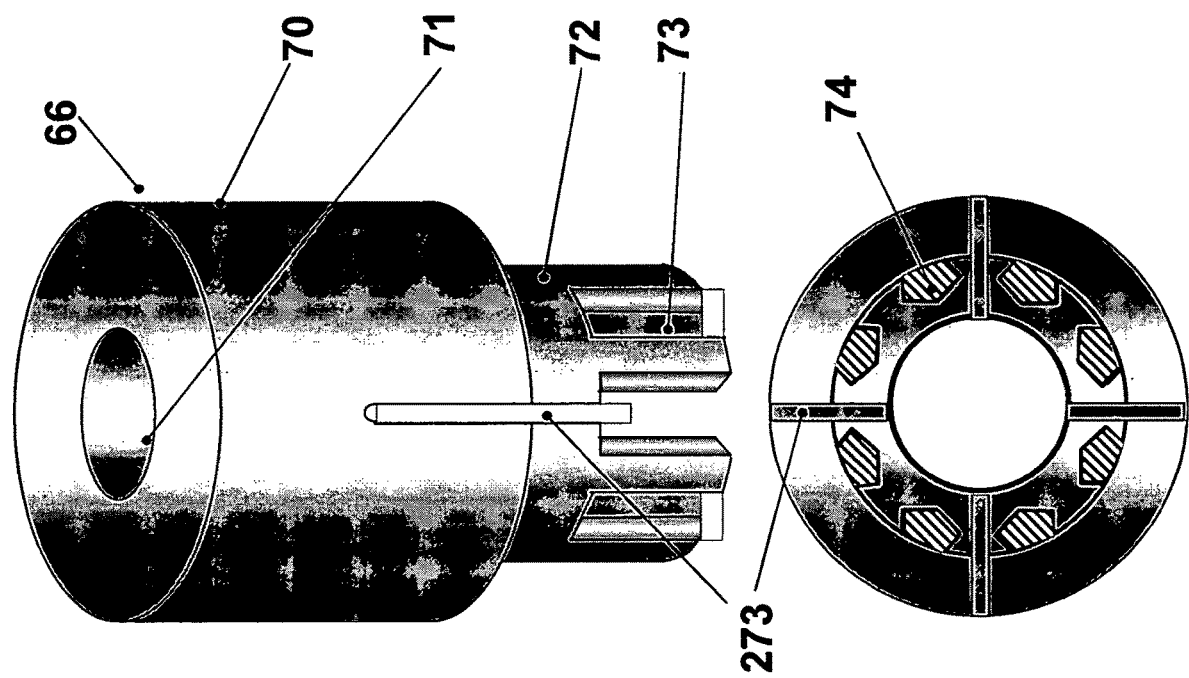
FIG. 12 illustrates an adaptor for the cutting blade.

The circumferential area of the cartilage portion of an osteochondral plug or a cartilage disc can be further crafted to maximize the circumferential surface and contact areas between the recipient cartilage being repaired and the cartilage graft, as illustrated in FIG. 6, to facilitate integration of the graft tissue to the recipient tissue. The surface area maximization can be conducted on a non-devitalized cartilage graft, or a devitalized cartilage graft, or a devitalized and recellularized cartilage graft. The star-shaped cartilage disc (37) or the star-shaped cartilage cap on osteochondral plug (36) can be obtained by coring a cartilage cap (6) with a custom made star-shaped cutting device as illustrated in FIG. 10-FIG. 12. The coring device may be composed of a star-shaped cutter (65) and an adaptor (66) (FIG. 10). The size and shape of the star-shaped cutter matches the size and shape of the star-shaped bore created in the defect sit. The star-shaped cutter may be designed so that its inner surface may be straight and the bottom portion of its outer surface may be angled to form a beveled sharp cutting edge FIG. 11. The adaptor (66) may be designed to have slots (73) that can fit into the teeth/protrusions of the stars on the star-shaped cutter (FIG. 12). The adaptor can also have four slits (273) to allow slight expansion of the adaptor when it fits into the star-shaped cutter. During application, the star-shaped cutter with the assist of the adaptor can punch and cut through the cartilage tissue from the osteochondral side or the superficial surface side of the cartilage graft. Then the cartilage graft can be removed from the coring device with the assistance of a pushing device (67). Optionally, if the cutting may be performed in the operating room right before the implantation, the star-shaped cartilage graft can be maintained in the cutter until implantation to prevent lateral expansion.

The tapered cylindrical cartilage disc with (38) or without (39) subchondral bone attached can be obtained using a lathe and an angled cutting tool. The diameter of the superficial region of the tapered cylindrical cartilage cap or disc (39) can be larger than the diameter of the deep region that may be connected to the subchondral bone. The straight cylindrical cap (6) or a tapered cylindrical cap (39) can be further crafted to maximize circumferential surface area by embossing with a die that has a straight or non-straight line pattern (40 and 41) or cross-line pattern (42 and 43). The straight cylindrical cap (6) or a tapered cylindrical cap (39) can also be further crafted to maximize the circumferential surface area by spraying or blasting microparticles onto the circumferential surface (44). The microparticles may be selected from a group of but not limited to demineralized bone matrix, freeze dried and fresh ground soft tissue, such as submucosa, fascia, muscle, dermis, cartilage, or amnionic membrane among others. The microparticles can also be microbeads made of biocompatible natural or synthetic polymers, such as collagen, chitosan, alginate, agarose, or hyaluronic acid. The microparticles can also be conjugated with cytokines or bioactive growth supplements. The cytokines may be one or more of, for example, IL-1αR antibody, TNF-a receptor antagonist, cyclooxygenase-2 specific inhibitors, MAP kinase inhibitors, NO synthase inhibitors, NF-κB inhibitors, and inhibitors of MMP. The bioactive growth supplements may be, for example, natural or recombinant FGF-family, TGF-family, IGF-1, PDGF, EGF, VEGF, HGF, PTHrP, Ihh, dexamethasone, insulin, transferrin, selenium, ITS, or ascorbate. The bioactive growth supplements may also be, for example, factors extracted from demineralized bone matrix, basement membrane, or submucosa matrix.

If desired, the circumferential surface and/or superior aspect of the cartilage part of the graft can be microperforated using enzyme linked microparticles as described in U.S. Pat. Nos. 6,432,712 and 6,416,995. These patents are hereby incorporated by reference in their entireties. The size of the microparticles may range from about 20 to about 500 micrometer. Alternatively, the microperforation can be conducted by mechanical or laser drilling on the cartilage such that holes of approximately 20 to 500 micrometer in diameter may be created. The microperforation can be conducted before or after the cleaning, disinfection, devitalization process.

Figure 7:
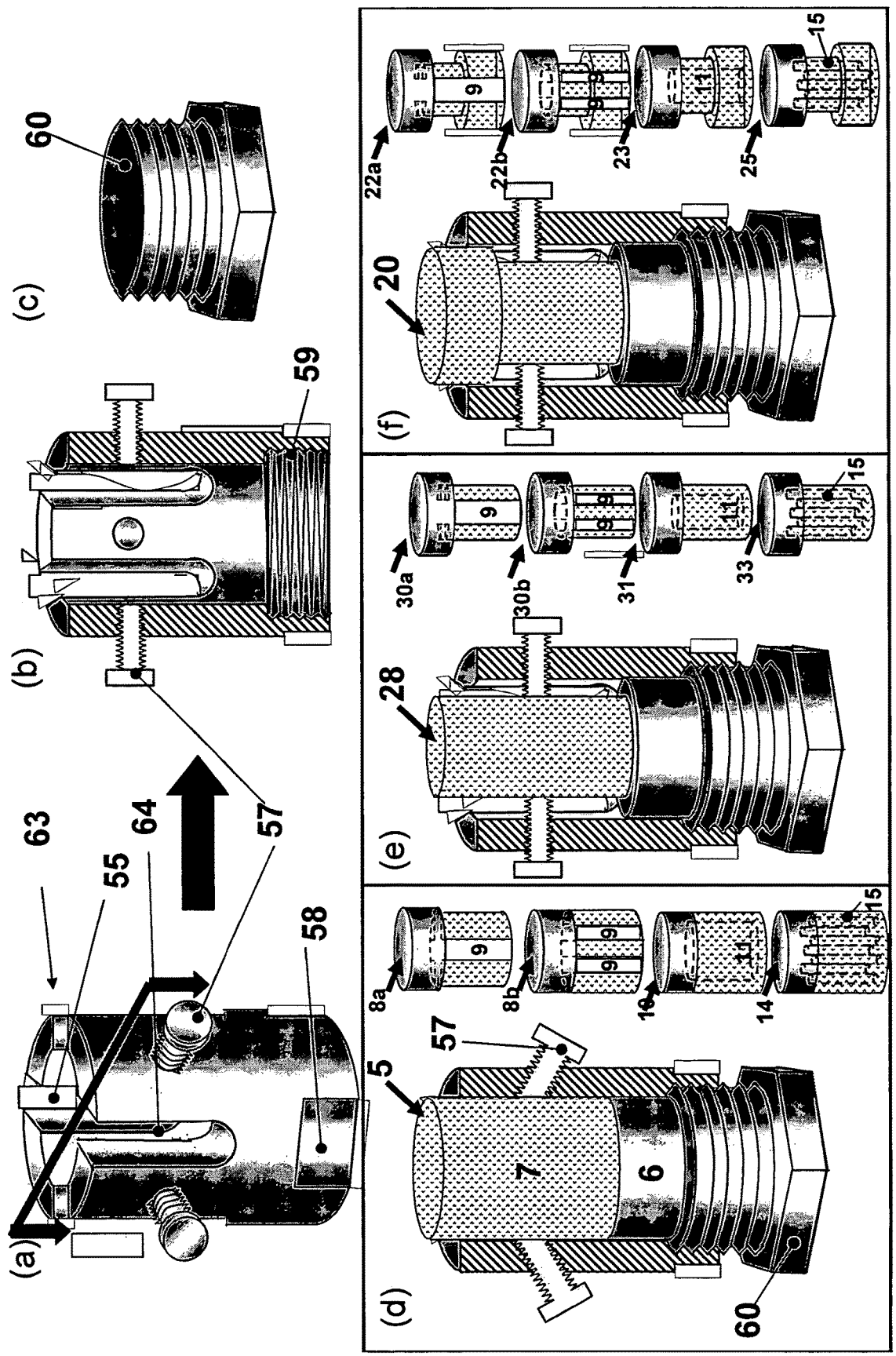
FIG. 7 illustrates a view of an osteochondral plug holder for crafting from the subchondral bone portion from the bottom to obtain more than one gaps that form angles between 0-180 degrees; or to obtain a hollow cylinder; or obtain multiple channels along the entire length of the subchondral bone portion up to the cartilage and subchondral bone interface.
Figure 8:
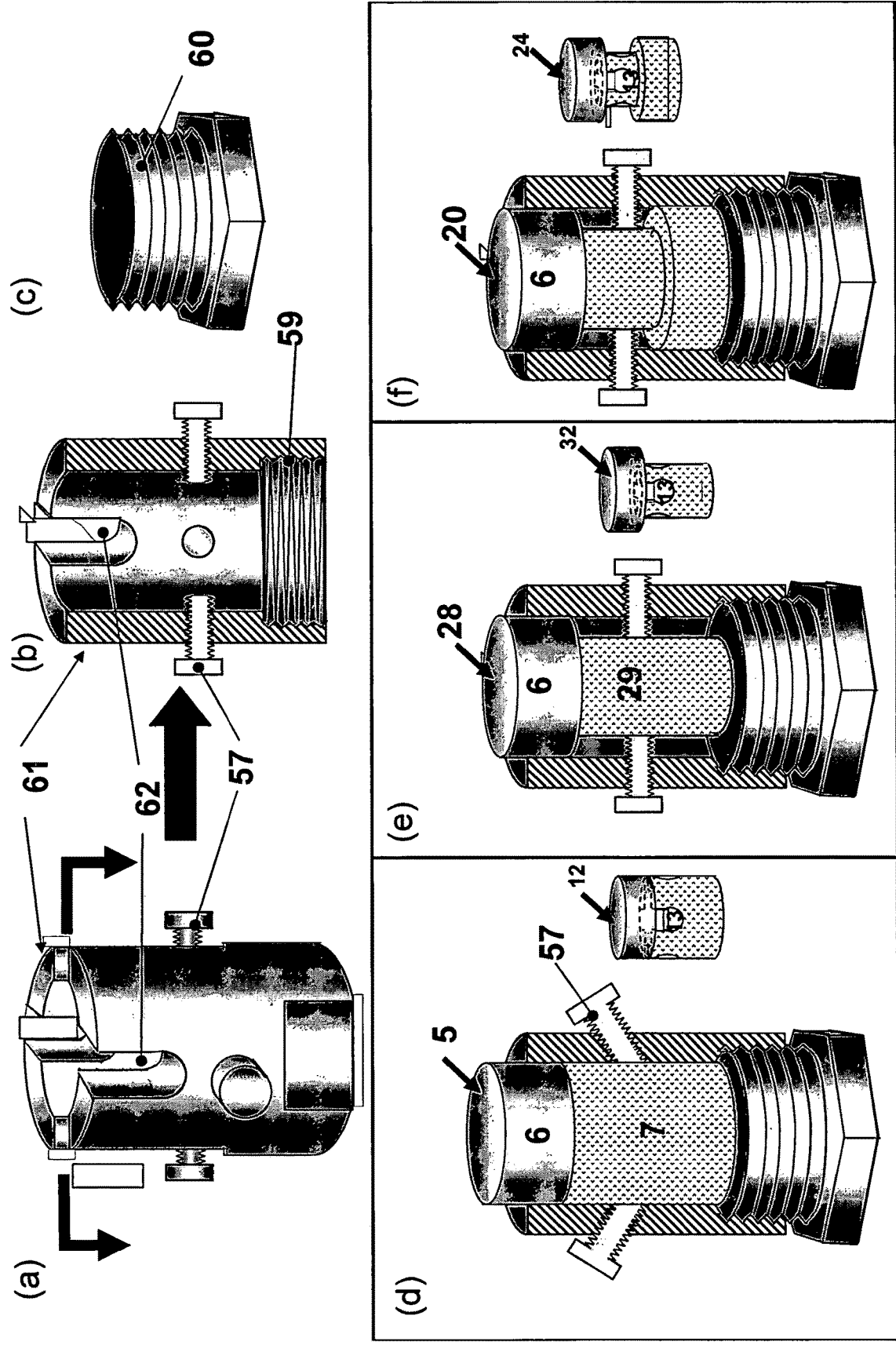
FIG. 8 illustrates a view of an osteochondral plug holder for crafting the cylindrical surface of the subchondral bone portion at the cartilage and subchondral bone interface to obtain more than one channels (13) that form 0-90 degree angles.

FIG. 7-FIG. 12 illustrate the tools used for crafting the osteochondral plugs or cartilage discs or slices. FIG. 7 demonstrates a holder (63) designed to secure an osteochondral plug (5) or (20) or (28) during crafting to obtain osteochondral plugs (8a), (8b), (10), and (14); or (22a), (22b), (23), and (25); or (30a), (31), respectively. The inner diameter of the cylindrical holder may be slightly larger than the largest diameter of the osteochondral plug. Slots (64) illustrated in FIG. 7(a) may be created along the longitudinal direction of the hollow cylindrical holder according to the width, the length, the amount and the orientation of the gaps (such as gap 9) to be created on the osteochondral plug. The inner surface of the bottom portion of the holder (63) may be threaded (59) so that a custom made bolt (60) can be threaded into to support the osteochondral plug along the longitudinal direction during crafting as illustrated in FIG. 7(d, e, and f). The outer surface of the bottom portion of the holder (63) may be flattened (58) and made rough so that the holder (63) can be fit into a lathe or a clamp of a drilling and/or milling machine during crafting. The clamp can be fixed on a table of the drilling/milling machine to enable movement in multiple directions. The table can also move both perpendicular to and parallel to the spindle axis of the endmill or drill bit to accomplish cutting. When the osteochondral plug may be inserted in the holder, the cartilage cap may be positioned to face down and supported by the custom made bolt (60) as illustrated in FIG. 7(d, e, and f). Then, in this aspect, set screws (57), preferably to be oriented 90 degrees apart, may be engaged to further secure the osteochondral plug within the holder (63) and to adjust the centerline of the osteochondral plug to be parallel to the cutting tool centerline or cutting direction. The set screws (57) can be oriented parallel to or at an angle relative to the articular surface of the osteochondral plug as illustrated in FIG. 7(d and e). The angular orientation of the set screw(s) can provide extra support on the osteochondral plug during crafting to minimize the stress exerting on the cartilage cap. The crafting can be conducted by sawing, or drilling and/or milling from the top, i.e., the bottom of the osteochondral bone portion. FIG. 8 demonstrates a holder (61) designed to secure an osteochondral plug (5) or (20) or (28) during crafting to obtain osteochondral plugs (12) or (24) or (32), respectively. The inner diameter of the cylindrical holder may be slightly larger than the largest diameter of the osteochondral plug. Slots (62) illustrated in FIG. 8(a and b) may be created along the longitudinal direction of the hollow cylindrical holder according to the diameter and the amount and the orientation of the channels (13) created on the osteochondral plug. The inner surface of the bottom portion of the holder (61) can be threaded (59) so that a custom made bolt (60) can be threaded into to support the osteochondral plug along the longitudinal direction during crafting as illustrated in FIG. 8(d, e, and f). The outer surface of the bottom portion of the holder (61) may be flattened (58) and made rough so that the holder (61) can be fit into a clamp during crafting. When the osteochondral is inserted in the holder, the cartilage cap may be positioned to face up and the bone portion may be supported by the custom made bolt (60) as illustrated in FIG. 8(*d, e,* and *f*). Then, in this aspect, set screws (57), preferably to be oriented 90 degrees apart, may be engaged to further secure the osteochondral plug within the holder (61) and to adjust the superficial surface of the cartilage cap on the osteochondral plug such that it may be parallel to the bottom surface of the custom made bolt (60). The set screws (57) can be oriented parallel to or at an angle relative to the articular surface of the osteochondral plug as illustrated in FIG. 8(*d* and *e*). The angular orientation of the set screw(s) can provide extra support on the osteochondral plug during crafting by forcing the bone portion of the osteochondral graft against the custom made bolt (60). The crafting can be conducted by drilling and milling through the slots (62) towards the circumferential surface of the bone portion of the osteochondral grafts. FIG. 9 demonstrates a holder (54) designed to secure an osteochondral plug (5) or (20) or (28) during crafting to obtain osteochondral plugs (16) and (18); or (26) and (27); or (34) and (35), respectively. The inner diameter of the cylindrical holder may be slightly larger than the largest diameter of the osteochondral plug. Slots (56) illustrated in FIG. 9(*a* and *b*) may be created along the circumferential direction of the hollow cylindrical holder according to the diameter and the amount and the orientation of the channels (17) or slots (19) to be created on the osteochondral plug. The inner surface of the bottom portion of the holder (54) may be threaded (59) so that a custom made bolt (60) can be threaded into to support the osteochondral plug along the longitudinal direction during crafting as illustrated in FIG. 9(*d, e,* and *f*). The outer surface of the bottom portion of the holder (54) may be flattened (58) and made rough so that the holder (54) can be fit into a clamp to facilitate gripping during crafting. When the osteochondral plug is inserted in the holder, the cartilage cap may be positioned to face up and the bone portion may be supported by the custom made bolt (60) as illustrated in FIG. 9(*d, e,* and *f*). Then, in this aspect, set screws (57), preferably to be oriented 90 degrees apart, may be engaged to further secure the osteochondral plug within the holder (54) and to adjust the superficial surface of the cartilage cap on the osteochondral plug to be parallel to the bottom surface of the custom made bolt (60). The set screws (57) can be oriented parallel to or at an angle relative to the articular surface of the osteochondral plug as illustrated in FIG. 9(*d* and *e*). The angular orientation of the set screw(s) can provide extra support on the osteochondral plug during crafting by forcing the bone portion of the osteochondral graft against the custom made bolt (60). The crafting can be conducted by drilling and milling through the slots (56) towards the circumferential surface of the bone portion of the osteochondral grafts.

The shaped cartilage grafts can be further cleaned and disinfected. Examples of cleaning solutions and cleaning and disinfection methods are described in U.S. Pat. Nos. 5,556,379, 5,820,581, 5,976,104, 5,977,034, 5,977,432, 5,797,871, and 6,024,735. These patents are hereby incorporated by reference in their entireties.

Figure 13A:
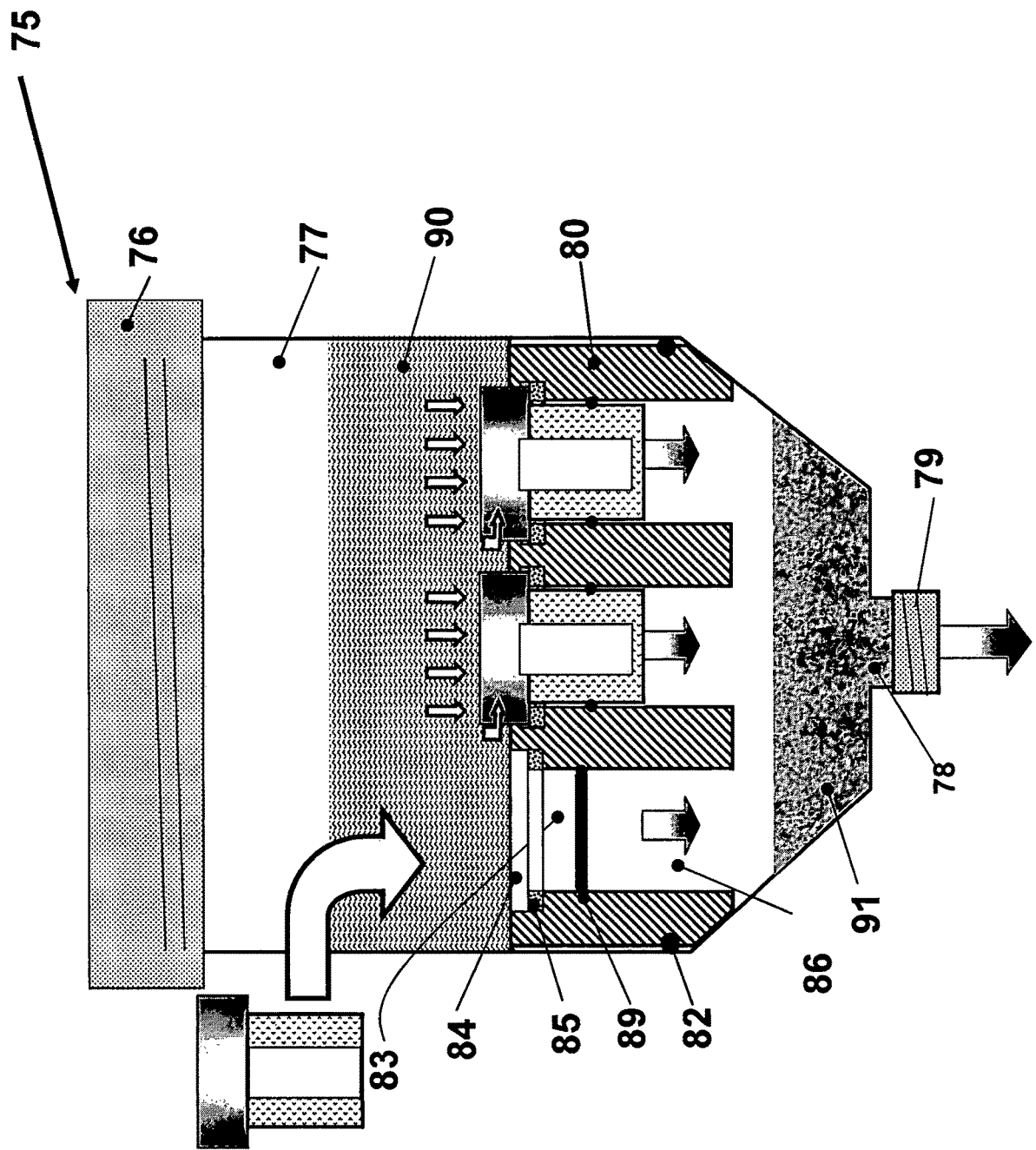
FIG. 13a illustrates a view of one embodiment of a cleaning/processing chamber (75) that can be fit into a centrifugation device. Cartilage grafts are fit into an insert (80) and the processing fluid is forced through the cartilage graft during centrifugation.
Figure 13B:
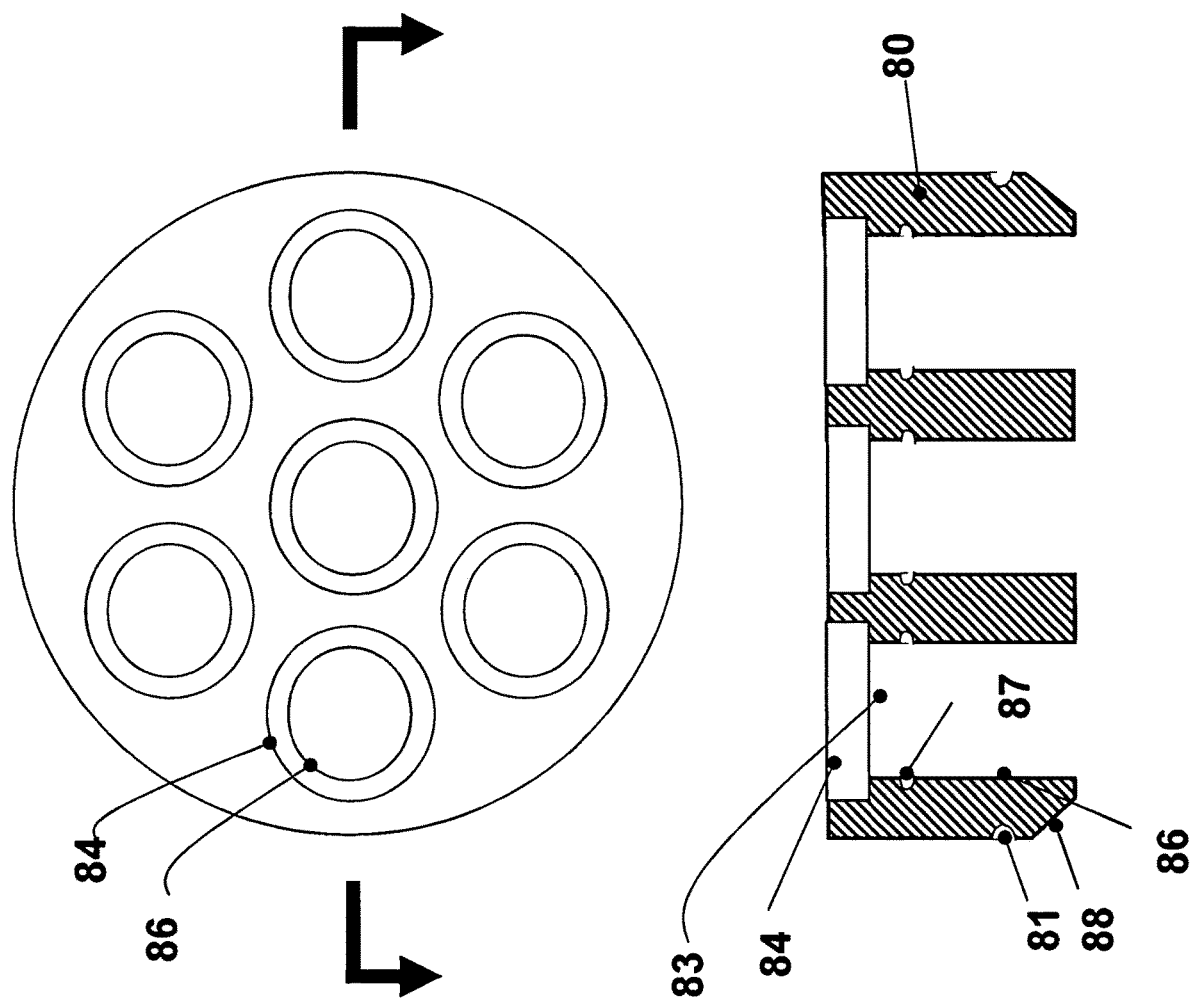
FIG. 13b illustrates a top and a side view of an insert (80), that the osteochondral plugs are fit into so that the superficial area of the cartilage surface is perpendicular to the fluid flow direction.
Figure 14:
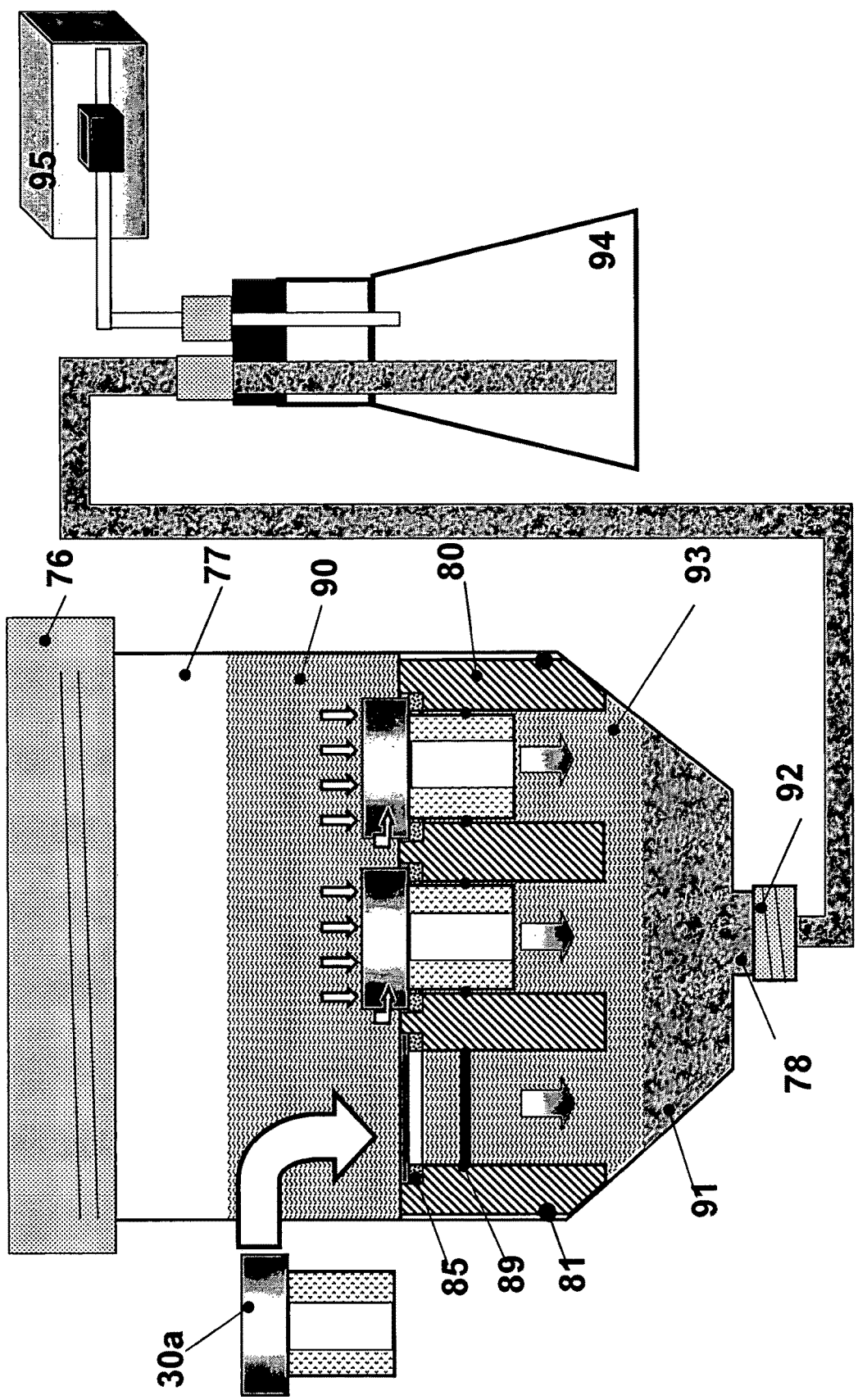
FIG. 14 illustrates a view of one embodiment of a cleaning/processing chamber (75). Cartilage grafts are fit into an insert (80) and processing fluid is forced through the cartilage graft using vacuum pressure.

For the cleaning process, the crafted osteochondral plugs can be placed into a processing chamber (75) shown in FIG. 13*a* such that the osteochondral bone portion with or without gaps or a bore or channels or slots described above may be tightly fit into the cylindrical step holes in an insert (80). The insert (80) as illustrated in FIG. 13*b* can incorporate multiple osteochondral plugs, cartilage discs, or slices and has a rubber ring (82) to create a seal between the wall of the processing chamber and the insert. The diameter of the top portion (84) of the step cylindrical hole (83) in the insert (80) is slightly larger than the diameter of the cartilage portion on the osteochondral plug. A porous ring (85), made of a porous material such as porous titanium, stainless steel, ceramics, hydroxyapatite, calcium phosphate, or calcium sulfate, with a center hole diameter slightly larger than the bottom portion (86) of the step cylindrical hole (83) can be fit in the top portion (84). The diameter of the bottom portion (86) of the step cylindrical hole (83) may be slightly larger than the osteochondral bone portion of the osteochondral plug. A rubber ring (89) may be fitted in the bottom portion of the step cylindrical hole (83). When any one of the osteochondral plugs in FIG. 2-FIG. 5 is fitted into the step cylindrical hole (83), the inferior surface facing the osteochondral bone portion of the cartilage cap (6, 37, 39, 41, 43, or 45) may be placed against the top surface of the porous ring (85) as illustrated in FIG. 13*a*. The bone portion can be fit into the bottom part (86) of the cylindrical hole (83) with the rubber ring (89) on the peripheral surface that creates a seal. The cleaning solution (90), i.e., AlloWash® Solution (LifeNet, Inc., Virginia Beach, Va.), may be added from the top of the processing chamber. Under centrifugal force, preferably from about 100 to about 2000 rcf, more preferably from about 500 to about 1500 rcf, most preferably from about 1000 to about 1400 rcf, the cleaning solutions can be induced to migrate through the tissues and into the bottom of the processing chamber. Optionally, sonication can be conducted preferably for about 5 minutes to about 24 hours, more preferably for about 0.5 to about 12 hours, and at frequency of preferably from 1 Hz to about 200 Hz, more preferably from 50 Hz to about 100 Hz before the centrifugation process using an ultrasonic cleaner. Alternatively, the cleaning process can be conducted by combining optional sonication and vacuum pressure (FIG. 14). The cleaning solution (90 and 93), i.e., AlloWash® Solution, can be added into the processing chamber to have the entire graft submerged. The grafts can be optionally sonicated preferably for about 5 minutes to about 24 hours, more preferably for about 0.5 to about 12 hours, and at frequency of preferably from 1 Hz to about 200 Hz, more preferably from 50 Hz to about 100 Hz. Then the grafts can be subjected to negative pressure from the bottom port (78), collection beaker (94), and the pump (95). After centrifugation or vacuuming, the waste (91) may be discarded and the osteochondral plugs may be removed from their respective processing chambers and the surface aspects of the plugs may be flushed using pulsatile lavage with AlloWash® Solution, and optionally isotonic saline to remove residual AlloWash® Solution from the grafts.

Figure 17A:
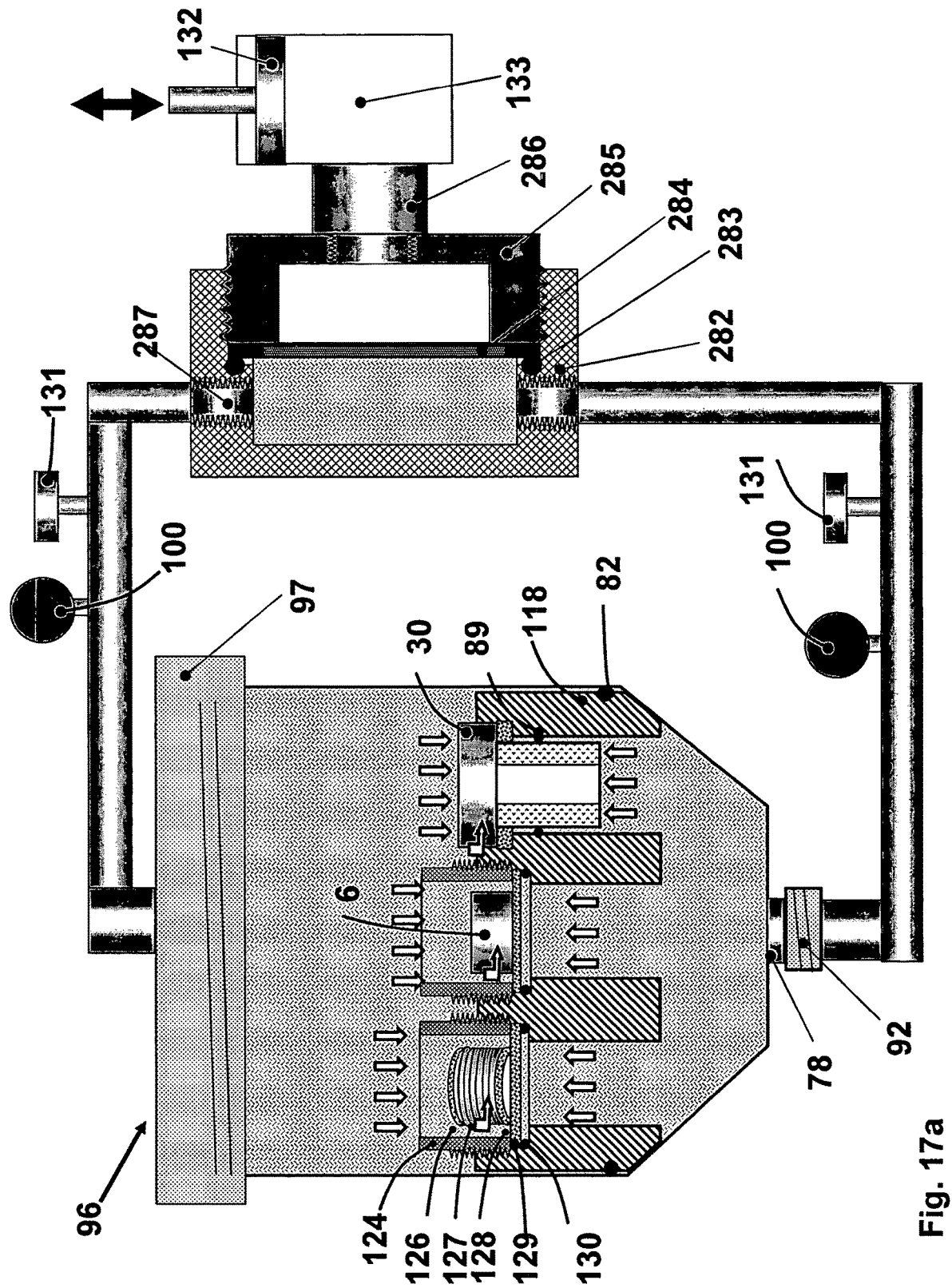
FIG. 17a illustrates a cyclic hydrodynamic pressurized devitalization system where the fluid is cyclically pressurized within the cleaning/processing chamber (96).

After the cleaning and disinfecting process, osteochondral plugs or cartilage discs or slices or flakes or curls can be placed in a processing chamber and devitalized using, for example, one of the following methods: agitating on a shaker or rocker or mixer, or using centrifugal force (FIG. 13*a*), or using vacuum pressure (FIG. 14), or using a flow through system (FIG. 15), or using cyclic hydrodynamic pressure (FIG. 17*a*). United States patents directed toward the decellularization and/or devitalization of tissue, include U.S. Pat. Nos. 6,743,574, 6,734,018, 6,432,712, 6,416,995 and U.S. Patent application numbers 2004/0076657, 2004/0067582, and 2003/0219417. These patents and patent applications are incorporated by reference in their entireties.

After cartilage grafts are properly placed in the processing chamber or tubes, the cartilage grafts of the osteochondral plugs or discs or slices are optionally modified in a pretreatment solution. The pretreatment solution may be composed of about 0.1 to about 10 U/ml enzymes, such as chondroitinase ABC in a buffer, such as Tris/NaAc among others. The pretreatment step can be conducted, for example, on a shaker or rocker or mixer, or in a processing chamber (75 or 96) under a relative centrifugal force, or under a vacuum pressure less than the ambient pressure, or in a pressure induced flow through system, or under cyclic hydrodynamic pressure. By varying the duration of the pretreatment and the concentration of the chondroitinase ABC in the pretreatment solution, the amount of proteoglycan to be removed can be controlled. Following completion of the pretreatment, the pretreatment solution may be removed from the tubes or the processing chamber (75 or 96) and may be replaced with a rinsing solution. The cartilage grafts can be rinsed in the rinsing solution, such as water, saline, phosphate buffer saline, RPMI media, balanced Hank's solution, Lactated Ringer's solution, DMEM/F12, F12, or DMEM media, among others, in the corresponding processing chamber or tubes. The rinsing solution may be then replaced with an extracting solution (Buffer, sodium dodecylsulfate or N-lauroyl sarcosinate or CHAPS, and BENZONASE® among others) with decontaminating agents to disinfect the tissues and to digest the nucleic acids present in the plugs. The grafts can be incubated in a test tube that fits onto a shaker or rocker or mixer, or in a processing chamber (75 or 96) under a relative centrifugal force, or under vacuum pressure, or in a flow through system, or under cyclic hydrodynamic pressure to induce a fluid flow through the tissue to be devitalized as illustrated in FIG. 13-FIG. 17. Following completion of the devitalization, the extracting solution may be removed from the tubes or the processing chamber (75 or 96) and may be replaced by a rinsing solution, such as water, saline, phosphate buffer saline, RPMI media, balanced Hank's solution, Lactated Ringer's solution, DMEM/F12, F12, or DMEM media, among others. The grafts can be incubated again in a test tube that fits onto a shaker or rocker or mixer, or in a processing chamber (75 or 96) under a relative centrifugal force, or under vacuum pressure, or in a flow through system, or under cyclic hydrodynamic pressure to induce a fluid flow through the tissue to be devitalized.

For devitalization under agitation, osteochondral plugs or cartilage discs or slices or flakes or curls can be placed in one or multiple test tubes that may be fixed on a shaker or rocker or mixer. Cartilage grafts can be incubated with a pretreatment solution on preferably at a temperature from about 4° C. to about 45° C., more preferably from about 15° C. to about 37° C., for a period of time preferably of about 1 to about 24 hours, more preferably of about 1 to about 16 hours, and under agitation preferably of about 10 to about 1000 rpm, more preferably of about 100 to about 500 rpm. Cartilage grafts can be washed with isotonic saline solution preferably at a temperature from about 4° C. to about 42° C., more preferably from about 15° C. to about 37° C., for a period of time preferably of about 10 minutes to about 24 hours, more preferably of about 15 to about 60 minutes, and under agitation preferably of about 10 to about 1000 rpm, more preferably of about 100 to about 500 rpm. After washing with saline two more times, the isotonic saline solution may be replaced by the extracting solution. The test tubes containing cartilage grafts can be incubated preferably at a temperature from about 4° C. to about 45° C., more preferably from about 15° C. to about 37° C., for a period of time preferably of about 1 to about 24 hours, more preferably of about 1 to about 16 hours, and under agitation preferably of about 10 to about 1000 rpm, more preferably of about 100 to about 500 rpm. Following completion of the devitalization process, the tubes may be drained of the extracting solution and replaced with a rinsing solution. The cartilage grafts can be washed in the rinsing solution preferably at a temperature from about 4° C. to about 45° C., more preferably from about 15° C. to about 37° C., for a period of time preferably of about 10 minutes to about 24 hours, more preferably of about 15 to about 60 minutes, and under agitation preferably of about 10 to about 1000 rpm, more preferably of about 100 to about 500 rpm. The washing can be repeated for two more times. The tubes may be then drained of the rinsing solution and replaced with a storage solution. The cartilage grafts can again be incubated on preferably at a temperature from about 4° C. to about 42° C., more preferably from about 15° C. to about 37° C., for a period of time preferably of about 1 to about 24 hours, more preferably of about 1 to about 16 hours, and under agitation preferably of about 10 to about 1000 rpm, more preferably of about 100 to about 500 rpm.

For devitalization under centrifugal force, osteochondral plugs can be fit into the cylindrical step holes in an insert (80 in FIG. 13a) as described in the cleaning process. Cartilage discs or slices can be placed on a porous ring (85) in the top portion (84) of the step cylindrical hole (83) in the insert (80). The insert can be made of biocompatible polymers such as Teflon, biocompatible metal such as titanium or stainless steel. The pretreatment solution may be transferred into the top part of the chamber. The chamber can be centrifuged preferably at a temperature from about 4° C. to about 45° C., more preferably from about 15° C. to about 37° C., for a period of time preferably of about 10 minutes to about 24 hours, more preferably of about 30 minutes to about 18 hours, most preferably of about 1 hour to about 16 hours, and at a speed preferably of from about 10 to about 2000 rcf, more preferably of about 100 to about 1500 rcf, most preferably of about 500 to about 1000 rcf. The pretreatment solution in both the top and the bottom portion of the chamber may be removed and the bottom cap (79) may be closed. Then the rinsing solution may be transferred into the top portion of the processing chamber. The chamber can be centrifuged preferably at a temperature from about 4° C. to about 45° C., more preferably from about 15° C. to about 37° C., for a period of time preferably of about 10 minutes to about 24 hours, more preferably of about 30 minutes to about 18 hours, most preferably of about 1 hour to about 16 hours, and at a speed preferably of from about 10 to about 2000 rcf, more preferably of about 100 to about 1500 rcf, most preferably of about 500 to about 1000 ref. The washing can be optionally repeated and the rinsing solution may be drained. The extracting solution may be then transferred into the top portion of the processing chamber (FIG. 13a). The processing chamber containing cartilage grafts can be centrifuged preferably at a temperature from about 4° C. to about 45° C., more preferably from about 15° C. to about 37° C., for a period of time preferably of about 10 minutes to about 24 hours, more preferably of about 30 minutes to about 18 hours, most preferably of about 1 hour to about 16 hours, and at a speed preferably of from about 10 to about 2000 rcf, more preferably of about 100 to about 1500 rcf, most preferably of about 500 to about 1000 rcf, to facilitate penetration of the fluid into the cartilage graft. Following completion of the devitalization process, the processing chamber may be drained of extracting solution and replaced with a rinsing solution, such as water, saline, phosphate buffer saline, RPMI media, balanced Hank's solution, Lactated Ringer's solution, DMEM/F12, F12, or DMEM media. The chamber can be centrifuged preferably at a temperature from about 4° C. to about 45° C., more preferably from about 15° C. to about 37° C., for a period of time preferably of about 10 minutes to about 24 hours, more preferably of about 30 minutes to about 18 hours, most preferably about 1 hour to about 16 hours, and at a speed preferably of from about 10 to about 2000 rcf, more preferably of about 100 to about 1500 rcf, most preferably of about 500 to about 1000 rcf. The washing can be repeated twice and the rinsing solution may be drained. The rinsing solution may be replaced with a storage solution. The chamber can be centrifuged preferably at a temperature from about 4° C. to about 45° C., more preferably from about 15° C. to about 37° C., for a period of time preferably of about 10 minutes to about 24 hours, more preferably of about 30 minutes to about 18 hours, most preferably of about 1 hour to about 16 hours, and at a speed preferably of from about 10 to about 2000 rcf, more preferably of about 100 to about 1500 rcf, most preferably of about 500 to about 1000 rcf.

Figure 15:
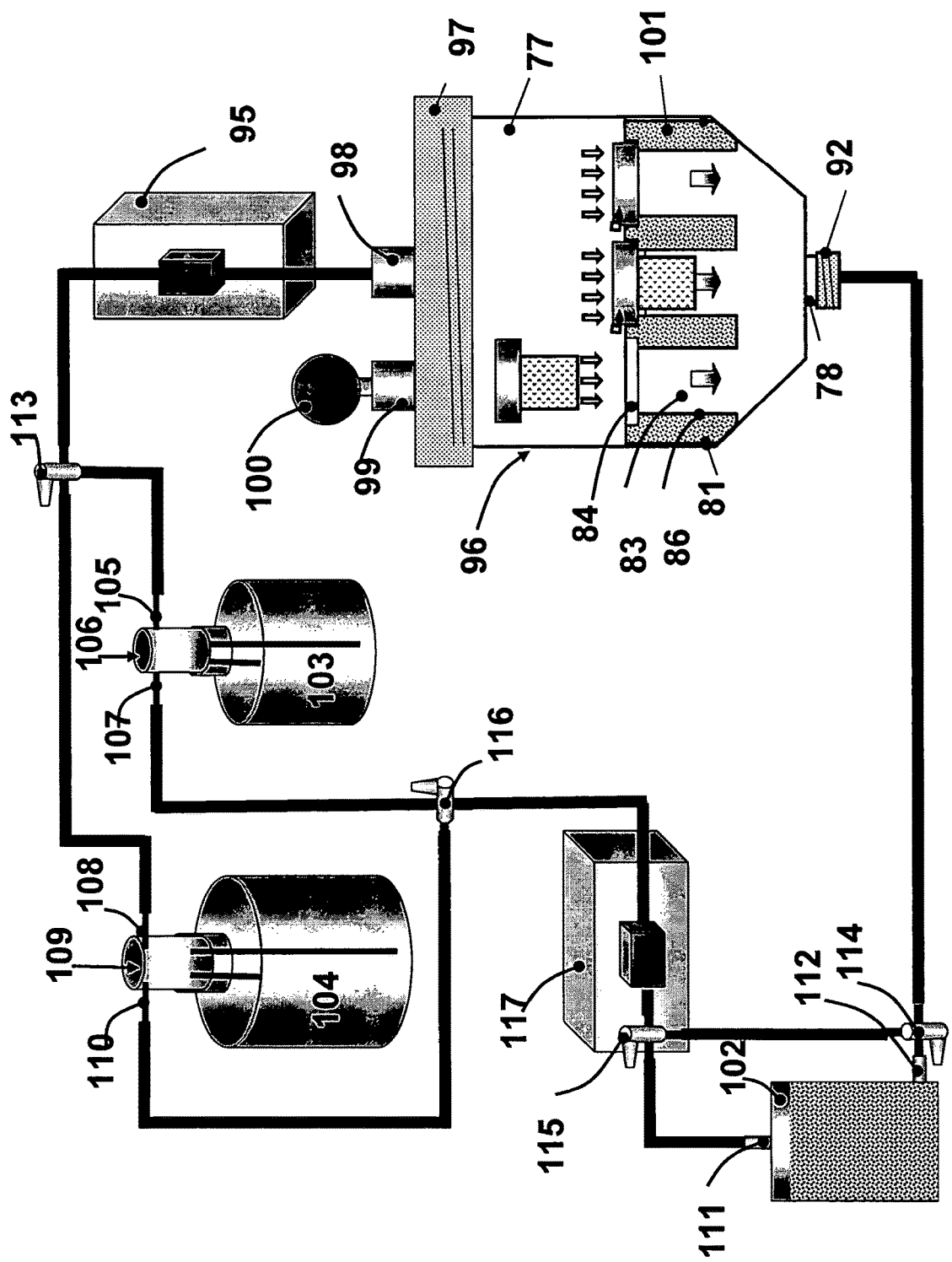
FIG. 15 illustrates a pressurized flow through devitalization system where fluids are recirculated between a cleaning/processing chamber (96) with insert (101) and a reservoir. The superficial surface of the cartilage graft is perpendicular to the fluid flow direction.
Figure 16A:
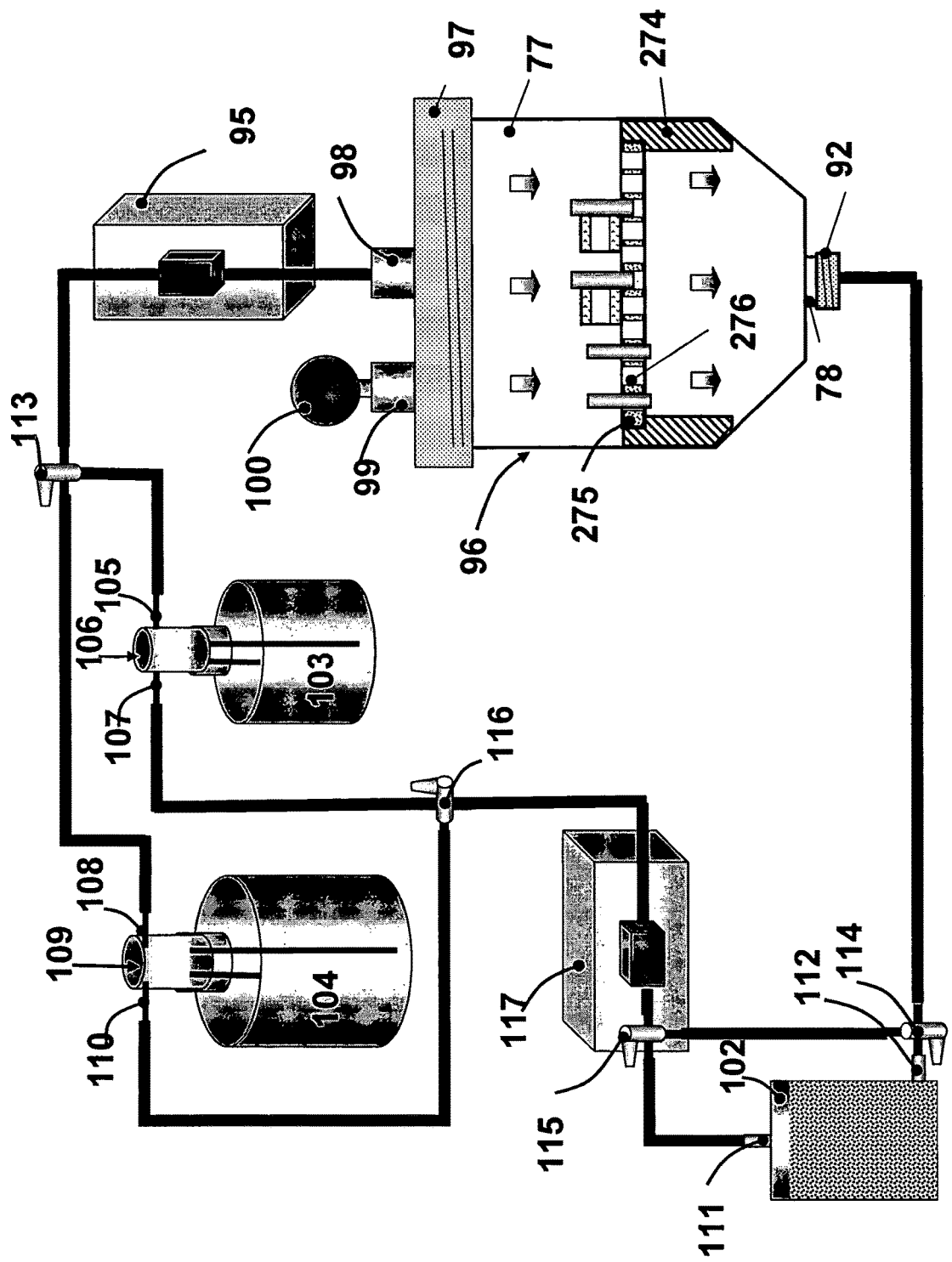
FIG. 16a illustrates a pressurized flow through devitalization system where fluids are recirculated between a cleaning/processing chamber (96) with an insert (274) and a reservoir.
Figure 16B:
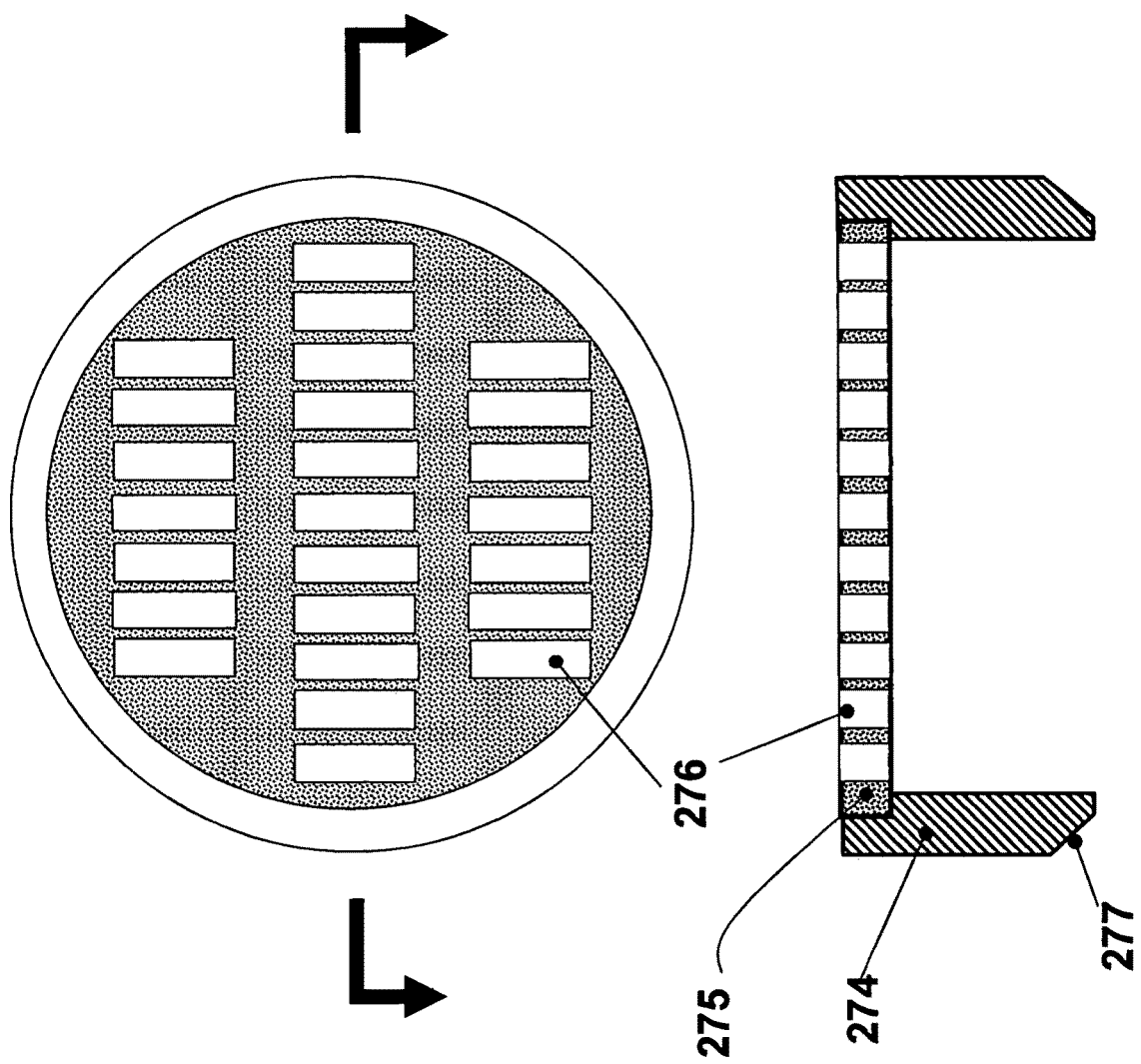
FIG. 16b illustrates a top and a side view of an insert (274) that the cartilage grafts are fitted in so that the superficial surface of the cartilage grafts are parallel to the fluid flow direction.

For devitalization in a fluid through system (FIG. 15 or FIG. 16a), osteochondral plugs, cartilage discs, cartilage slices, or cartilage flakes or curls can be loosely fit into an insert (101) that may be made of a porous material, such as porous titanium, stainless steel, or ceramics (FIG. 15). Fluid may be allowed to flow through and around the cartilage grafts. The superficial surface of the cartilage grafts can be perpendicular to the fluid flow directions as illustrated in FIG. 15. Alternatively, the cartilage grafts can be placed in an insert (274) with a porous plate (275) (FIG. 16a and FIG. 16b). The porous plate (275), made of a porous material, such as porous titanium, stainless steel, or ceramics, has slots that allow cartilage portion of the grafts to be fit into so that the fluid flow may be parallel to the superficial surface of the cartilage graft as illustrated in FIG. 16a.

In detail, FIG. 15 and FIG. 16a illustrate a system for processing cartilage grafts using a flow through system to circulate the pretreatment, extracting, rinsing, or storage solution between the processing chamber and the corresponding reservoir. The reservoir (103) can be interchangeably a pretreatment solution reservoir and an extracting solution reservoir. Moreover, the reservoir (104) can be interchangeably a rinsing solution reservoir or a storage solution reservoir. Cartilage grafts may be placed into the processing chamber (96) using a suitable insert (101 or 274) made of porous polymer, metal or ceramics. The insert (101 or 274), shown in FIG. 15 or FIG. 16a, can accommodate multiple grafts. The Luer lock (92) and the lid (97) may be screwed down tightly to engage the o-ring thereby eliminating leakage from the chamber (96). The hydrophobic adsorbent resin and anion exchange resin are optionally added to the resin chamber (102). There may be an o-ring at the top and bottom of the resin chamber to ensure a secure fit between the resin chamber and the resin housing to force the flow of rinsing solution through the resin chamber. Sterile medical grade disposable tubing may be attached to ports (110, 108, 78, 112, 111, 107, 105, 98), and with 3-way stop cocks (113, 114, 115, and 116) inserted in-line. The tubing may be attached to the sipper devices (106 and 109) such that the return flow enters the side with the shortest spout and the outbound flow may be pulled through the longest spout. The tubing may be placed onto the rollers of the peristaltic pumps (95 and 117) and the clamp lowered to hold the tubing in place. Once the rinsing or storage solution (104), pretreatment or the extracting solution (103) may be connected, all connections may be checked to ensure that they are tight. The pumps (95 and 117) may be turned on and their calibration is preferably checked. The pretreatment solution or the extracting solution may be drawn up from the long spout of sipper (106), proceeds through the port (105), continues past stopcocks (113) and tubing through the roller assembly of the pump (95) into the processing chamber (96) through port (98), proceeds through the cartilage graft and insert, then out the bottom of the chamber and through port (78) and continues past stopcocks (114 and 115), then into the sipper (106) through the short spout and port (107) by using a second pump (117). This cycle can be carried out at a flow rate preferably of from about 2 mls/minute to about 500 mls/minute, more preferably of from about 50 mls/minute to about 350 mls/minute, most preferably of from 150 mls/minute to about 250 mls/minute, at a temperature preferably of about 4 to about 45° C., more preferably of about 15 to about 37° C., and a period of time preferably of from about 1 hour to about 48 hours, more preferably of from about 1 hour to about 24 hours, and most preferably of from about 1 hour to about 16 hours. After the pretreatment and/or extraction, the pump (95) may be stopped and only pump (117) may be on until the processing chamber is empty. Stopcocks (113, 114, 115, and 116) may be turned to redirect the flow to and from the rinsing solution reservoir (104) and to optionally direct the flow through the resin housing chamber (102). The pumps (95 and 117) may be turned on again and the chamber may be filled by the rinsing solution, exiting sipper (108) out the long spout, into the tubing through stopcock (113), and through the roller pump (95), through the processing chamber (96) into the tissue chamber through port (98) and proceeds through the cartilage graft and insert, then out the bottom of the chamber and through port (78) and continues past stopcock (114) which directs the flow of the rinsing solution into the resin chamber (102) out port (111) and stopcocks (115 and 116) through the tubing and into sipper (109) via the short spout and port (110) and into the isotonic saline or water reservoir (104) by using a second pump (117). This washing cycle can be carried out at a flow rate preferably of from about 2 mls/minute to about 500 mls/minute, more preferably of from about 50 mls/minute to about 350 mls/minute, most preferably of from 150 mls/minute to about 250 mls/minute, at a temperature preferably of about 4 to about 45° C., more preferably of about 15 to about 37° C., and a period of time preferably of from about 1 hour to about 48 hours, more preferably of from about 1 hour to about 24 hours, and most preferably of from about 1 hour to about 16 hours. The pressure within the processing chamber can be monitored by a pressure gauge (100) that may be connected to a port (99). Then the rinsing solution in reservoir (104) may be replaced by a storage solution and the circulation can be carried out at a flow rate preferably of from about 2 mls/minute to about 500 mls/minute, more preferably of from about 50 mls/minute to about 350 mls/minute, most preferably of from 10 mls/minute to about 50 mls/minute, at a temperature preferably of about 4 to about 45° C., more preferably of about 15 to about 37° C., and a period of time preferably of from about 1 hour to about 48 hours, more preferably of from about 1 hour to about 24 hours, and most preferably of from about 1 hour to about 16 hours.

Figure 17B:
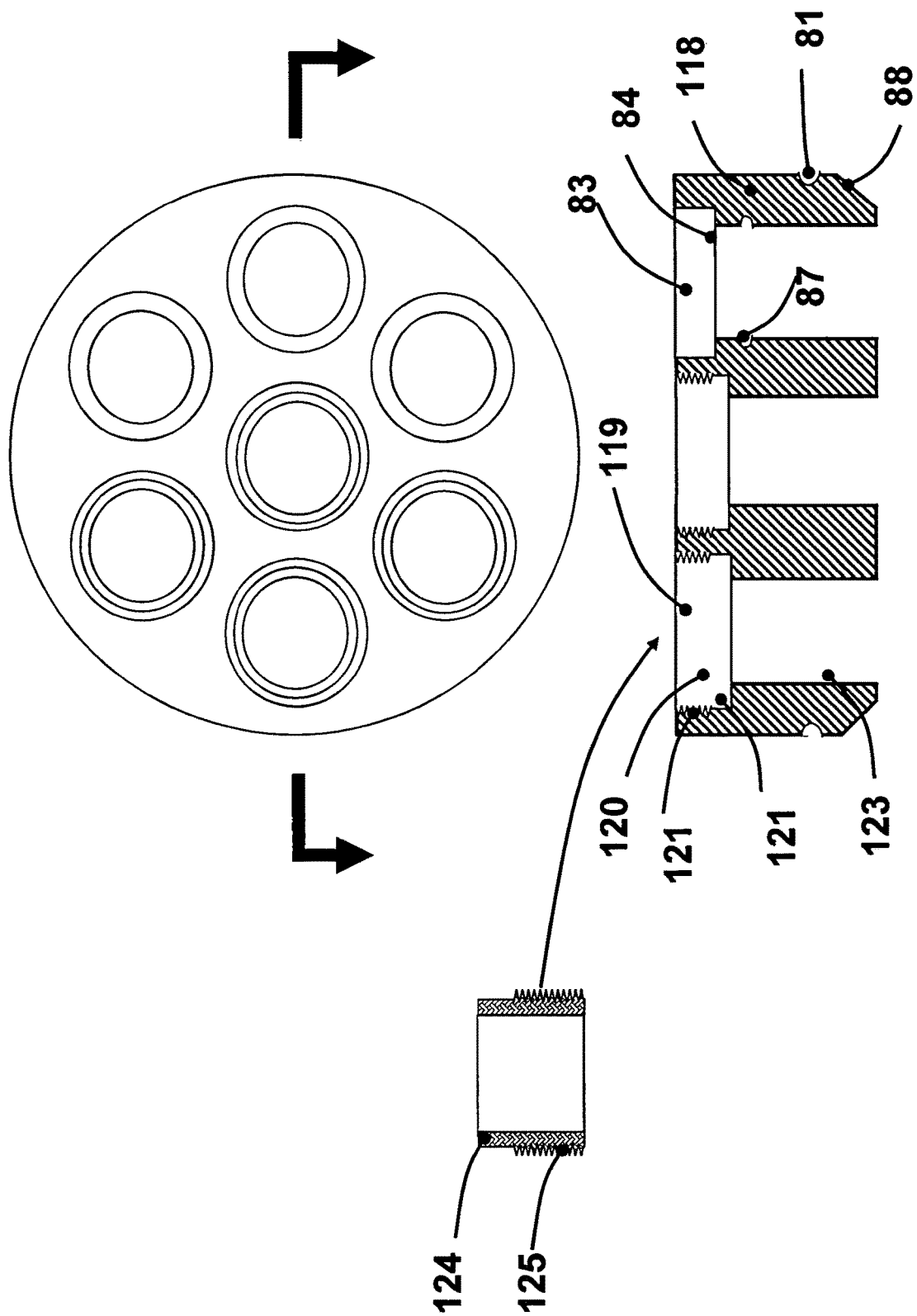
FIG. 17b illustrates a top and a side view of an insert (118) where a well (124) is interchangeable within the step cylindrical hole (119) to accommodate a different thickness of the cartilage disc or a stack of cartilage slices to create a contoured cartilage graft.

For devitalization under cyclic hydrodynamic pressure (FIG. 17a), cartilage grafts may be placed into the processing chamber (96) using a suitable insert (118), shown in FIG. 17b made of biocompatible polymers such as Teflon, or biocompatible metal such as titanium or stainless steel. The insert (118) can accommodate multiple grafts with different configuration, such as a stack of cartilage slices, cartilage disc, or osteochondral plug as illustrated in FIG. 17a. If desired, a cylindrical well (124) that has thread on the half of the outer surface may be threaded onto the top portion (120) of a step cylindrical hole (119). A porous platen (129) and an o-ring (130) may be fitted underneath of the well (124) so that fluid flow (if present) may be only allowed to go through the middle of the well (124). The cartilage discs or slices or cartilage flakes can be placed on the porous platen (129) within the well (124) as illustrated in FIG. 17a. The insert (118) and the well (124) may be made of the same material as the insert (80). If desired, the cartilage discs or thin slices of cartilage stacked together, as illustrated in FIG. 17a, can be placed between two contoured porous platens, which create curvature match the defect site in a joint. The hydrodynamic cyclic pressure can be driven by compressed air/gas to pressurize the pretreatment solution or the extracting solution or rinsing solution or storage solution within the processing chamber (96) to facilitate the processing. The Luer lock (92) and the lid (97) may be screwed down tightly to engage the O-ring thereby eliminating leakage from the chamber (96). The processing chamber can be filled with a processing solution. A pressurization chamber, composed of the bottom (282) and the top (285) parts, may be threaded together and separated by a fluid impermeable flexible membrane (284) and sealed by an o-ring (283). The pressurization chamber may be connected to an air/gas chamber (133) and a piston (132) through a connector (286). The bottom of the pressurization chamber may be filled with processing solution and connected with the processing chamber (96) through port (287) and rigid tubing. The compressed air/gas can be driven by a piston (132) and passes through the connector (286) to compress the flexible membrane (193). The piston can be driven by a computer controlled cam and/or stepper motor to move up and down to create a cyclic pressure on the flexible membrane that transfers the pressure to the processing chamber. The pressure can be monitored using two pressure gauges (100) and regulated by two valves (131), which may be connected to the rigid tubing. The compressed air/gas may be made of sterile 5% $CO_2$ in air.

During devitalization, the pretreatment solution may be transferred into the processing chamber, as well as the rigid tubing and the bottom part of the pressurization chamber (FIG. 17a). The cartilage grafts may be pre-treated with pretreatment solution under cycles of hydrodynamic pressure preferably of about −20 to about 20 MPa, more preferably about −10 and about 10 MPa, most preferably about −6 and about 6 MPa, at a frequency preferably of from about 0.01 to about 5 Hz, more preferably of from about 0.1 to about 2 Hz, and most preferably of from about 0.5 to about 1 Hz, at a temperature preferably of from about 4 to about 45° C., more preferably of from about 15 to about 37° C., and for a period of time preferably of from about 5 minutes to about 48 hours, more preferably of from 10 minutes to about 24 hours, most preferably of from about 30 minutes to about 16 hours The pretreatment solution in the processing chamber may be removed and replaced by a rinsing solution. The grafts can be pressurized again under cycles of hydrodynamic pressure preferably of about −20 to about 20 MPa, more preferably about −10 and about 10 MPa, most preferably about −6 and about 6 MPa, at a frequency preferably of from about 0.01 to about 5 Hz, more preferably of from about 0.1 to about 2 Hz, and most preferably of from about 0.5 to about 1 Hz, at a temperature preferably of from about 4 to about 45° C., more preferably of from about 15 to about 37° C., and for a period of time preferably of from about 5 minutes to about 48 hours, more preferably of from 10 minutes to about 24 hours, most preferably of from about 30 minutes to about 16 hours. After rinsing solution may be drained from the processing chamber, an extracting solution may be transferred into the processing chamber. The cartilage grafts can be processed under cycles of hydrodynamic pressure preferably of about −20 to about 20 MPa, more preferably about −10 and about 10 MPa, most preferably about −6 and about 6 MPa, at a frequency preferably of from about 0.01 to about 5 Hz, more preferably of from about 0.1 to about 2 Hz, and most preferably of from about 0.5 to about 1 Hz, at a temperature preferably of from about 4 to about 45° C., more preferably of from about 15 to about 37° C., and for a period of time preferably of from about 5 minutes to about 48 hours, more preferably of from 10 minutes to about 24 hours, most preferably of from about 30 minutes to about 16 hours. Following completion of the devitalization process, the processing chamber may be drained of the extracting solution and replaced with rinsing solution, such as water, saline, phosphate buffer saline, RPMI media, balanced Hank's solution, Lactated Ringer's solution, DMEM/F12, F12, or DMEM media. The cartilage grafts can be pressurized again under cycles of hydrodynamic pressure preferably of about −20 to about 20 MPa, more preferably about −10 and about 10 MPa, most preferably about −6 and about 6 MPa, at a frequency preferably of from about 0.01 to about 5 Hz, more preferably of from about 0.1 to about 2 Hz, and most preferably of from about 0.5 to about 1 Hz, at a temperature preferably of from about 4 to about 45° C., more preferably of from about 15 to about 37° C., and for a period of time preferably of from about 5 minutes to about 48 hours, more preferably of from 10 minutes to about 24 hours, most preferably of from about 30 minutes to about 16 hours. The rinsing solution may be replaced with a storage solution. The cartilage grafts can be pressurized again under cycles of hydrodynamic pressure preferably of about −20 to about 20 MPa, more preferably about −10 and about 10 MPa, most preferably about −6 and about 6 MPa, at a frequency preferably of from about 0.01 to about 5 Hz, more preferably of from about 0.1 to about 2 Hz, and most preferably of from about 0.5 to about 1 Hz, at a temperature preferably of from about 4 to about 45° C., more preferably of from about 15 to about 37° C., and for a period of time preferably of from about 5 minutes to about 48 hours, more preferably of from 10 minutes to about 24 hours, most preferably of from about 30 minutes to about 16 hours.

All the inserts (80, 101, 274, and 118) described above may be designed to be interchangeable among all the processing chambers (75 or 96) in all the devitalization methods. Osteochondral plugs or cartilage discs or slices or flakes or curls from the same donor can be fit into a single processing chamber.

If desired, as described above, after devitalization, the circumferential area of the cartilage graft, such as the cartilage portion of the osteochondral plug, or cartilage discs, or cartilage slices may be further crafted to maximize the surface and contact areas between the boundaries of the recipient cartilage being repaired and the cartilage graft, as illustrated in FIG. 5, to facilitate integration of the graft tissue to the recipient tissue.

Figure 18A:
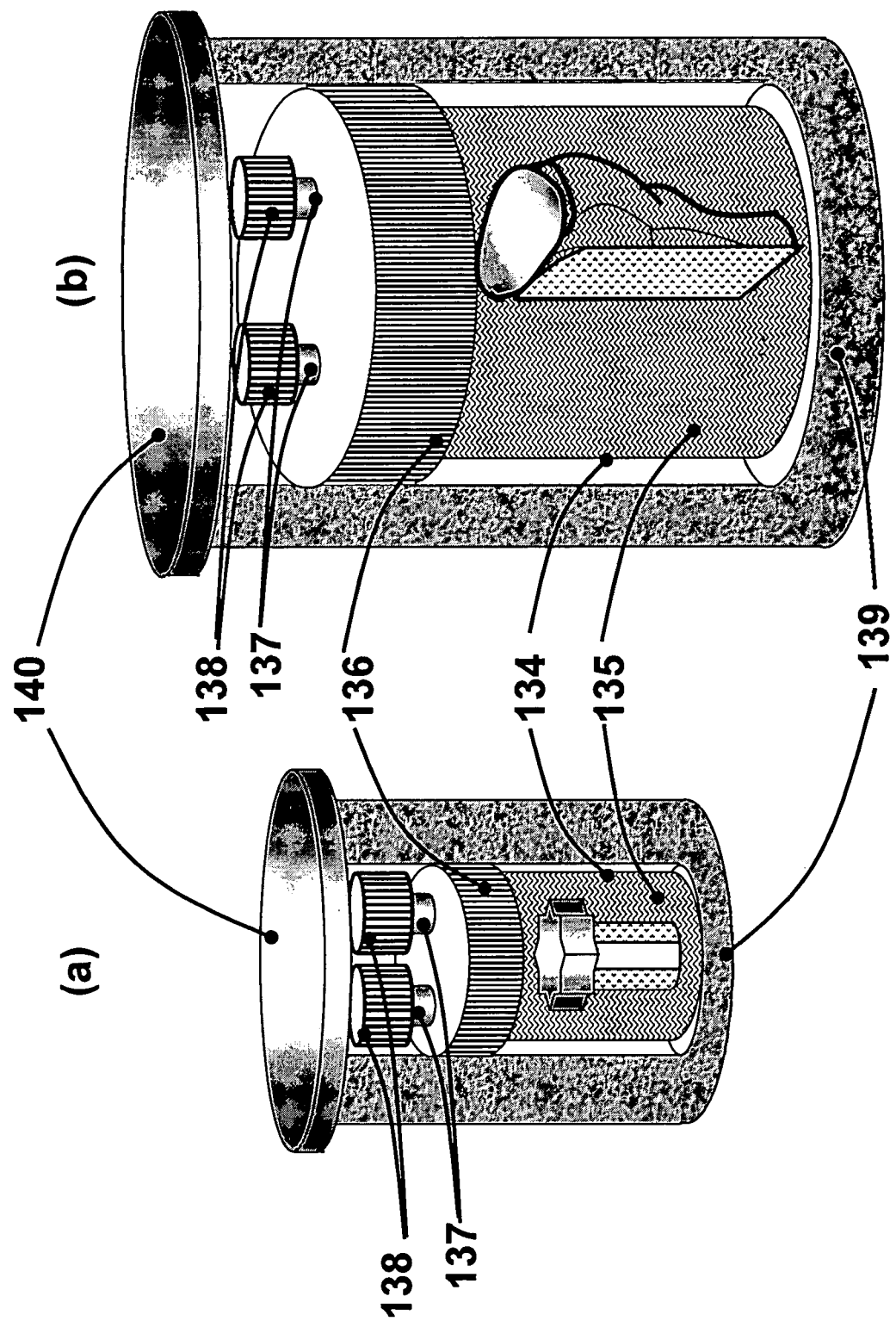
FIG. 18a illustrates an embodiment of a packaging device where cartilage grafts are immersed in a storage solution.

The cartilage grafts that have been crafted and devitalized as noted above can be stored in a plasticizer, such as 15-77% glycerol. Suitable storage solutions are well known to those of ordinary skill in the art to which the present invention applies, and such solutions may be readily selected and employed by those of ordinary skill in the art to which the present invention applies without undue experimentation. U.S. Pat. Nos. 6,544,289, 6,293,970, 6,569,200, and 7,063,726 directed toward the use of a water replacing agent for storage of bone and soft tissue. These patents are incorporated by reference in their entireties. After completion of the incubation with storage solution, in one embodiment, the cartilage grafts can be placed in an inner bottle (134) of varying size to accommodate a small (a) or a large graft (b) and completely immersed in the storage solution (FIG. 18a). The lid (136) of the inner bottle may be screwed down tightly to engage an o-ring thereby eliminating leakage from the bottle. The two ports (137 and 138) sealed with Luer lock caps on the lid (136) can be used for a future rinsing step in the operating room. The inner bottle may be then placed in an outer container (139) made of foam material that functions as a cushion if impact force applies. The entire package can be sealed with a lid (140). Alternatively, storage solution soaked grafts can be spun quickly to remove excessive storage fluid and packaged in double containers as illustrated in (c-e) in FIG. 18b. The cartilage grafts can be placed in an inner sealed box (141) then the inner box may be placed in an outer box (143) and sealed (c in FIG. 18b); or placed in an inner bag (145) with two ports (147), sealed under vacuum on one edge (146), placed in an outer bag, and sealed (d and e in FIG. 18b). Depending on the size of the grafts, the inner bag (145) can be large enough to accommodate a whole condyle as illustrated in (d in FIG. 18b) or small enough to fit an osteochondral plug as illustrated in (e in FIG. 18b). The two ports (147) sealed with Luer lock caps (148) on the sealed edge (146) can be used for a future rinse step in the operating room. The grafts in the storage containers described above may be terminally sterilized using methods known in the art including, but not limited to, gamma irradiation. Alternatively, the devitalized cartilage grafts may be terminally sterilized with super critical $CO_2$ or ethylene oxide before soaked in the sterile storage solution and packaged in a sterile field.

The devitalized cartilage grafts as shown in FIG. 1-FIG. 6 can be optionally modified to stimulate in vivo, in situ, and/or in vitro infiltration of the viable cells, such as chondrocytes from cartilage tissue or stromal cells from bone marrow or synovium. In one embodiment, after devitalization and washing, the cartilage graft can be coated with one or more agent(s) that has bioactive growth supplement or cytokine binding site(s) through covalent coupling or adsorption to increase the affinity of a bioactive growth supplement or cytokine to the devitalized graft. The agent(s) that has bioactive growth supplement or cytokine binding site(s) can be one or a combination of extracellular matrix proteins. The agent(s) that has bioactive growth supplement or cytokine binding site(s) can be a natural or synthetic molecule. Moreover, the agent may comprise an extra functional moiety that may be selected from a group, but not limited to, COOH, NH2, or OH can be added to the natural or synthetic proteins or peptides to facilitate the coating. The extra functional moeity can be from groups that change the hydrophilicity or charge. After being coated with one or more agent(s) that has bioactive growth supplement or cytokine binding site(s), the cartilage graft as a whole unit can be further soaked with one or more bioactive growth supplements or cytokines. The cartilage portion and the bone portion (if present) of a cartilage graft can be treated at the same time with the same bioactive growth supplements. Alternatively, the cartilage portion and the bone portion of a cartilage graft can be treated separately, e.g., the cartilage portion may be soaked into one or more than one chondrogenic factor(s) and the bone portion may be soaked into one or more than one osteogenic factor(s). In addition, in order to facilitate the binding of the bioactive growth supplement or cytokines to the cartilage graft, a solution with one bioactive growth supplement or cytokines, or a cocktail of bioactive growth supplements or cytokines can be added into the top and/or bottom portion of the processing chamber (75 or 96). Under centrifugal force, or vacuum pressure, or a pressure induced fluid flow, or a cyclic pressurization, the bioactive growth supplements or cytokines can be induced to migrate into the cartilage graft. Alternatively, microparticles can also be conjugated with a bioactive growth supplement or a cytokine and forced into the devitalized cartilage using centrifugal forces between 50 and 2000 rcf, preferably between 100 and 1800 rcf, and more preferably between 500 and 1500 rcf. The microparticles can be from a group of, but not limited to, demineralized bone matrix, freeze dried and ground soft tissue, such as submucosa, fascia, muscle, dermis, cartilage, or amionic membrane. The microparticles can also be microbeads made of biocompatible natural or synthetic polymers, such as collagen, chitosan, alginate, agarose, or hyaluronic acid. The bioactive growth supplements may be one or more of, a natural or recombinant FGF-family, TGF-family, IGF-1, PDGF, EGF, VEGF, HGF, PTHrP, Ihh, dexamethasone, insulin, transferrin, selenium, ITS, or ascorbate. The bioactive growth supplements can also be from the extractions of demineralized bone matrix, basement membrane, or submucosa matrix. The cytokines may be one or more of, for example, an IL-1αR antibody, TNF-a receptor antagonist, cyclooxygenase-2 specific inhibitors, MAP kinase inhibitors, NO synthase inhibitors, NF-κB inhibitors, and inhibitors of MMP.

Figure 19:
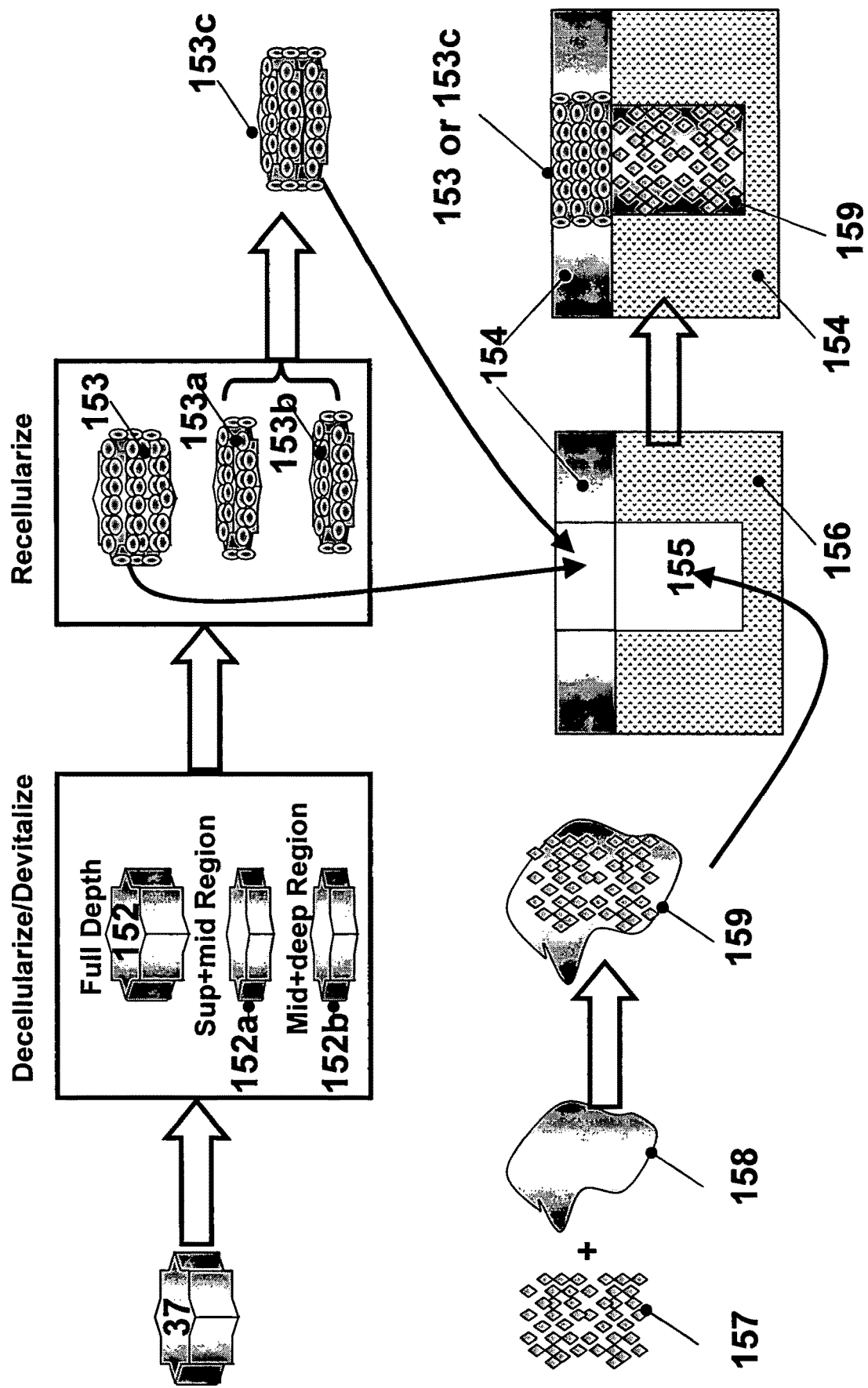
FIG. 19 illustrates an enlarged view of a procedure of recellularization of the cartilage discs or slides in situ and implantation of the recellularized cartilage graft with a filler to form a composite graft to repair an osteochondral defect.

The devitalized cartilage graft is intended to be recellularized in situ, in vitro, or in vivo. The devitalized cartilage graft can be removed from the storage container, rinsed, and diluted using an AlloFlow™ chamber among others. Such a chamber is disclosed in U.S. Pat. Nos. 5,879,876 and 6,326,188, which are incorporated by reference in their entireties herein. In one embodiment, the devitalized cartilage graft can be recellularized in situ. The devitalized cartilage graft can be implanted in a cartilage defect in a recipient to render cells from the recipient tissue to migrate into the devitalized cartilage graft, proliferate, differentiate, and secrete endogenous extracellular matrix. In order to facilitate the in situ recellularization, chemical stimuli can be optionally applied. The chemical stimuli can be to coat a devitalized cartilage graft with one or more agent(s) that have bioactive growth supplement or cytokine binding site(s) to increase the affinity of chondrogenic and/or osteoinductive factor adsorption onto the devitalized graft. The chemical stimuli can also be micro-particles that are conjugated with cytokines or bioactive growth supplements and sprayed or blasted onto the cartilage graft before implantation. Alternatively, for in situ recellularization, the devitalized grafts can be recellularized by seeding recellularizable cells, for example, cells isolated from autologous or allogenous soft tissue or bone marrow and/or cultured previously, on to the cartilage graft right before implantation. FIG. 19 illustrated the procedure of rendering recellularization of a cartilage disc or two parts of the cartilage disc from superficial-mid or mid-deep region and implanting the recellularized cartilage grafts into the defect site. The cartilage disc (shown with star shape) with full depth (152) or cut from superficial and mid zone (152a) or from mid and deep zone (152b) along the depth may be cleaned, disinfected, devitalized, and/or stored. Prior to implantation, the cartilage discs may be rinsed with isotonic saline using an AlloFlow™ chamber. Recellularizable cells isolated from autologous or allogenous sources can be seeded on the devitalized cartilage discs immediately before implantation. Optionally, a centrifugal force or a positive pressure can be applied to facilitate cell adhesion onto the devitalized cartilage graft. The devitalized cartilage disc can be recellularized with one or more than one type of cells from recellularizable cells. If desired, the superficial and mid zone cartilage (152a) can be seeded with chondrocytes from the superficial region, while the mid and deep zone cartilage (152b) can be seeded with chondrocytes from the mid to deep region. During surgery, the blind bore (155) in the bone portion (156) of the cartilage defect can be filled with a bone filler that may be a mixture of a matrix (157) with or without a carrier (158). U.S. Pat. No. 6,340,477, and U.S. patent application Ser. Nos. 11/247,230, 11/247,229, and 11/247,249, which are incorporated by reference in their entireties herein, are directed towards the use of DBM combined with carriers that may be hydrogel, synthetic or biological polymers to form a malleable bone putty or flowable gel for filling bone defects. The matrix in the bone filler may be one or more of, for example, autologous crushed bone harvested from the defect site; demineralized bone matrix; cancellous and cortical bone mixture; small intestine submucosa, amniotic membrane, ligament, tendon, skin, muscle tissue, periostieum, or synovial tissue; ceramics; hydroxyapatite; calcium phosphate; calcium sulfate; porous surgical grade titanium or stainless steel; or any combination of the above. The matrix can be in the format of a sheet, a disc, a tape, a sponge, a cube, a solid or hollow cylinder, gel, putty, or particles. The carrier may be one or more of, for example, dihydroxyphenylalanine (DOPA) based adhesive, glucose, concentrated albumin, cyanoacrylate adhesive, gelatin-resorcin-formalin adhesive, chondroitin sulfate aldehyde N-acetylglucosamine (GlcNAc), mussel-based adhesive, poly(amino acid)-based adhesive, cellulose-based adhesive, synthetic acrylate-based adhesives, platelet rich plasma (PRP), monostearoyl glycerol co-Succinate (MGSA), monostearoyl glycerol co-succinate/polyethylene glycol (MGSAPEG) copolymers, or a combination comprising at least one of the foregoing polymers. The carrier can also be one or more of, for example, native or modified collagen, gelatin, agarose, modified hyaluronic acid, fibrin, chitin, biotin, avidin, native or crosslinked chitosan, alginate, demineralized bone matrix, MATRIGEL®, HUMAN EXTRACELLULAR MATRIX®, homogenized connective tissue, proteoglycans, fibronectin, laminin, fibronectin, elastin, heparin, glycerol, or a combination comprising at least one of the foregoing polymers. The carrier may include bioactive growth supplements such as FGF-family, TGF-family, IGF-1, PDGF, EGF, VEGF, HGF, PTHrP, Ihh, dexamethasone, insulin, transferrin, selenium, ITS, or ascorbate. The carrier may also include bioactive growth supplements from the extractions of demineralized bone matrix, basement membrane, or submucosa matrix. The carrier may include cytokines, for example, an IL-1αR antibody, TNF-a receptor antagonist, cyclooxygenase-2 specific inhibitors, MAP kinase inhibitors, NO synthase inhibitors, NF-κB inhibitors, or inhibitors of MMP. Moreover, the carrier may also include one or more than one type of cells from recellularizable cells. The bone filler may also be a cortical and/or cancellous bone plug. After the blind bore (155) in the bone portion may be filled with a bone filler to provide a support, the recellularized cartilage disc, either full depth (153) or a stack of cartilage slices from different zones (153a and 153b) to form a full depth cartilage (153c), can be tight-fit into the blind bore (155) of the cartilage portion (154) of the defect site.

If the defect site that needs to be repaired has a curvature, the cartilage graft can be contoured to match the curvature. FIG. 20 illustrates one of the methods to create a contoured graft in situ, wherein a cartilage disc (6) can be tailored into thin slices of varying thickness and diameters (127a-127c), stacked, and implanted. If recellularization is needed, cells can be seeded on the devitalized cartilage slices in situ, i.e., immediately before stacking and implantation. Alternatively, the cartilage discs and/or slices may be recellularized in vitro, i.e., seeded with cells, stacked, and cultured in a bioreactor to allow cell attachment, infiltration, proliferation, and/or differentiation. Nonetheless, the cartilage discs and/or slices can be recellularized in vivo, i.e., implanted in soft tissue, such as muscle pouch or fat pad or other tissue with progenitor or stromal cells, retrieved after about 7 days to about 3 month, and implanted. The devitalized cartilage slices can be recellularized with one or more than one type of cells from recellularizable cells. If desired, the superficial and mid zone cartilage (152a) can be seeded with chondrocytes from the superficial region, and the mid and deep zone cartilage (152b) can be seeded with chondrocytes from the mid to deep region. The cartilage slices can be optionally bonded between adjacent slices using one or more than one bonding agents. In one embodiment, during surgery, a step cylindrical osteochondral plug (30) with a flat superficial surface and gaps in the bone portion can be fit into the blind bore (155) first. The gaps or a bore or channels or slots in the bone portion of the osteochondral plug (30) can be filled with a bone filler that may be a mixture of a matrix (157) with or without a carrier (158) as described in FIG. 19. The bone portion of the osteochondral plug can be tightly fit into the bone portion of the blind bore (155). Alternatively, the bone portion of the osteochondral plug can be loosely fit into the bone portion of the blind bore (155). The clearance between the bone portion of the osteochondral plug and the blind bore (155) can be filled with the same bone filler as in the gaps or a bore or channels or slots on the bone portion of the osteochondral plug. The cartilage portion of the osteochondral plug can be tight-fit into the blind bore (155) of the convex cartilage portion (161) of the defect site. Ideally, the osteochondral plug fit in the defect site may be slightly lower than the surrounding recipient tissue so that the thin cartilage slices (127a-127c) can be stacked on top of the osteochondral plug to match the overall contour of the joint. Alternatively, during surgery, the blind bore (155) in the bone portion (156) of the cartilage defect can be filled with bone filler that may be a mixture of a matrix (157) with or without a carrier (158) as described in FIG. 19. The cartilage slices with (160) of without recellularization and with varying diameters can be stacked and tight-fit into the cartilage portion (161) of the blind bore (155) at the defect site to match the overall contour of the joint.

In one embodiment, if desired, the cartilage matrix, such as osteochondral plugs, cartilage discs, slices, or flakes or curls can be recellularized in vitro and cultured optionally under chemical and mechanical stimuli for about 1 day to about 40 days to create a viable coherent, contoured, and functional cartilage graft before implantation. The chemical stimuli during the in vitro recellularization and cultivation can be applied by adding one or a cocktail of bioactive growth supplements in the culture media. Alternatively, the chemical stimuli can be applied by coating the devitalized cartilage with one or more agent(s) that has bioactive growth supplement or cytokine binding site(s) through covalent coupling or adsorption to increase the affinity of a bioactive growth supplement or cytokine to the devitalized graft as illustrated previously. Furthermore, chemical stimuli can be applied by sprayed or blasted micro-particles onto the circumferential surface of the devitalized cartilage graft before recellularization. The microparticles may be, but are not limited to, demineralized bone particles; or freeze dried and ground submucosa, fascia, muscle, dermis, or cartilage. The microparticles can also be microbeads made of natural or synthetic materials that are conjugated with cytokines or bioactive growth supplements. The bioactive growth supplements may be one or more of, for example, a natural or recombinant FGF-family, TGF-family, IGF-1, PDGF, EGF, VEGF, HGF, PTHrP, Ihh, dexamethasone, insulin, transferrin, selenium, ITS, or ascorbate. The bioactive growth supplements can also be from extractions of demineralized bone matrix, basement membrane, or submucosa matrix. The cytokines may be, but are not limited to, one or more of, an IL-1αR antibody, TNF-a receptor antagonist, cyclooxygenase-2 specific inhibitors, MAP kinase inhibitors, NO synthase inhibitors, NF-κB inhibitors, or inhibitors of MMP.

Figure 21:
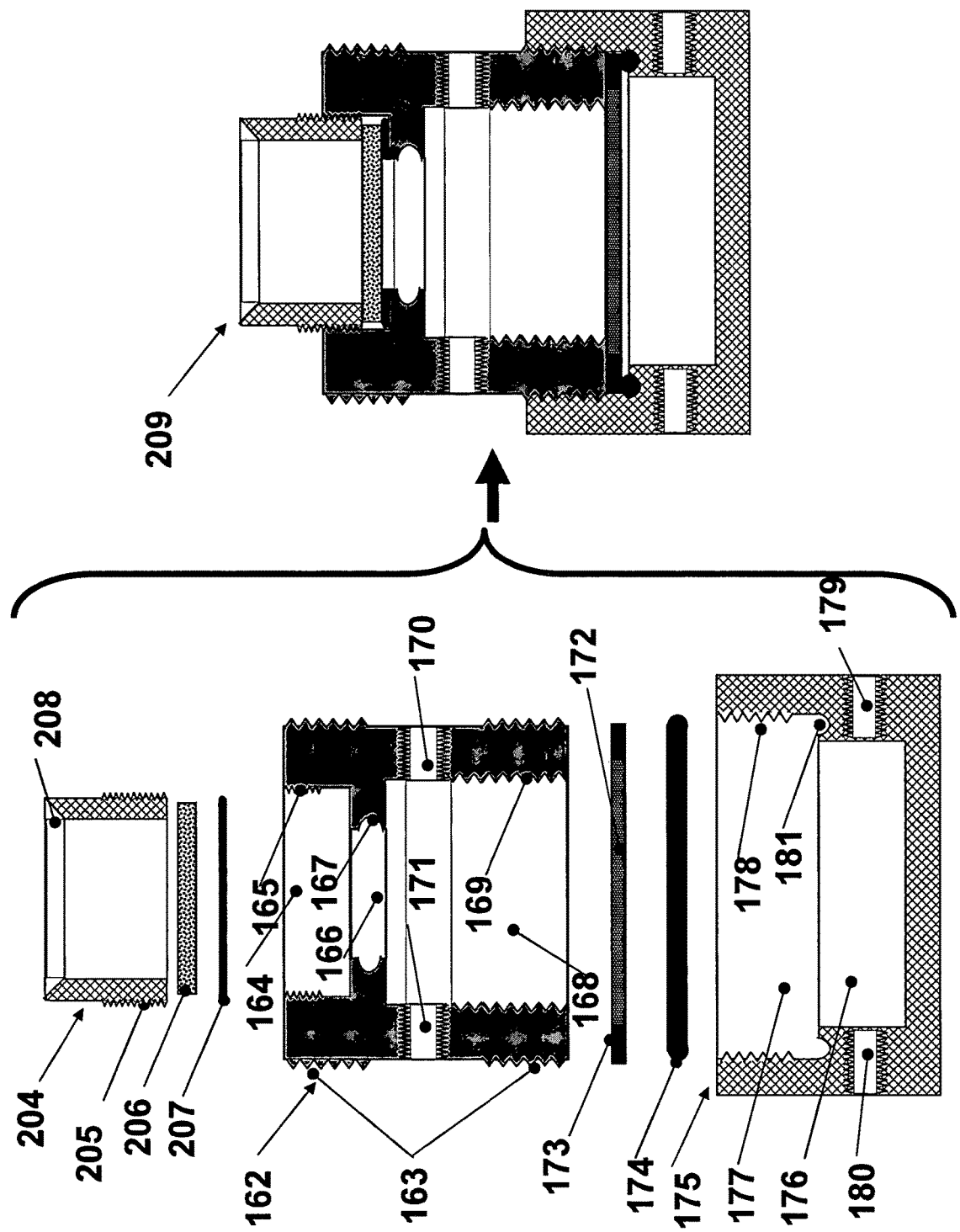
FIG. 21 illustrates the components of a bioreactor. The components are assembled to become the bottom chamber of a bioreactor for in vitro recellularization and cultivation of a devitalized cartilage graft.
Figure 22:
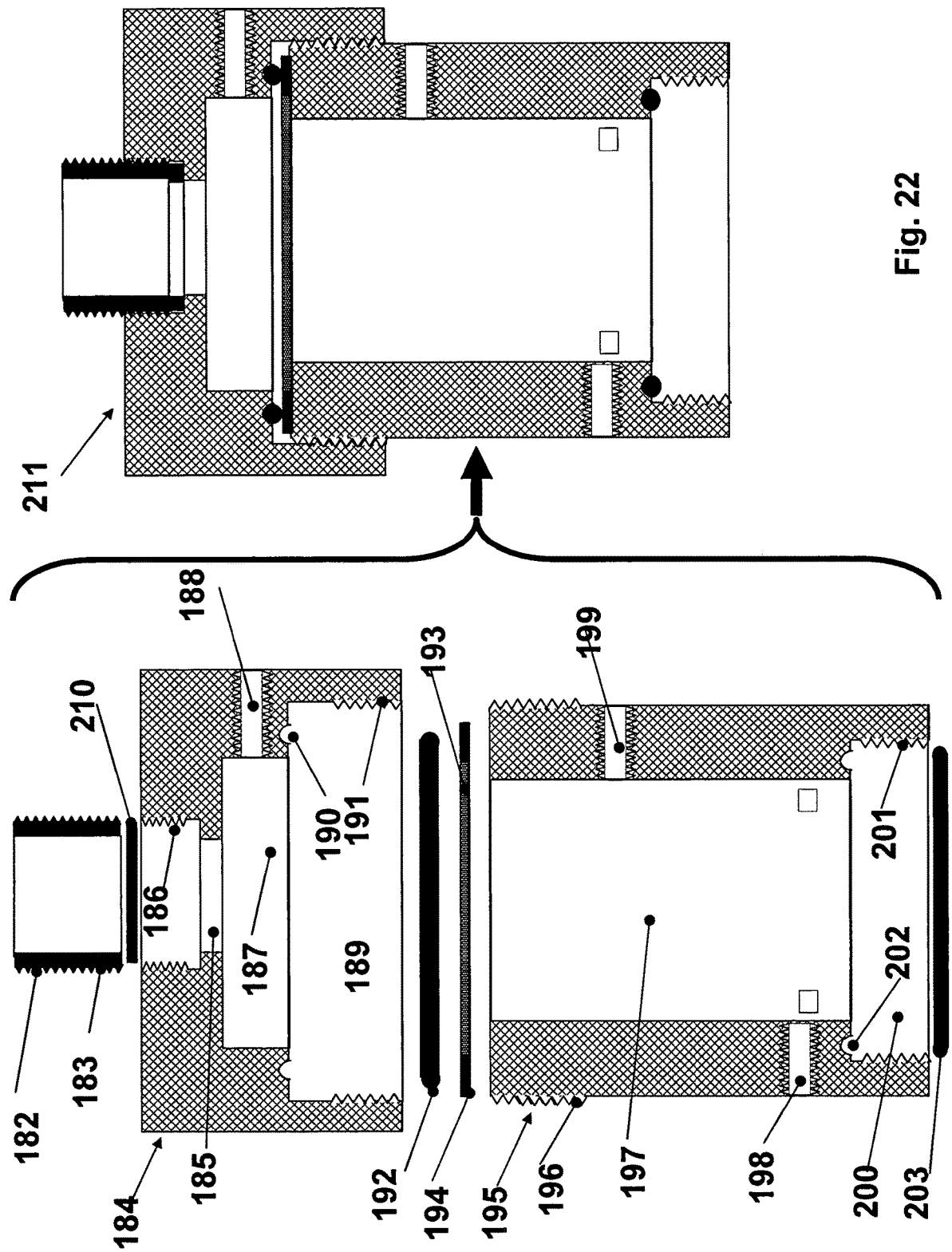
FIG. 22 illustrates the components of a bioreactor. The components are assembled to become the top portion of a chamber of a bioreactor for in vitro recellularization and cultivation of a devitalized cartilage graft.
Figure 23:
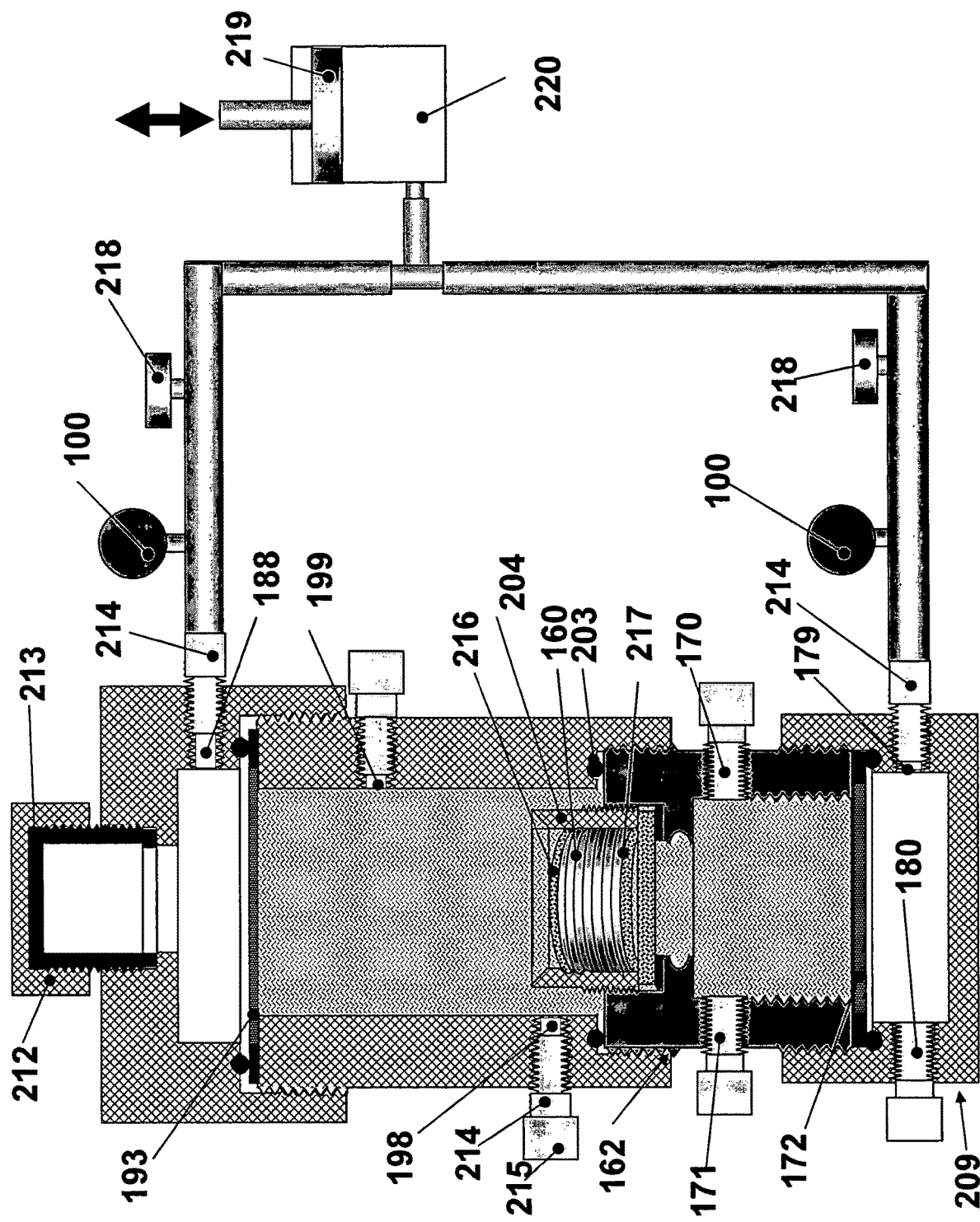
FIG. 23 illustrates a bioreactor assembly where sterile filtered air is compressed cyclically towards two gas permeable flexible membranes (193 and 172), which induce pressure on a cartilage graft sandwiched between two porous platens within a confining ring in a bioreactor filled with culture media.

The mechanical stimulus may be applied using a bioreactor. The components of a bioreactor that can provide various modes of mechanical stimuli are illustrated in FIG. 21 and FIG. 22. FIG. 21 illustrates the components that can be assembled to become the bottom portion of a chamber of a bioreactor for in vitro recellularization and cultivation of devitalized cartilage grafts. Three major components, i.e., the bottom cylindrical well (175), the cylindrical culture well (162), and the cylindrical confining ring (204) can be assembled together to comprise the bottom assembly (209). As illustrated, the top hole (177) of the bottom well (175) may be threaded so that the threaded outer surface (163) of the culture well (162) can be screwed into the top hole (177). A groove (181) may be also created at the bottom of the top hole (177) so that an O-ring (174) can be fit into. The culture well (162) may be screwed down into the top hole (177) of the bottom well (175) to engage the O-ring (174) thereby eliminating leakage from the chamber. If the mechanical stimulus may be driven by a compressed air/gas as illustrated in FIG. 23, a gas permeable and water impermeable membrane (172) that can be fixed in a ring fixture (173) can be assembled between the culture well (162) and the o-ring (174). The ports (179 and 180) on the bottom well and the ports (170 and 171) on the culture well (162) can be used for either fluid or gas exchange, or media sample collection during culture. A confining ring (204) may be screwed down to the threaded hole (164) of the culture well (162) to engage the porous platen (206) and o-ring (207) thereby forcing the culture media if present to flow though only in the middle of the confining ring during mechanical simulation.

Figure 24:
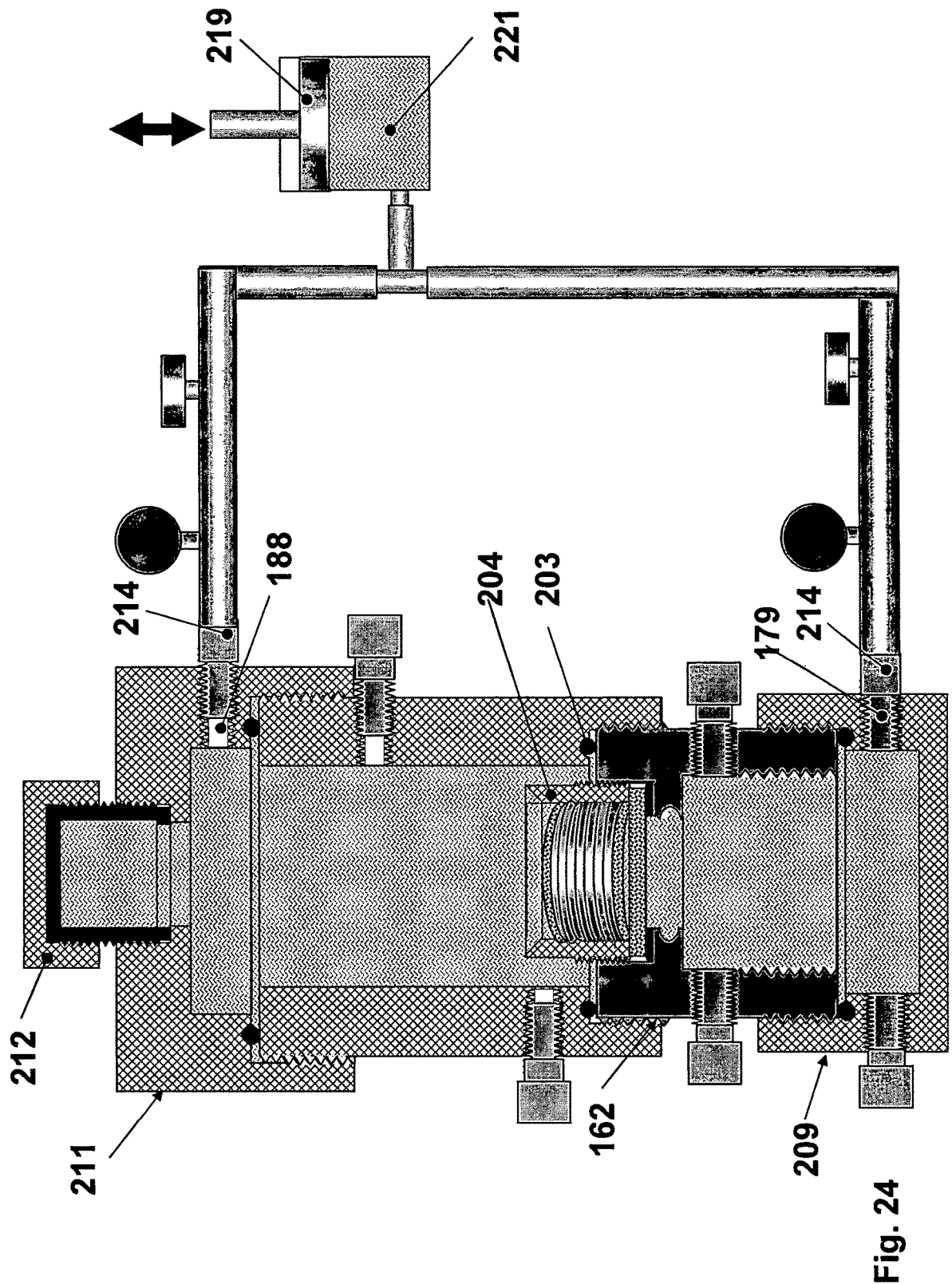
FIG. 24 illustrates a bioreactor assembly where fluid within the bioreactor is pressurized cyclically to induce pressure on a cartilage graft sandwiched between two porous platens within a confining ring in a bioreactor filled with culture media.
Figure 25:
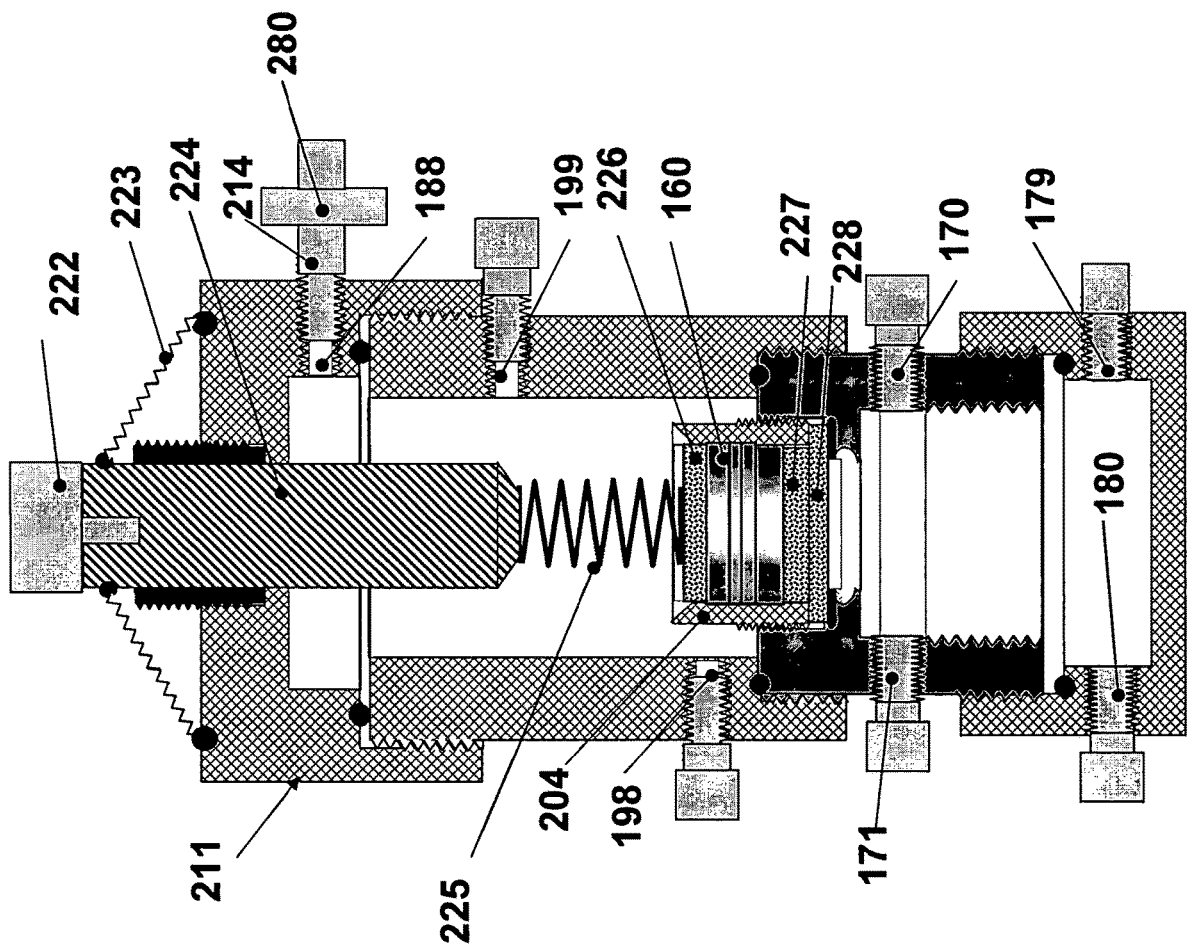
FIG. 25 illustrates a bioreactor assembly wherein a cartilage graft sandwiched between two porous platens within a confining ring is compressed with a compression shaft connected to a damping spring.
Figure 28:
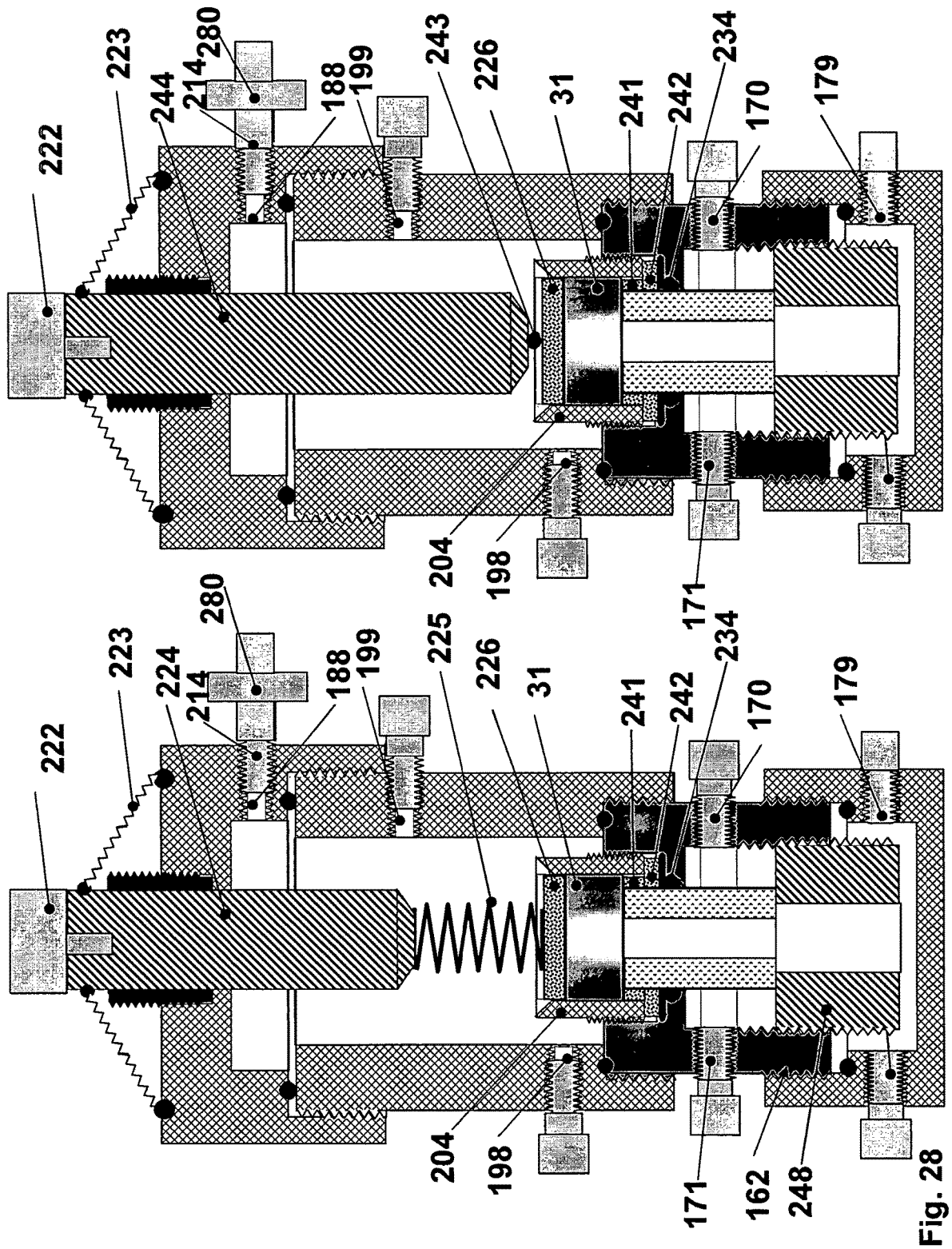
FIG. 28 illustrates a bioreactor assembly wherein a cartilage cap of an osteochondral plug is sandwiched between two porous platens within a confining ring and is compressed with a compression shaft with or without a damping spring connected.
Figure 29:
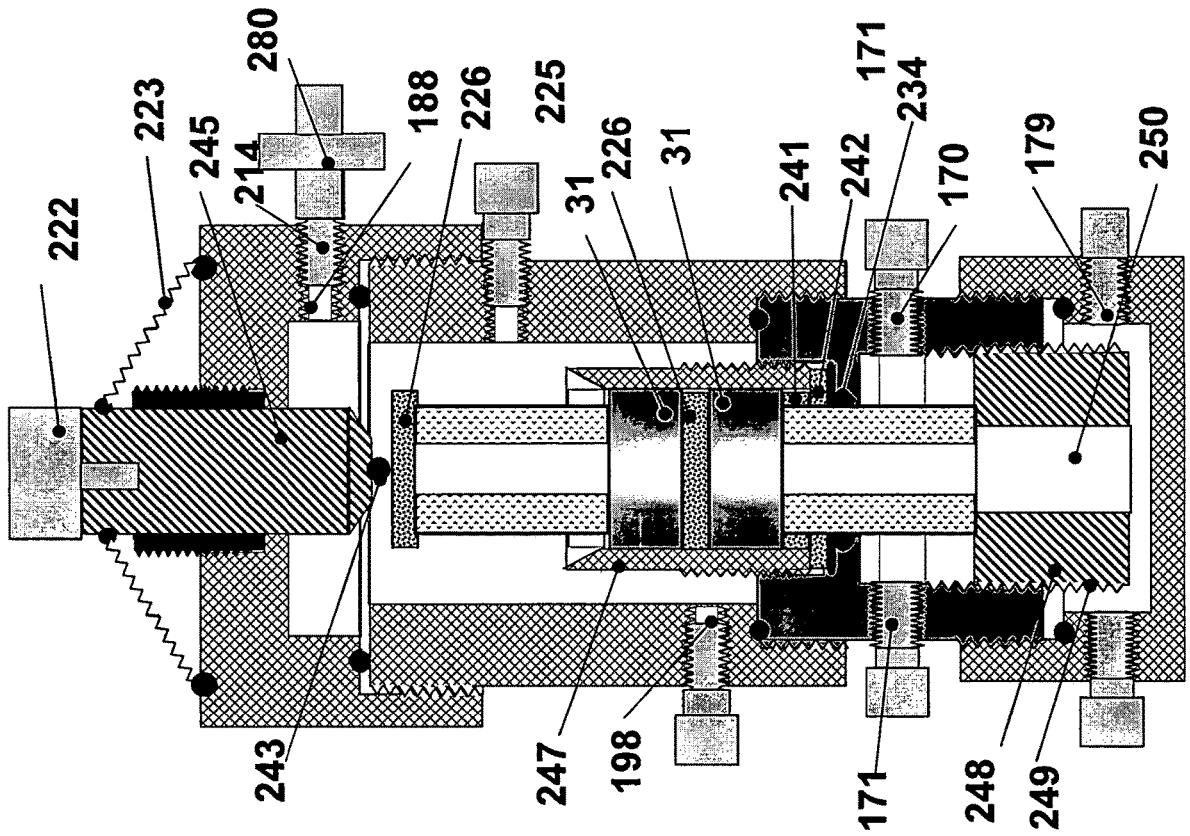
FIG. 29 illustrates a bioreactor assembly wherein the cartilage caps of two osteochondral plugs are placed opposite each other within a confining ring and are compressed with a compression shaft.

FIG. 22 illustrates the components that can be assembled to become the top portion of the chamber of a bioreactor for in vitro recellularization and cultivation of devitalized cartilage. Three major components, i.e., a cylindrical bushing (182), a cylindrical top cover (184), and a cylindrical top well (195) can be assembled together to comprise the top assembly (211). The bushing (182) can be used as a guidance when a loading shaft (224) may be placed in the middle for confined or unconfined compression tests as illustrated in FIG. 25, FIG. 28, and FIG. 29. If the mechanical stimulation does not involve a loading shaft as illustrated in FIG. 23 and FIG. 24, the bushing (182) can be sealed with a cap (212). A groove (190) may be created at the top of the threaded hole (189) in the top cover (184) so that an o-ring (192) can be fit into. The top well (195) may be screwed into the threaded hole (189) in the top cover (184) to engage the o-ring (192) thereby eliminating leakage from the chamber. If the mechanical stimulus may be driven by a compressed air/gas as illustrated in FIG. 23, a gas permeable and water impermeable membrane (193) that may be fixed in a ring fixture (194) can be assembled between the top well (195) and the O-ring (192). The ports (198 and 199) on the top well (195) and the port (188) on top cover (184) can be used for either fluid or gas exchange independent of that in the bottom assembly (209). After the bottom assembly (209) and the top assembly (211) may be assembled independently, cartilage grafts can be loaded into a culture well (162) with of without a confining ring (204). Then the top assembly may be screwed down onto the bottom assembly to engage the o-ring (203) thereby eliminating leakage from the entire chamber as illustrated in FIG. 23-FIG. 30.

FIG. 23 illustrates the application of mechanical stimulation by inducing compressive air/gas towards two flexible membranes (172 and 193) that induce pressure on a cartilage graft sandwiched between two porous platens (216 and 217) in a bioreactor filled with culture media. The cartilage grafts may be, but are not limited to, cartilage slices as illustrated in FIG. 23, or cartilage discs, or osteochondral plugs. The compression can be unconfined or confined. For confined compression as illustrated in FIG. 23, the cartilage slices can be seeded with cells first, stacked together, and sandwiched between two porous platens (216 and 217) in the confining ring (204). Recellularizable cells isolated from autologous or allogenous sources may be seeded on the devitalized cartilage grafts. Optionally, a centrifugal force or a positive pressure can be applied to facilitate cell adhesion onto the devitalized cartilage graft. The devitalized cartilage grafts can be recellularized with one or more than one type of cells from recellularizable cells. The porous platens can be flat or with a curvature that can create a contour on the cartilage graft to match the contour of the defect site to be repaired in the recipient. The bottom porous platen (217) can have the same curvature as the top porous platen (216) or can be flat. The porous platen can be made of a group of materials such as titanium, stainless steel, biocompatible polymers, ceramics, hydroxyapatite, calcium phosphate, calcium sulfate, cancellous bone, or cortical bone.

The compressed air/gas can be driven by a piston and passes through port (188) through a Luer lock tubing connection (214) to compress the flexible membrane (193). Meanwhile, the compressed air/gas can also pass through port (179) through a Luer lock tubing connection (214) to compress the flexible membrane (172). The piston can be driven by a computer controlled cam and/or stepper motor to move up and down to create a cyclic compression within the bioreactor. The pressure can be monitor using two pressure gauges (110) and regulated by two valves (218). The compressed air/gas may be made of sterile 5% $CO_2$ in air. The bioreactor may be able to fit into an incubator connected to one or two media reservoirs through ports (198, 199, 180, or 179). The cyclic compression can be carried out at pressure preferably of about 0 to about 20 MPa, more preferably of about 0 and about 10 MPa, most preferably of about 0 and about 6 MPa, at a frequency preferably of from about 0.001 to about 5 Hz, more preferably of from about 0.1 to about 3 Hz, and most preferably of from about 0.1 to about 1 Hz, for a period of time preferably of from about 5 minutes to about 16 hours, more preferably of from 5 minutes to about 8 hours, most preferably of from about 5 minutes to about 4 hours every day, and for a total duration preferably of 1 to about 40 days, more preferably of 1 to about 28 days, most preferably of 1 to about 14 days. Alternatively, the cyclic compression can be conducted by inducing compression on the culture media directly to induce pressure on a cartilage graft sandwiched between two porous platens (216 and 217) with or without a confining ring (204) in a bioreactor filled with culture media as illustrated in FIG. 24. At the end of cultivation, the viable coherent stack of cartilage slices or cartilage disc can be implanted along with or without the bottom porous platen (217).

FIG. 25 illustrates the application of the mechanical stimulation by inducing compressive stress using a load shaft (224) on a cartilage graft sandwiched between two porous platens. The compression can be confined or unconfined compression. The compression can also be carried out under compressive stress control or displacement control. A spring (225) can be serially connected to the bottom of the load shaft (224) to allow larger range and better control of the movement of the loading shaft during loading. The end of the spring can be flat and fixed onto the top porous platen (226). The cartilage slices or discs can be seeded with recellularizable cells, stacked together, and sandwiched between two porous platens (226 and 227) in the confining ring (204). Recellularizable cells isolated from autologous or allogenous sources can be seeded on the devitalized cartilage grafts before the application of mechanical stimuli. Optionally, a centrifugal force or a positive pressure can be applied to facilitate cell adhesion onto the devitalized cartilage graft. The devitalized cartilage grafts can be recellularized with one or more than one type of cells from recellularizable cells. The porous platens can be flat or with curvature that can create a contour on the cartilage graft to match the contour of the defect site to be repaired in the recipient. The bottom porous platen (227) can have the same curvature as the top porous platen (226) or can be flat. The porous platen can be made of a group of materials such as titanium, stainless steel, biocompatible polymers, ceramics, hydroxyapatite, calcium phosphate, calcium sulfate, cancellous bone, or cortical bone. The loading shaft can be driven by a computer controlled cam and/or stepper motor to move up and down to create a cyclic compression within the bioreactor. The compressive stress can be monitored with a load cell (222) and the strain of the loading may be adjusted to obtain the target stress. A flexible bellow (223) can be assembled between the top of the loading shafts (224) and the top chamber assembly (211) to prevent contamination during movements. The bioreactor may be able to fit into an incubator and connected to one or two media reservoirs through ports (198, 199, 180, or 179). Gas exchange can be obtained through port (188), a Luer lock tube connector (214), and a syringe filter (280). Under compressive stress control, the cyclic compression can be carried out at compressive stress preferably of from about 0 to about 20 MPa, more preferably of from about 0 to about 10 MPa, most preferably of from 0 to about 6 MPa, at a frequency preferably of from about 0.001 to about 5 Hz, more preferably of from about 0.1 to about 3 Hz, and most preferably of from about 0.1 to about 1 Hz, for a period of time preferably of from about 5 minutes to about 16 hours, more preferably of from 5 minutes to about 8 hours, most preferably of from about 5 minutes to about 4 hours every day, and for a total duration preferably of 1 to about 40 days, more preferably of 1 to about 28 days, most preferably of 1 to about 14 days. Under displacement control, a dynamic displacement may be superimposed on a static displacement. The static displacement can be preferably from about 0 to about 20%, more preferably from about 0 to about 10%, most preferably from about 0 to about 5% of the cartilage graft thickness. The cyclic compression can be carried out at dynamic displacement amplitude preferably of from about 0 to about 50%, more preferably of from about 0 to about 20%, most preferably of from about 0 to about 5% of the cartilage graft thickness, at a frequency preferably of from about 0.001 to about 5 Hz, more preferably of from about 0.1 to about 3 Hz, and most preferably of from about 0.1 to about 1 Hz, for a period of time preferably of from about 5 minutes to about 16 hours, more preferably of from 5 minutes to about 8 hours, most preferably of from about 5 minutes to about 4 hours every day, and for a total duration preferably of 1 to about 40 days, more preferably of 1 to about 28 days, most preferably of 1 to about 14 days. At the end of cultivation, the coherent stack of cartilage slices or cartilage disc may be implanted along with or without the bottom porous platen (227).

Before applying mechanical stimuli, cell seeding on osteochondral plugs can be conducted outside of a bioreactor. Alternatively, cell seeding can be conducted directly in the bioreactor as illustrated in FIG. 26 and FIG. 27.

The cartilage cap and the bone portion of the devitalized osteochondral plug can be recellularized with the same type of cells. Alternatively, the cartilage cap and the bone portion of the devitalized osteochondral plug can be recellularized with different type of cells. Recellularizable cells isolated from autologous or allogenous sources can be seeded on the devitalized cartilage grafts before application of mechanical stimuli. Optionally, a centrifugal force or a positive pressure can be applied to facilitate cell adhesion onto the devitalized cartilage graft. The cartilage cap of the devitalized osteochondral plug can be recellularized with one or more than one type of cells from recellularizable cells. The bone portion of the devitalized osteochondral plug can be recellularized with one or more than one type of cells from recellularizable cells.

Figure 26:
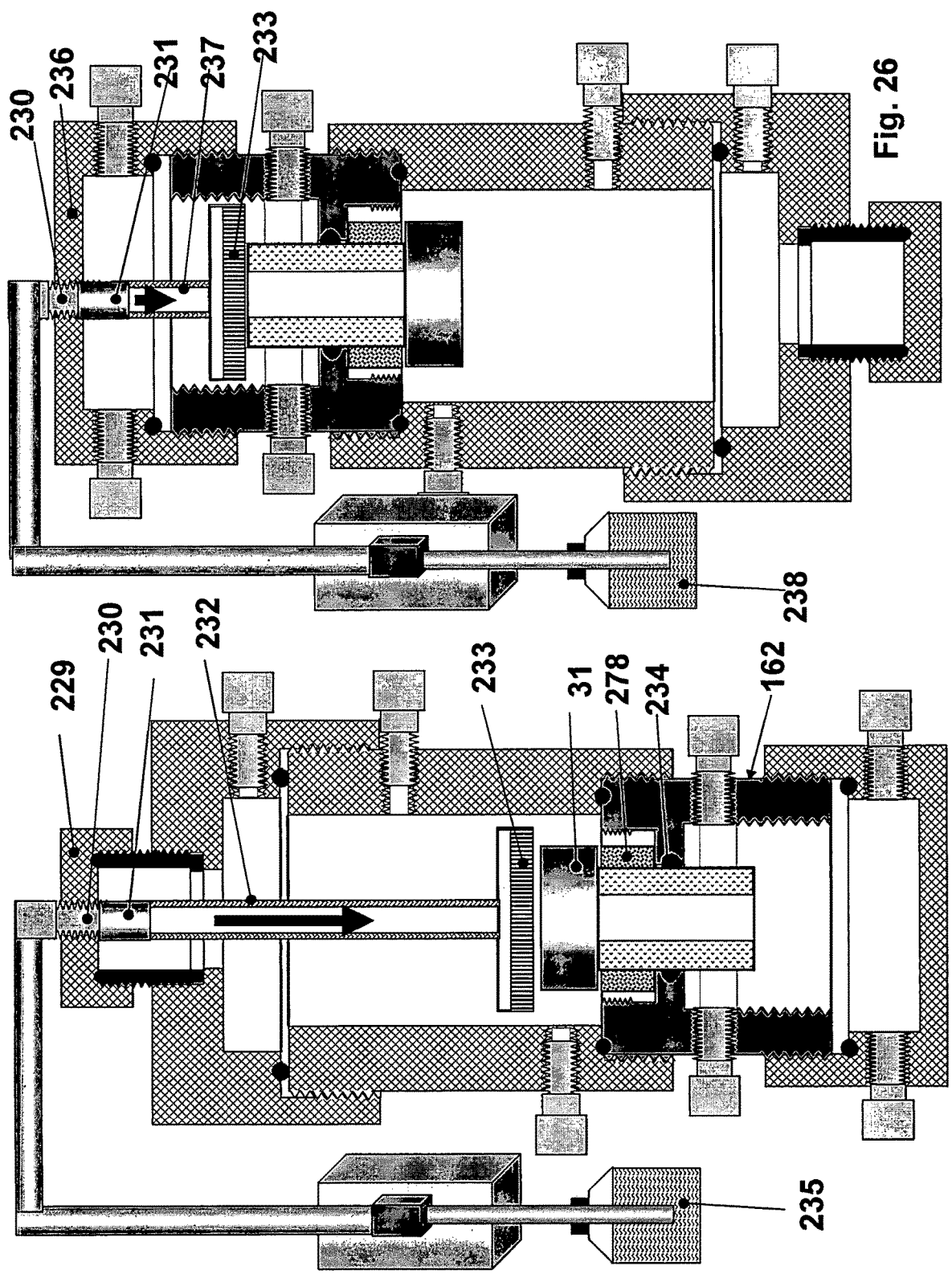
FIG. 26 illustrates a bioreactor assembly that is positioned vertically. The cartilage cap and the bone portion of a devitalized osteochondral plug are recellularized separately with the same or different cell types in a bioreactor.

As illustrated in FIG. 26, when any one of the osteochondral plugs in FIG. 2-FIG. 5 is fit into the culture well (162), the inferior surface facing the osteochondral bone portion of the cartilage cap (6, 37, 39, 41, 43 or 45) can be placed against the top surface of a porous hollow cylinder (278). The bone portion can be fit into the middle hole (166) of the culture well (162) with the rubber o-ring (234) on the peripheral surface that creates a seal. Cell suspension can be either directly injected or driven by a pump through a port (230), and through a rigid feeding tube (232) and the sprinkle head (233) to spray the cells onto the cartilage cap of the osteochondral plug. The bioreactor can also be turned upside down with the osteochondral plug secured in the culture well and the bone portion facing up. In this configuration, cell suspension that can be the same or different from the cell suspension for the cartilage cap recellularization may be either directly injected or driven by a pump through a port (230), and through a rigid feeding tube (237) and the sprinkle head (233) to spray the cells onto the bone portion of the osteochondral plug.

Figure 27:
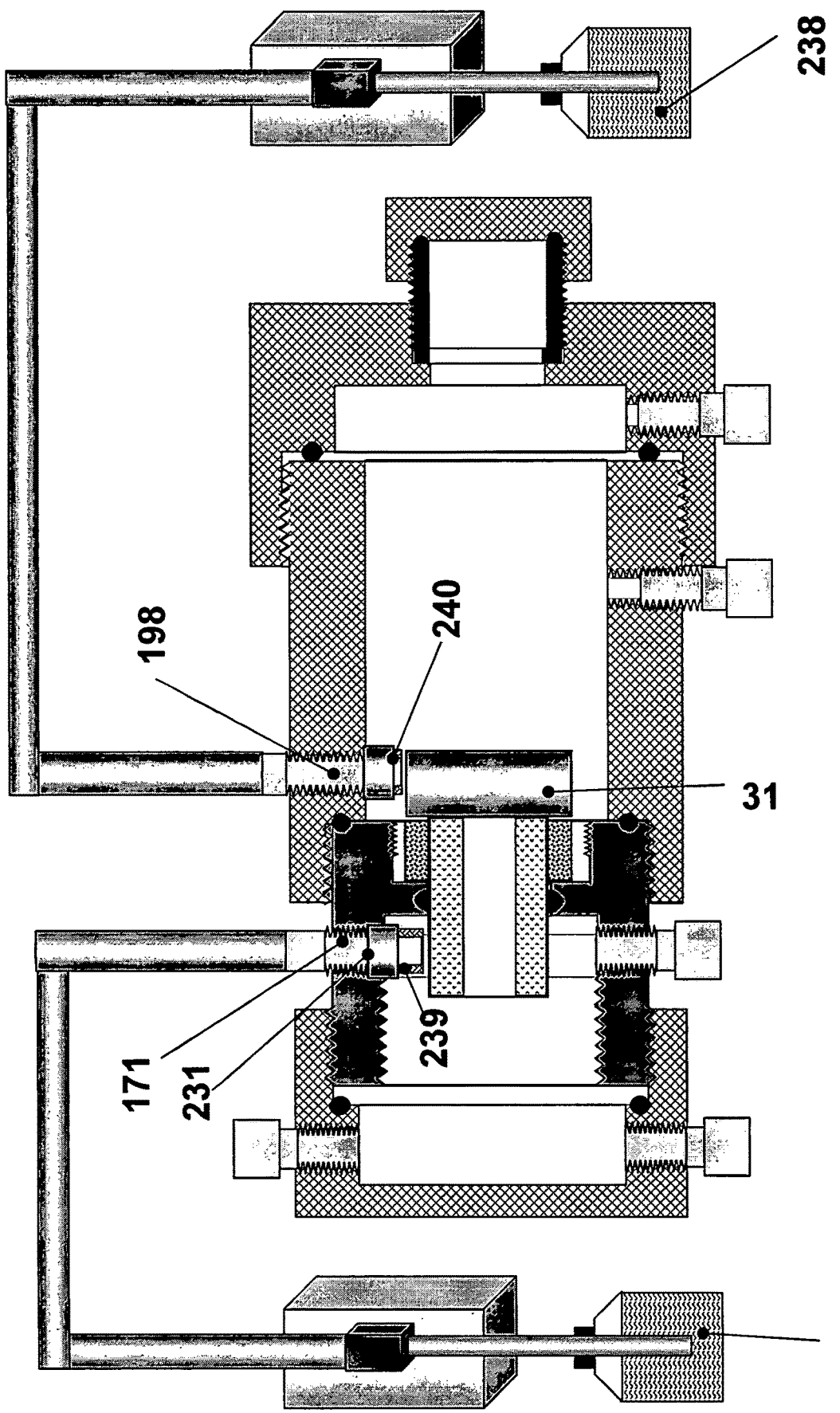
FIG. 27 illustrates a bioreactor assembly that is positioned horizontally. The cartilage cap and the bone portion of a devitalized osteochondral plug are recellularized at the same time with the same or different cell types in a bioreactor.

In another embodiment, the bioreactor can be placed horizontally as illustrated in FIG. 27 with an osteochondral plug secured in the culture well as described above. Cell suspension for cartilage cap recellularization can be injected or driven by a pump through a port (198) and a rigid feeding tube (240) onto the circumferential surface of the cartilage cap. Cell suspension for the bone portion recellularization can be injected or driven by the pump through a port (171) and a rigid feeding tube (239) onto the circumferential surface of the bone portion. The cell seeding system as illustrated FIG. 26 and FIG. 27 can be applied in conjunction with the bioreactor systems to replenish fresh cells between or during compression regime.

After cell seeding, the osteochondral plug can be cultured under compression with a loading shaft with or without a spring serially attaching to as illustrated in FIG. 28. The bottom of the osteochondral plug can be supported by a supporting ring (248) that may be screwed into the bottom of the culture well (162) during compression. The cartilage cap of the osteochondral plug can be placed between a porous platen (226) and a porous ring (241) in a confining ring (204). The porous platen or the porous ring can be made of a group of materials such as titanium, stainless steel, biocompatible polymers, ceramics, hydroxyapatite, calcium phosphate, calcium sulfate, cancellous bone, or cortical bone. A spring (225) can be serially connected to the bottom of the load shaft (224) to allow larger range and better control of the movement of the loading shaft during loading. The end of the spring can be flat and fixed onto the top porous platen (226). Alternatively, the loading shaft can directly compress on the cartilage cap using a solid bead (243) and a porous platen (226) to ensure the centerline of the loading shaft being parallel to the centerline of the osteochondral plug to be compressed as illustrated in the right panel of FIG. 28. The loading shaft can be driven by a computer controlled cam and/or stepper motor to move up and down to create a cyclic compression within the bioreactor. The compressive stress can be monitored with a load cell (222) and the strain of the loading can be adjusted to obtain the target stress. A flexible bellow (223) can be assembled between the top of the loading shafts (224) and the top chamber assembly (211) to prevent contamination during movements. The bioreactor may be able to fit into an incubator and connected to a media reservoir through ports (198, 199, 180, 179). Gas exchange can be obtained through port (188), a Luer lock tube connector (214), and a syringe filter (280). Under compressive stress control, the cyclic compression can be carried out at compressive stress preferably of from about 0 to about 20 MPa, more preferably of from about 0 to about 10 MPa, most preferably of from 0 to about 6 MPa, at a frequency preferably of from about 0.001 to about 5 Hz, more preferably of from about 0.1 to about 3 Hz, and most preferably of from about 0.1 to about 1 Hz, for a period of time preferably of from about 5 minutes to about 16 hours, more preferably of from 5 minutes to about 8 hours, most preferably of from about 5 minutes to about 4 hours every day, and for a total duration preferably of 1 to about 40 days, more preferably of 1 to about 28 days, most preferably of 1 to about 14 days.

Figure 30:
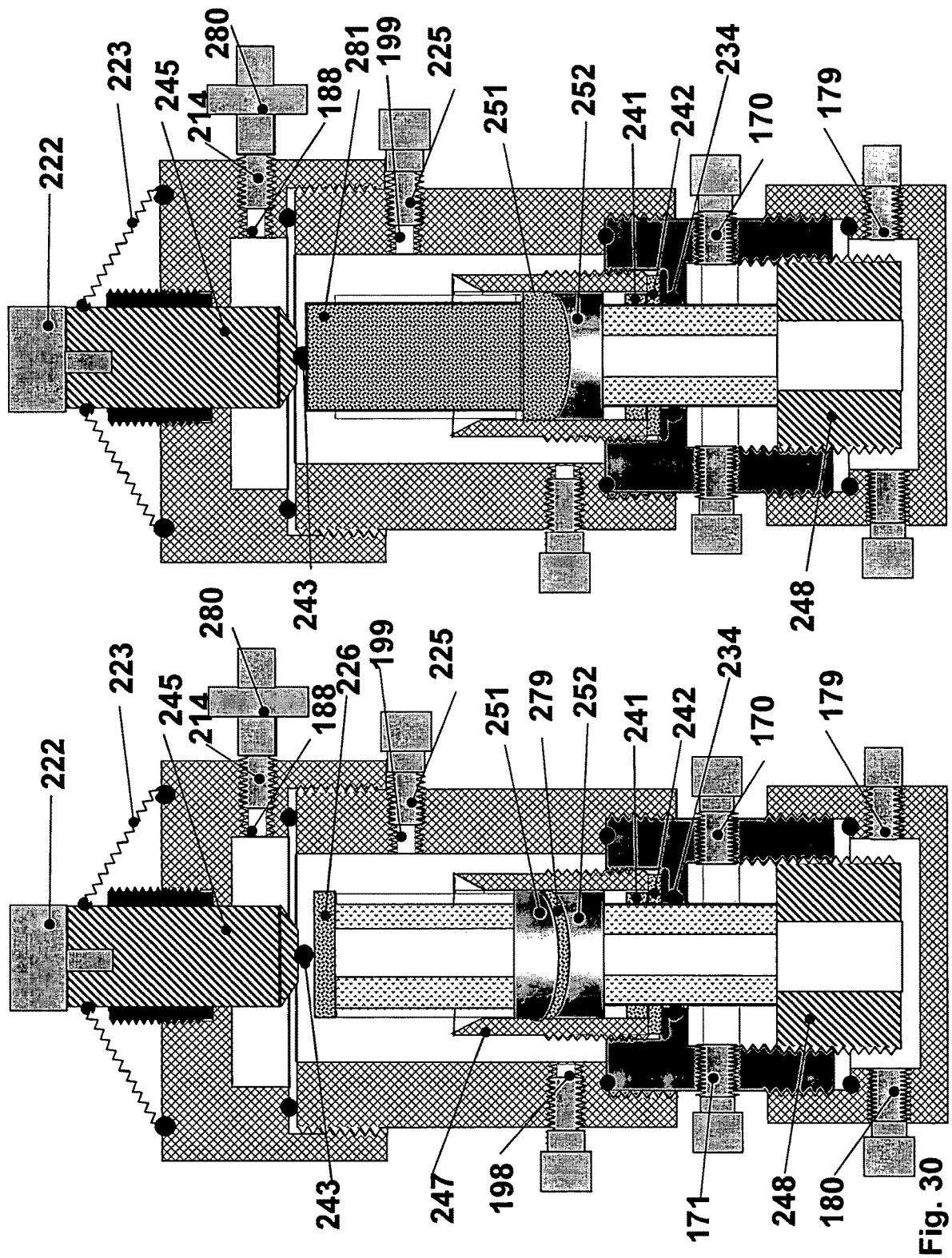
FIG. 30 illustrates a bioreactor assembly wherein the cartilage caps of two osteochondral plugs are placed opposite each other to create congruent surfaces within a confining ring and is compressed with a compression shaft. Alternatively, a mold with a target curvature are compressed against a cartilage cap of an osteochondral plug.

If desired, osteochondral plugs seeded with cells can be compressed with cartilage caps opposite each other as illustrated in FIG. 29 and FIG. 30. The compression can be either confined or unconfined. The bottom of the first osteochondral plug can be supported by a supporting ring (248) that may be screwed into the bottom of the culture well (162) during compression. The second osteochondral plug can be placed on top of the first osteochondral plug and the superficial surface of the cartilage cap of the osteochondral plugs may be placed opposing each other. For confined compression, cartilage caps from both osteochondral plugs can be placed in a confining ring (247) with or without a porous platen (226) in between (FIG. 29). If congruent contoured surfaces between two osteochondral plugs are desired, a porous platen (279) that has the target curvature according to the contour of the recipient joint (convex or concave surfaces) as illustrated in the left panel of FIG. 30 can be used between the two opposing osteochondral plugs.

Alternatively, a mold that has a desired curvature can be used to replace one of the osteochondral plugs as illustrated in the right panel of FIG. 30. The mold can be made of a porous material that may be made of a group of materials such as titanium, stainless steel, biocompatible polymers, ceramics, hydroxyapatite, calcium phosphate, calcium sulfate, cancellous bone, or cortical bone. The loading shaft can directly compress on the bone portion of the second osteochondral plug or a mold through a solid bead (243) and a porous platen (226) to ensure the center line of the loading shaft being parallel to the centerline of the osteochondral plugs to be compressed.

The loading shaft can be driven by a computer controlled cam and/or stepper motor to move up and down to create a cyclic compression within the bioreactor. The compressive stress can be monitored with a load cell (222) and the strain of the loading can be adjusted to obtain the target stress. A flexible bellow (223) can be assembled between the top of the loading shafts (224) and the top chamber assembly (211) to prevent contamination during movements. The bioreactor may be able to fit into an incubator and connected to a media reservoir through ports (198, 199, 180, or 179). Gas exchange can be obtained through port (188), a Luer lock tube connector (214), and a syringe filter (280). Under compressive stress control, the cyclic compression can be carried out at compressive stress preferably of from about 0 to about 20 MPa, more preferably of from about 0 to about 10 MPa, most preferably of from 0 to about 6 MPa, at a frequency preferably of from about 0.001 to about 5 Hz, more preferably of from about 0.1 to about 3 Hz, and most preferably of from about 0.1 to about 1 Hz, for a period of time preferably of from about 5 minutes to about 16 hours, more preferably of from 5 minutes to about 8 hours, most preferably of from about 5 minutes to about 4 hours every day, and for a total duration preferably of 1 to about 40 days, more preferably of 1 to about 28 days, most preferably of 1 to about 14 days.

In another embodiment of the current invention, cartilage discs or stack of slices can be recellularized and cultured in vitro in a bioreactor as described. Meanwhile, the bone plug that may be cleaned and disinfected without cartilage tissue attached, and/or bony material made from, for example, demineralized bone matrix, hydroxyapatite, ceramics, calcium phosphate, or calcium sulfate in the form of cylinders can be recellularized and cultured separately from the cartilage discs or slices in a bioreactor. After culturing in separation for certain duration, the soft tissue, i.e., the cartilage discs or slices, and the hard tissue, i.e., the bony tissue can be assembled together to be implanted directly or further cultured in a bioreactor to form a composite osteochondral cartilage grafts.

If desired, the devitalized osteochondral plugs, cartilage discs, or cartilage slices can be recellularized in vivo. In one embodiment, the devitalized cartilage grafts can be implanted in a recipient's own soft tissue, for example, under a muscle pouch or a fat pad or other soft tissue containing progenitor or stromal cells for about 7 days to about 3 months. Optionally, before the soft tissue implantation, the devitalized cartilage grafts can be seeded with cells from one or more than one type of cells from recellularizable cells. The devitalized cartilage graft can also be treated with chemical stimuli before or after the in vivo soft tissue implantation. In addition, centrifugal force or positive pressure can be optionally applied to facilitate cell adhesion onto the devitalized cartilage graft. Before implanting into the cartilage defect site in the recipient, the implanted cartilage grafts may be retrieved from the soft tissue, trimmed off the excessive fibrous tissue if present surrounding the recellularized cartilage graft, and rinsed with an isotonic solution, such as isotonic saline. Then the in vivo recellularized graft can be implanted into the target defect site.

Figure 31A:
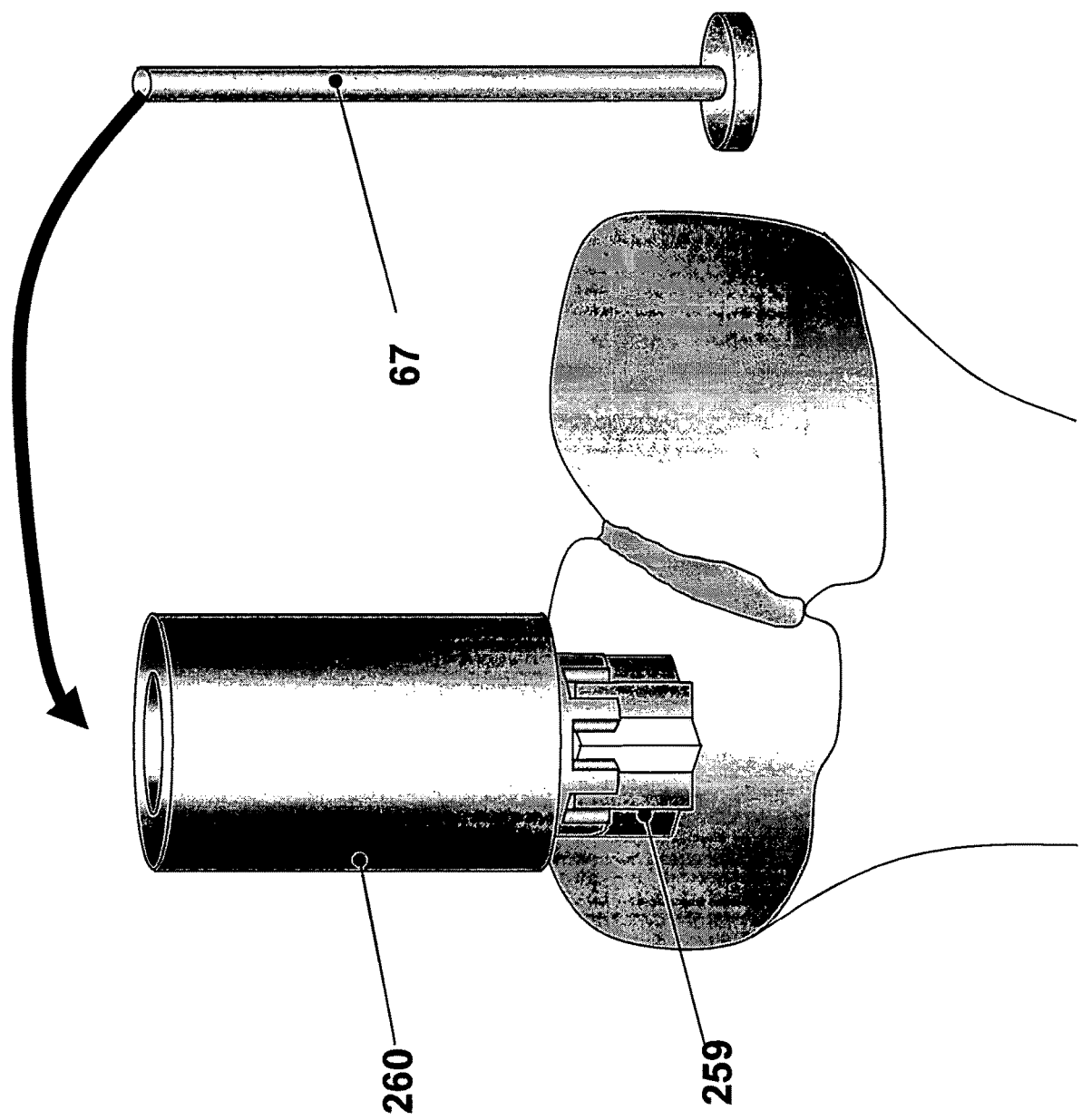
FIG. 31a illustrates a view of a procedure during open knee surgery wherein a cutting device is pushed into the cartilage portion of recipient defect site after a straight bore has been created using conventional surgical tools.

Before implantation, a first bore at the cartilage defect site may be created down into the osteochondral bone to remove the damaged cartilage tissue and underlying bone in the recipient. In one aspect, the diameter of the first bore matches the maximum diameter of the bone portion of the osteochondral plug if the osteochondral plug may be chosen to be used as a graft. The length of the first bore can be the same as the osteochondral plug to be implanted. Then, a second shaped bore, such as a star-shaped bore, may be created at the cartilage portion of the first bore. The second shaped bore may be concentric to and on top of the first bore. The second shaped bore can be crafted using a custom designed coring device as illustrated in FIG. 31a. The coring device may be composed of a star-shaped cutter (259) to match the shape and size of the cartilage cap of an osteochondral plug, cartilage disc, or cartilage slices to be implanted, and an adaptor (260) to assist the coring.

Figure 31B:
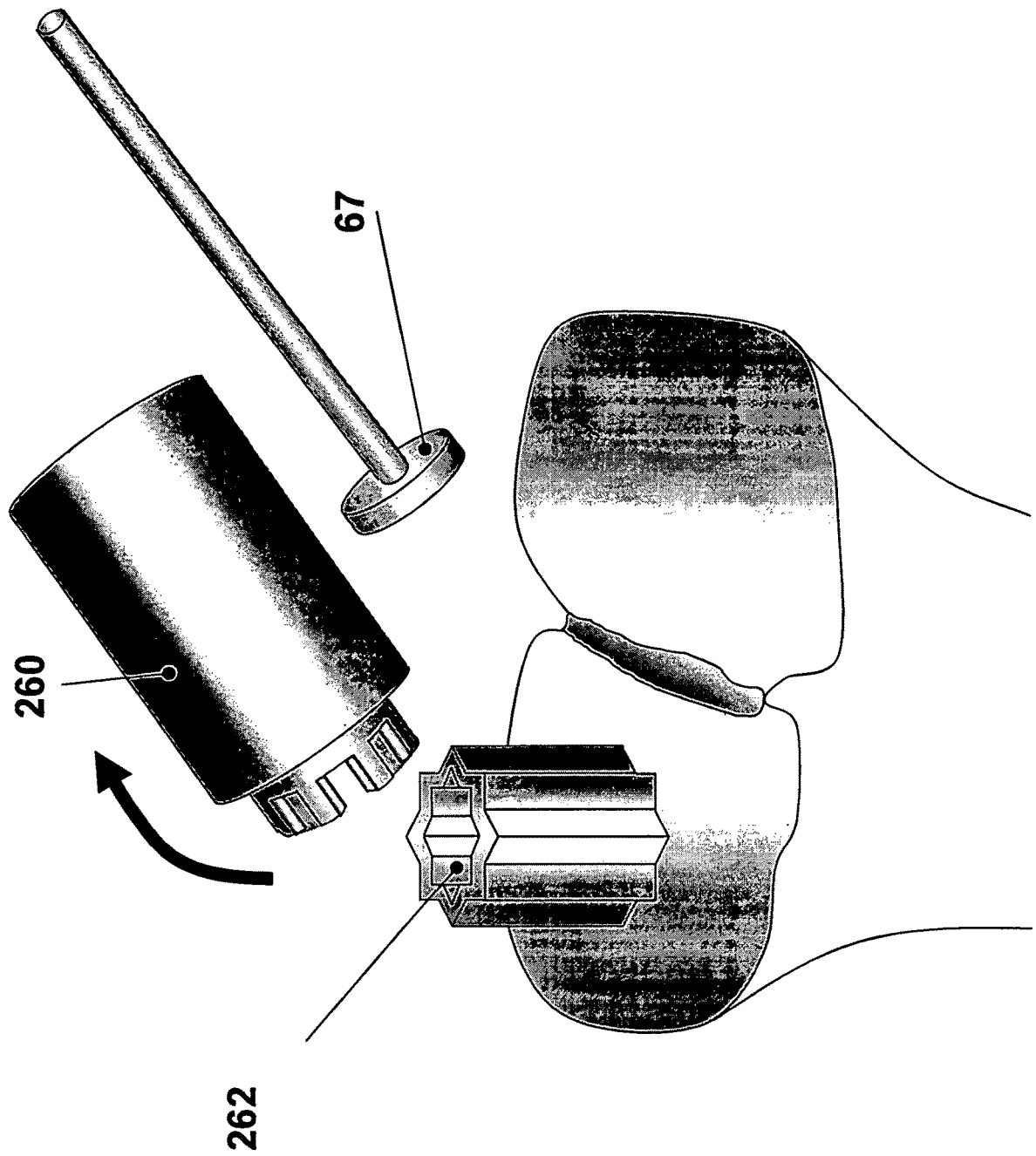
FIG. 31b illustrates a view of a procedure during open knee surgery wherein the adaptor is released from the cutting device and a star-shaped cutter remains in the recipient defect site. The star-shaped cutter is used as a boundary for removing the damaged cartilage from the recipient cartilage to create a star-shaped bore in the cartilage portion of the recipient defect site.

After the custom designed coring device cuts through the cartilage tissue and reaches the bone, the adaptor (260) can be removed with the help of a pushing device (67 in FIG. 31a) and the star-shaped cutter (259) remains in place FIG. 31b. The star-shaped cutter can be used as a boundary for removing the damaged cartilage tissue within the star-shaped cutter from the recipient to create a star-shaped bore in the cartilage portion of the recipient defect site. The star-shaped cutter may be designed so that its outer surface may be straight and matches the size and shape of the cartilage portion of the cartilage graft to be implanted (FIG. 32). The bottom portion of the inner surface of the star-shaped cutter may be angled to form a beveled sharp cutting edge (261).

Figure 34:
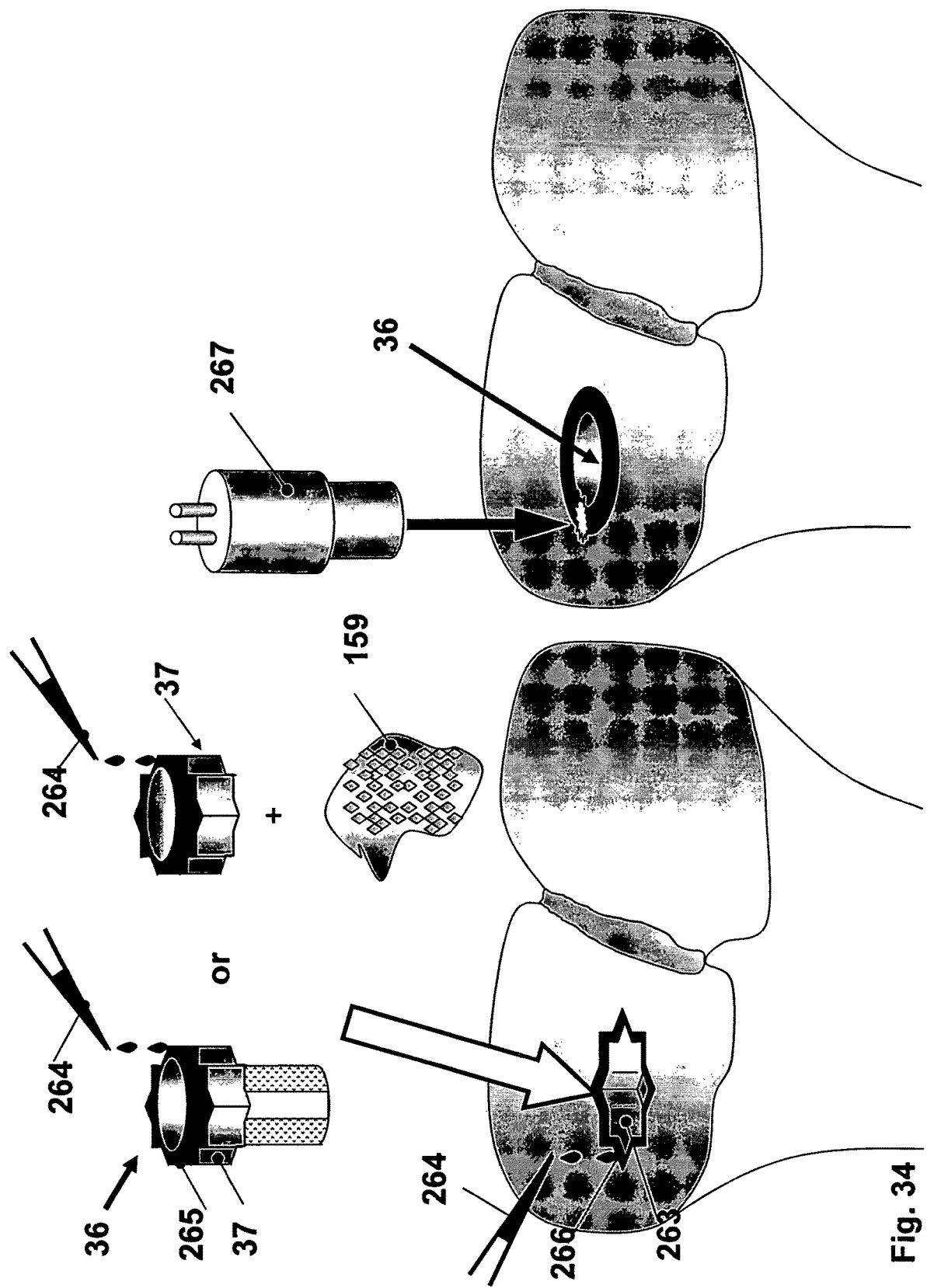
FIG. 34 illustrates a view of a procedure during open knee surgery wherein the shaped cartilage bore and the circumferential area of a cartilage cap on an osteochondral plug or a cartilage disc is treated with a photoactive dye before insertion of the cartilage graft into the shaped bore. An energy source is applied to seal the cartilage interface.

In one embodiment, an osteochondral plug (with or without recellularization in situ, in vitro, or in vivo) can be used to repair the defect site as illustrated in FIG. 34. The osteochondral plug may be selected to match the size, contour, and location of the defect site. A bonding agent, such as a photoactive dye, can be dissolved in an isotonic solution, such as isotonic saline or phosphate buffered saline. The shaped second bore on the cartilage tissue along with the first bore at the bone portion of the recipient can be filled with the photoactive dye for 5-10 minutes. Then the photoactive dye may be removed and the first bore in the bone portion is optionally rinsed with an isotonic solution, such as isotonic saline.

If a step cylindrical osteochondral plug is used as a graft, the osteochondral plug can fit tightly into the first bore and supported by the wall of the bone portion of the first bore. Alternatively, if the diameter of the bone portion of the step cylindrical osteochondral plug is slightly smaller than the diameter of the first bore in the bone portion of the recipient, a bone filler can be inserted into the bone portion of the first bore that is created at the defect site to fill the gap between the wall of the first bore and the bone portion of the osteochondral plug. The bone filler can also be inserted into the first bore to create a flat surface at the bottom of the first bore so that it can provide support for the osteochondral plug. Meanwhile, the same bone filler can be inserted into the gaps or channels or slots (if present) on the osteochondral plug. In addition, if the cartilage cap of the step cylindrical osteochondral plug fits loosely into the second bore, a cartilage filler can be applied in the gap between the peripheral of the cartilage cap of the osteochondral plug and the second shaped bore. The cartilage filler can also be inserted into gaps or a bore or channels or slots on the cartilage cap from the bottom of the osteochondral plug if such gaps or bore or channels or slots are present. The same or a different photoactive dye used to treat the bores created at the recipient cartilage defect can be used to treat the circumferential area of the cartilage cap of the osteochondral plug. The superficial surface of the osteochondral plug can be at the same height as the surface of the surrounding recipient cartilage surface. If desired the osteochondral plugs can be applied in combination with the cartilage discs or slices or flakes to match the depth and/or contour of the recipient cartilage and to optimize the repair process.

In another embodiment, a cartilage disc (with or without recellularization in situ, in vitro, or in vivo) can be used to repair the defect site as illustrated in FIG. 34. The cartilage disc may be selected to match the size, contour, and location of the defect site. A bonding agent, such as a photoactive dye, can be dissolved in an isotonic solution, such as isotonic saline. The shaped second bore on the cartilage tissue along with the first bore at bone portion of the recipient can be filled with the photoactive dye for 5-10 minutes. Then the photoactive dye may be removed and the first bore in the bone portion is optionally rinsed with an isotonic solution, such as isotonic saline. A bone filler can be used to fill up the bone portion of the first bore to provide support for the cartilage disc. The cartilage disc can fit tightly into the shaped second bore. Alternatively, if the cartilage disc fits loosely into the second bore, a cartilage filler can be applied in the gap between the peripheral of the cartilage disc and the second shaped bore. The cartilage filler can also be inserted into a bore or channels or slots on the cartilage disc from the bottom of the cartilage disc if such bore or channels or slots present. The same or a different photoactive dye used to treat the bores created at the recipient cartilage defect can be used to treat the circumferential area of the cartilage disc. The cartilage disc can be inserted into the defect site with the cartilage disc being at the same height as the surrounding recipient cartilage. If desired the cartilage discs can be applied in combination with the osteochondral plugs, cartilage slices or flakes to match the depth and/or contour of the recipient cartilage and to optimize the repair process.

In yet another embodiment, cartilage slices (with or without recellularization in situ, in vitro, or in vivo) can be used to repair the defect site. The cartilage slices can be tailored according to the size, contour, and location of the bore created at the cartilage defect site. A bonding agent, such as a photoactive dye, can be dissolved in an isotonic solution, such as isotonic saline. The shaped second bore on the cartilage tissue along with the first bore at bone portion of the recipient can be filled with the photoactive dye for 5-10 minutes. Then the photoactive dye may be removed and the first bore in the bone portion is optionally rinsed with an isotonic solution, such as isotonic saline. A bone filler can be used to fill up the bone portion of the first bore to provide support for the cartilage slices. The cartilage slices may fit tightly into the shaped second bore. Alternatively, if the cartilage slices fit loosely into the second bore, a cartilage filler can be applied in the gap between the peripheral of the cartilage slices and the second shaped bore. The same or a different photoactive dye used to treat the bores created at the recipient cartilage defect can be used to treat the circumferential area of the cartilage slices. The shaped cartilage slices can be stacked together, optionally a second bonding agent and/or with viable cells seeded between the slices, and inserted into the defect site until at the same height as the surrounding cartilage. The second bonding agent may be the same or different from the bonding agent used to treat the circumferential area of the cartilage slices. If desired the cartilage slices can be applied in combination with the osteochondral plugs, cartilage discs or flakes to match the depth and/or contour of the recipient cartilage and to optimize the repair process.

In another embodiment, cartilage curls or flakes (with or without recellularization in situ, in vitro, or in vivo) can be used to repair the cartilage defect site. The cartilage curls or flakes can also be applied in combination with cartilage slices, discs or osteochondral plugs to repair the cartilage defect site. The cartilage curls or flakes may be applied directly or mixed with a matrix, such as demineralized bone matrix, and/or a carrier, such as hyaluronic acid, isotonic saline, phosphate buffered saline or bone marrow from the implant recipient to form cartilage filler. A bone filler can be used to fill up the bone portion of the first bore to provide support for the cartilage flakes or curls. Then the cartilage curl or flake filler, in a form such as a putty or gel, can be placed into the cartilage defect site directly or injected into the cartilage defect site through a syringe that may be connected to a stent or needle. A stack of cartilage slices or a cartilage disc can be placed on top of the cartilage flake or curl filler with the superficial surface of the stack of the cartilage slice or the cartilage disc being at the same height as the surface of the surrounding recipient cartilage.

The bone filler can be a mixture of a matrix with or without a carrier. The bone filler can be in the format of a sheet, a disc, a tape, a sponge, a cube, a solid or hollow cylinder, particles, gel, or putty. The matrix may be one or more of, for example, autologous crushed bone harvested from the defect site; demineralized bone matrix; cancellous and cortical bone mixture; small intestine submucosa, amniotic membrane, ligament, tendon, skin, muscle tissue, periostieum, or synovial tissue; ceramics; hydroxyapatite; calcium phosphate; calcium sulfate; porous surgical grade titanium or stainless steel; or any combination of the above. The carrier may be one or more of, for example, dihydroxyphenylalanine (DOPA) based adhesive, glucose, concentrated albumin, cyanoacrylate adhesive, gelatin-resorcin-formalin adhesive, chondroitin sulfate aldehyde N-acetylglucosamine (GlcNAc), mussel-based adhesive, poly(amino acid)-based adhesive, cellulose-based adhesive, synthetic acrylate-based adhesives, platelet rich plasma (PRP), monostearoyl glycerol co-Succinate (MGSA), monostearoyl glycerol co-succinate/polyethylene glycol (MGSAPEG) copolymers, or a combination comprising at least one of the foregoing polymers. The carrier can also be one or more of, for example, native or modified collagen, gelatin, agarose, modified hyaluronic acid, fibrin, chitin, biotin, avidin, native or crosslinked chitosan, alginate, demineralized bone matrix, MATRIGEL®, HUMAN EXTRACELLULAR MATRIX®, homogenized connective tissue, proteoglycans, fibronectin, laminin, fibronectin, elastin, heparin, glycerol, or a combination comprising at least one of the foregoing polymers. The carrier may include bioactive growth supplements such as FGF-family, TGF-family, IGF-1, PDGF, EGF, VEGF, HGF, PTHrP, Ihh, dexamethasone, insulin, transferrin, selenium, ITS, or ascorbate. The carrier may also include bioactive growth supplements from the extractions of demineralized bone matrix, basement membrane, or submucosa matrix. The carrier may include cytokines, for example, an IL-1αR antibody, TNF-a receptor antagonist, cyclooxygenase-2 specific inhibitors, MAP kinase inhibitors, NO synthase inhibitors, NF-κB inhibitors, or inhibitors of MMP. Moreover, the carrier may also include one or more than one type of cells from recellularizable cells. The bone filler may also be a cortical and/or cancellous bone plug.

The cartilage filler may be a mixture of a matrix with or without a carrier. The cartilage filler can be in the format of a sheet, a disc, a tape, a sponge, a cube, a solid or hollow cylinder, particles, gel, or putty. The matrix in the cartilage filler may be one or more of, for example, demineralized bone matrix; small intestine submucosa, amniotic membrane, ligament, tendon, skin, muscle tissue, periostieum, synovial tissue, or devitalized cartilage curls and flakes; or any combination of the above. The carrier in the cartilage filler may be one or more of, for example, dihydroxyphenylalanine (DOPA) based adhesive, glucose, concentrated albumin, cyanoacrylate adhesive, gelatin-resorcin-formalin adhesive, chondroitin sulfate aldehyde N-acetylglucosamine (GlcNAc), mussel-based adhesive, poly(amino acid)-based adhesive, cellulose-based adhesive, synthetic acrylate-based adhesives, platelet rich plasma (PRP), monostearoyl glycerol co-Succinate (MGSA), monostearoyl glycerol co-succinate/polyethylene glycol (MGSAPEG) copolymers, or a combination comprising at least one of the foregoing polymers. The carrier in the cartilage filler may be one or more of, for example, native or modified collagen, gelatin, agarose, modified hyaluronic acid, fibrin, chitin, biotin, avidin, native or crosslinked chitosan, alginate, demineralized bone matrix, MATRIGEL®, HUMAN EXTRACELLULAR MATRIX®, homogenized connective tissue, proteoglycans, fibronectin, laminin, fibronectin, elastin, heparin, glycerol, or a combination comprising at least one of the foregoing polymers. The carrier in the cartilage filler may be one or more of, for example, polymethylmethacrylate, polyurethane, acryloilmorpholine, N,N-dimethyl acrylamide, N-vinyl pyrrolidone and tetrahydrofurfuryl methacrylate, hydroxyapatite, cross-linkage or functionalization of hyaluronan-based collagen and alginate, polyurethane, or polylactic acid. The carrier in the cartilage filler may include one or more of, for example, FGF-family, TGF-family, IGF-1, PDGF, EGF, VEGF, HGF, PTHrP, Ihh, dexamethasone, insulin, transferrin, selenium, ITS, or ascorbate. The carrier in the cartilage filler may include one or more of, for example, bioactive growth supplements extracted from demineralized bone matrix, basement membrane, or submucosa matrix. The carrier in the cartilage filler may include one or more photoactive agents, for example, a xanthene dye, naphthalimide compounds, riboflavin-5-phosphate, N-hydroxypyridine-2-(1H)-thione, N-(20-ethylaminoethyl)-4-amino-1,8-naphthalimide, bis-diazopyruvamide-N,N9-bis (3-diazopyruvoyl)-2,29-(ethylenedioxy)bis-(ethylamine) (DPD), diazopyruvoyl (DAP), methylene blue, erythrosin, phloxime, thionine, methylene green, rose Bengal, acridine orange, xanthine dye, thioxanthine dyes, ethyl eosin, eosin Y, or a combination comprising at least one of the foregoing photoactive groups. The carrier in the cartilage filler may include one or more antioxidants, for example, sodium nitroprusside, cartilage matrix glycoprotein (CMGP), vitamins C, vitamin E, selenium, N-Acetylcysteine (NAC) estradiol, glutathione, melatonin, resveratrol, flavonoid, carotene, aminoguanidine, or lycopene. The carrier in the cartilage filler may include one or more crosslinking agents, for example, glutaraldehyde; glyceraldehyde; genipin; glucose or ribose; poly(ethylene glycol) diepoxide crosslinker; poly(ethylene glycol) diglycidyl ether; EDC and NHS; transglutaminase; ethylenediamine; lysyl oxidase family; hexamethylene diisocyanate (HMDIC); dimethyl suberimidate (DMS); dimethyl-3-3'-dithiobispropionimidate (DTBP), or acryl azide. The carrier may include cytokines, for example, an IL-1αR antibody, TNF-a receptor antagonist, cyclooxygenase-2 specific inhibitors, MAP kinase inhibitors, NO synthase inhibitors, NF-κB inhibitors, or inhibitors of MMP. The carrier in the cartilage filler may also include one or more than one type of cells from recellularizable cells The bonding agent can be one or more of photoactive dye(s) which can be, but are not limited to, xanthene dye, naphthalimide compounds, riboflavin-5-phosphate, N-hydroxypyridine-2-(1H)-thione, N-(2'-ethylaminoethyl)-4-amino-1,8-naphthalimide, bis-diazopyruvamide-N,N9-bis (3-diazopyruvoyl)-2,29-(ethylenedioxy)bis-(ethylamine) (DPD), diazopyruvoyl (DAP), methylene blue, erythrosin, phloxime, thionine, methylene green, rose Bengal, acridine orange, xanthine dye, thioxanthine dyes, ethyl eosin, eosin Y, and a combination comprising at least one of the foregoing photoactive groups.

The bonding agent may include one or more of, for example, hyaluronidase, chondroitinase, collagenase, trypsin, superoxide dismutase (SOD), or catalase. The bonding agent may include one or more of bioactive growth supplements from the extractions of demineralized bone matrix, basement membrane, or submucosa matrix. The bonding agent may include one or more of bioactive growth supplements such as FGF-family, TGF-family, IGF-1, PDGF, EGF, VEGF, HGF, PTHrP, Ihh, dexamethasone, insulin, transferrin, selenium, ITS, or ascorbate. The bonding agent may include one or more of, for example, dihydroxyphenylalanine (DOPA) based adhesive, glucose, concentrated albumin, cyanoacrylate adhesive, gelatin-resorcin-formalin adhesive, chondroitin sulfate aldehyde N-acetylglucosamine (GlcNAc), mussel-based adhesive, poly(amino acid)-based adhesive, cellulose-based adhesive, synthetic acrylate-based adhesives, platelet rich plasma (PRP), monostearoyl glycerol co-Succinate (MGSA), monostearoyl glycerol co-succinate/polyethylene glycol (MGSAPEG) copolymers, or a combination comprising at least one of the foregoing polymers. The bonding agent may include one or more of, for example, collagen, gelatin, agarose, modified hyaluronic acid, fibrin, chitin, biotin, avidin, native or crosslinked chitosan, alginate, demineralized bone matrix, MATRIGEL®, HUMAN EXTRACELLULAR MATRIX®, homogenized connective tissue, proteoglycans, fibronectin, laminin, fibronectin, elastin, heparin, glycerol, or a combination comprising at least one of the foregoing polymers. The bonding agent may include one or more of, for example, polymethylmethacrylate, polyurethane, acryloilmorpholine, N,N-dimethyl acrylamide, N-vinyl pyrrolidone and tetrahydrofurfuryl methacrylate, hydroxyapatite, cross-linkage or functionalization of hyaluronan-based collagen and alginate, polyurethane, or polylactic acid. The bonding agent may include one or more of, for example, sodium nitroprusside, cartilage matrix glycoprotein (CMGP), vitamins C, vitamin E, selenium, N-Acetylcysteine (NAC) estradiol, glutathione, melatonin, resveratrol, flavonoid, carotene, aminoguanidine, or lycopene. The bonding agent may include one or more of, for example, glutaraldehyde; glyceraldehydes; genipin; glucose or ribose; poly(ethylene glycol) diepoxide crosslinker; poly (ethylene glycol) diglycidyl ether; EDC and NHS; transglutaminase; lysyl oxidase family; hexamethylene diisocyanate (HMDIC); dimethyl suberimidate (DMS); dimethyl-3-3'-dithiobispropionimidate (DTBP); or acryl azide. The bonding agent may also include one or more than one type of cells from recellularizable cells The cartilage graft such as osteochondral plugs, cartilage discs, cartilage slices, or cartilage flakes or curls as described above can be cleaned, disinfected, and devitalized; or cleaned, disinfected, devitalized, and recellularized in situ, in vitro, or in vivo.

Figure 33:
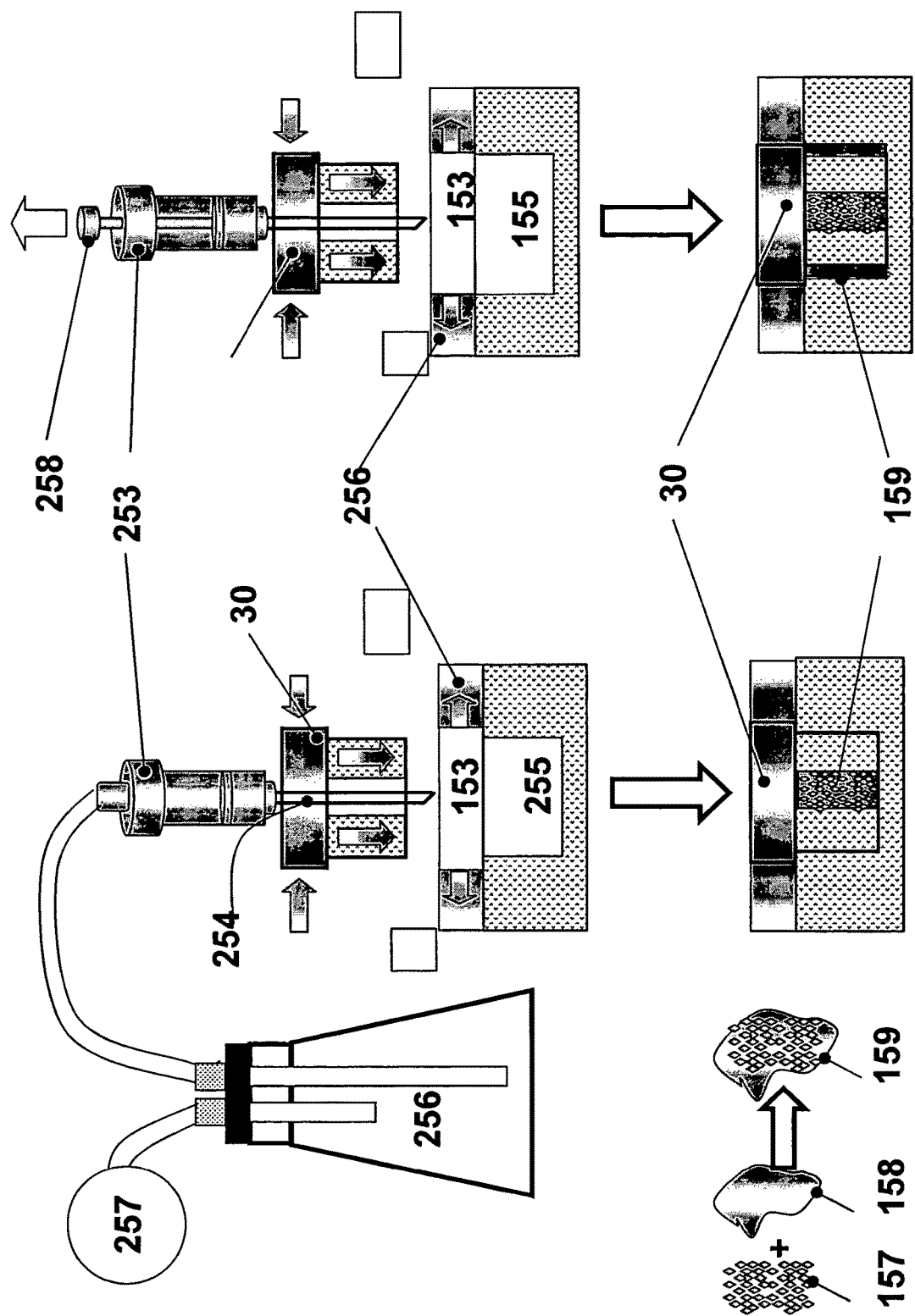
FIG. 33 illustrates a view of one embodiment of an insertion device for surgical insertion of osteochondral plugs, cartilage discs, or a stack of cartilage slices into a bore created at a defect site.

In one embodiment, in order to easily insert the cartilage graft (such as osteochondral plug, or cartilage disc, or cartilage slices) into the bore created at the recipient cartilage defect site and minimize the compressive force applied on the cartilage graft during insertion, an insertion device (253) can be applied (FIG. 33). A thin needle (254) attached to a syringe of the insertion device (253) can penetrate the cartilage portion of a cartilage graft and transfer the cartilage graft into the bore that may be created on the defect site until the circumferential surface of the cartilage cap on the osteochondral plug or cartilage disc or a stack of cartilage slices becomes interference with the recipient tissue. Then the needle may be inserted further through the cartilage portion until it reaches the underlying bone of the recipient tissue or bone filler if present.

A vacuum device (257) or a plunger (258) can be applied to remove the air/gas and/or fluid trapped inside of the bore to allow ambient pressure above the graft to push the cartilage graft into said defect site. The bore created in the recipient tissue at the defect site can be a straight (155) or step cylindrical (255) shape as illustrated in FIG. 33. If a step cylindrical shape osteochondral plug may be used as graft and fit into a straight bore, a bone filler can fill in the gap between the bone portion of the step cylindrical osteochondral plug and the wall of the bore (155) in the bone portion.

Alternatively, if a step cylindrical shape osteochondral plug may be used as a graft and fit into a step cylindrical bore (255), the osteochondral plug may be tightly fit into the bore. If gaps, or a bore, or channels, or slots are crafted on the bone portion of the osteochondral plug, the gaps or a bore or channels or slots can be filled with the same bone filler as described above. In all cases, the cartilage cap of an osteochondral plug, or cartilage disc, or cartilage slices can be tightly fit into the bore and supported by the wall of either the bone or cartilage portion of the bore. The superficial surface of the osteochondral plug, cartilage disc, or cartilage slices may be at the same height as the surface of the surrounding recipient cartilage surface. If desired, bone filler can also be injected into the bone portion of the bore in the recipient through the same needle on the insertion device after the cartilage graft has been properly inserted.

After insertion of the cartilage grafts and a time period of about 2 to about 10 minutes, the photoactivated dye, if chosen as one of the bonding agents, can be activated by a laser as illustrated in FIG. 34. The laser wave length can be from long ultraviolet 250 nm to far infrared 900 nm depending on the type of photoactive dye that is used. The laser beam can be delivered through an optical fiber with a spot size of about 500 micrometer to about 5 mm. The power fluence of the laser is about 10 to about 800 J/cm$^2$ and the irradiation/exposure time can be between about 30 sec to about 30 minutes. The interface between the boundaries of the cartilage being repaired (266) and the cartilage graft (36 or 37 as illustrated in FIG. 34) being used in the repair can be sealed with the surrounding recipient cartilage tissue by this photoactivated integration. If viable cells are present in the cartilage grafts, in order to prevent the phototoxicity of the photoactive dye, the cartilage matrix can be optionally soaked with antioxidants, such as lycopene, to protect viable cells presented in the in vitro, in vivo, or in situ recellularized devitalized cartilage graft. Alternatively, one or more antioxidants can be included in the photoactive dye solution to prevent phototoxicity.

Figure 35A:
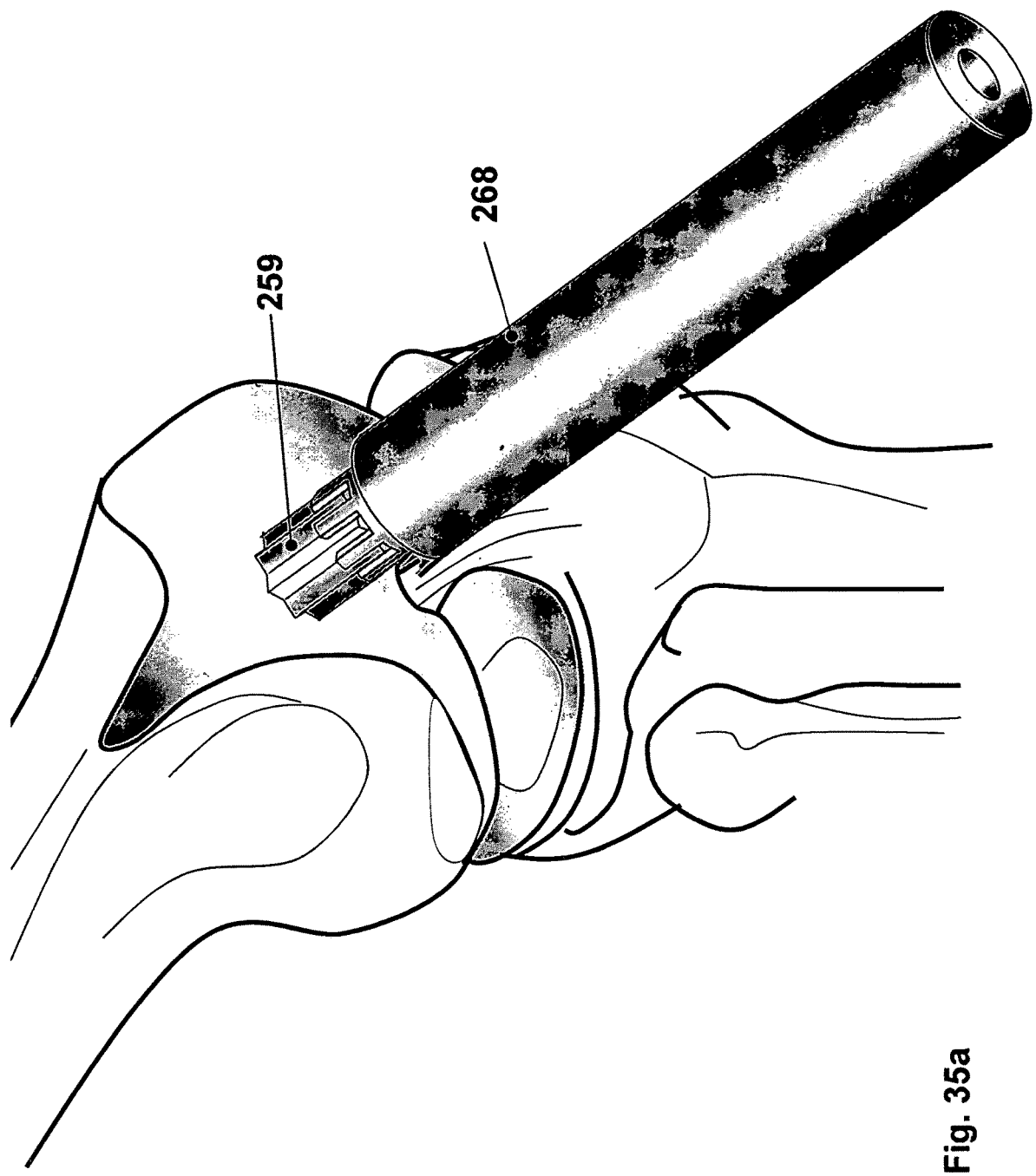
FIG. 35a illustrates a view of a procedure during arthroscopic minimally invasive surgery wherein a cutting device is pushed into the cartilage portion of recipient defect site after a straight bore has been created using conventional surgical tools.
Figure 35B:
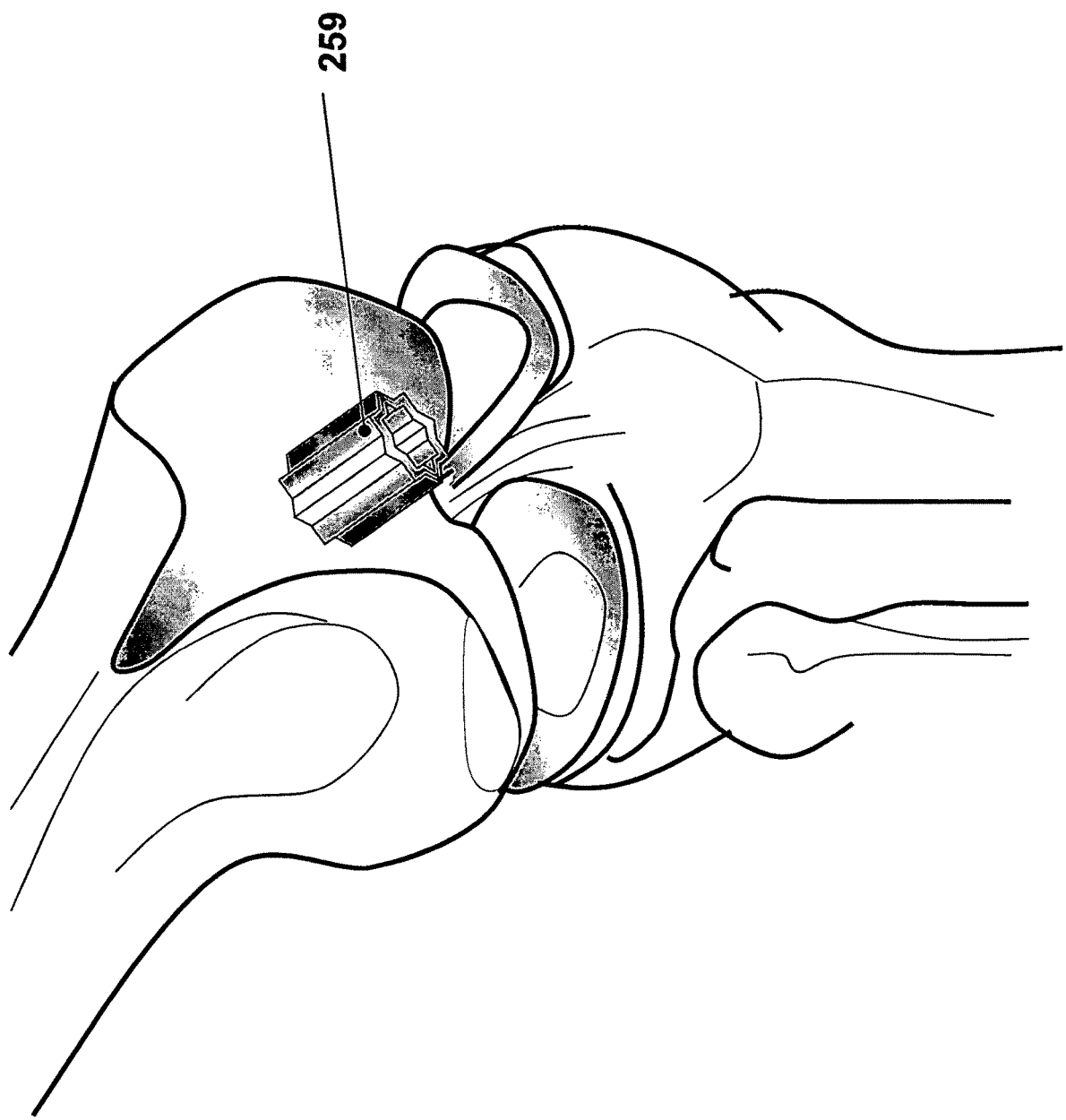
FIG. 35b illustrates a view of a procedure during arthroscopic minimally invasive surgery wherein the adaptor is released from the cutting device and a star-shaped cutting blade remains in the recipient defect site. The star-shaped cutting blade is used as a boundary for removing the damaged cartilage within the boundary from the recipient cartilage to create a star-shaped bore in the cartilage portion of the recipient defect site.
Figure 36:
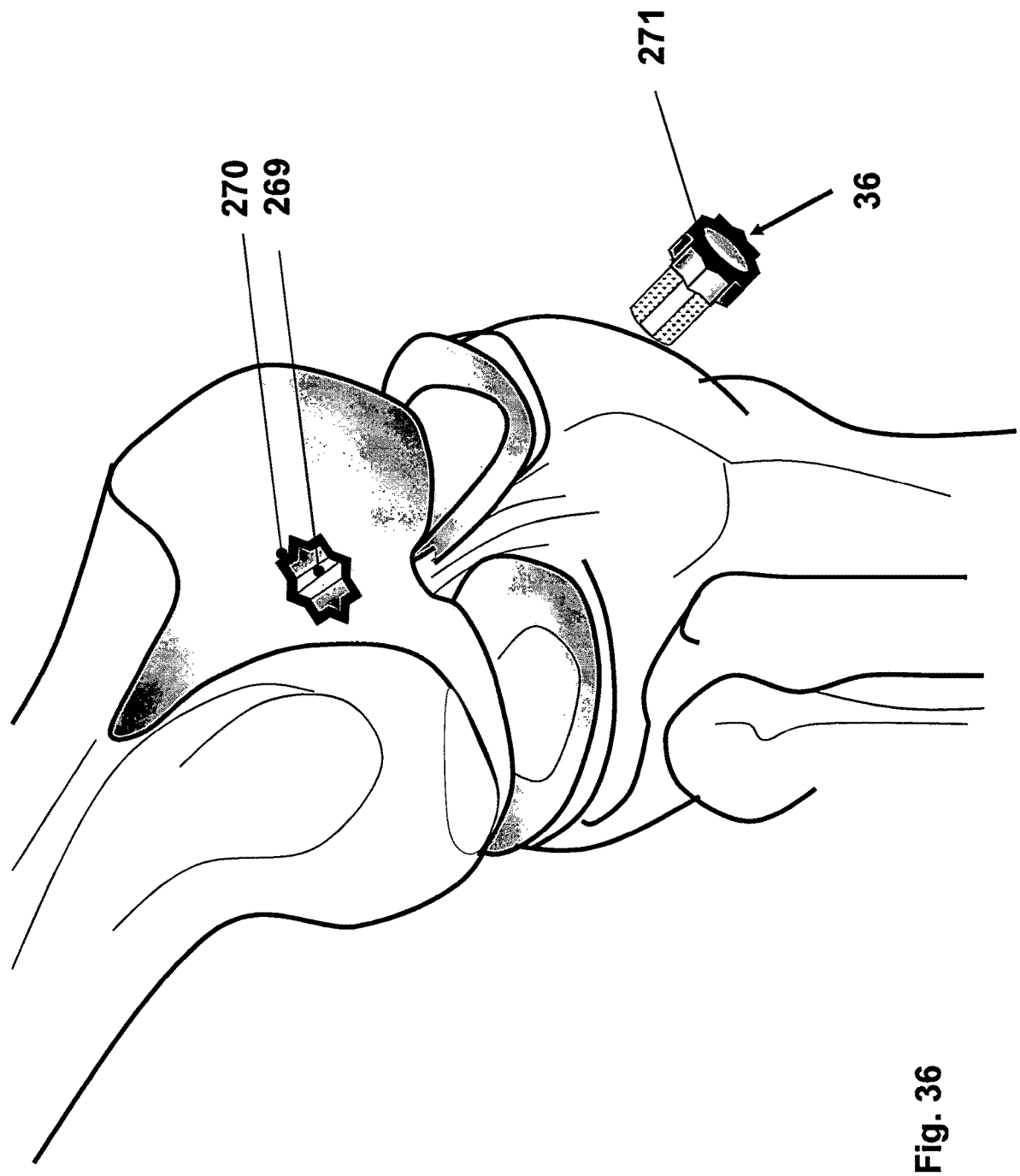
FIG. 36 illustrates a procedure during arthroscopic minimally invasive surgery wherein the shaped cartilage bore and the circumferential area of a cartilage cap on an osteochondral plug or a cartilage disc is treated with a photoactive dye before insertion of the cartilage graft into the shaped bore.
Figure 37:
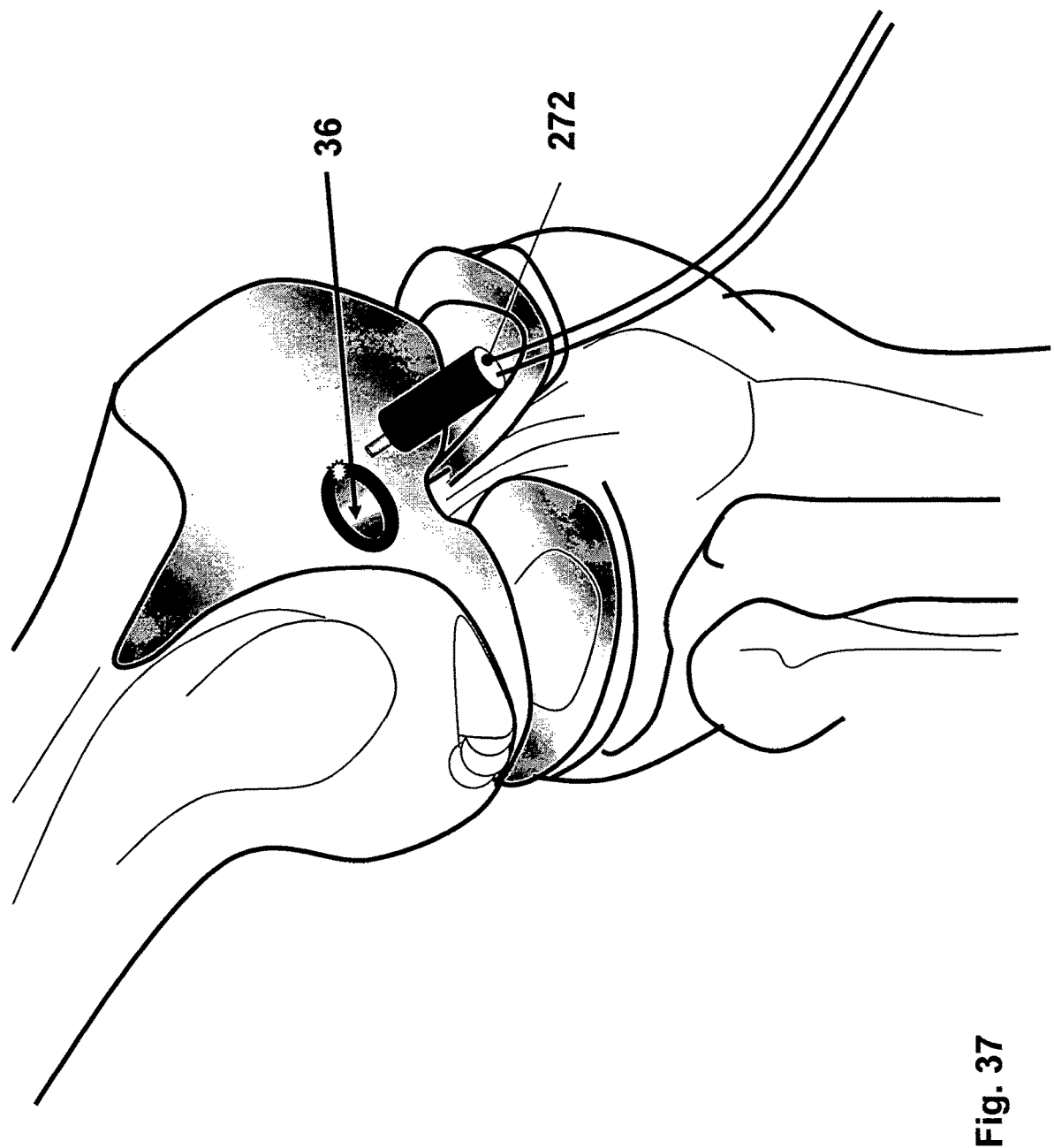
FIG. 37 illustrates a procedure during arthroscopic minimally invasive surgery wherein an energy source is applied to seal the cartilage interface.

Since the delivery system of the laser beams can be small, the procedure described above can be used for both open knee surgery (FIG. 34) and minimally invasive arthroscopic surgery, such as the procedure of repairing the cartilage defect on the femoral condyle illustrated in FIG. 35-FIG. 37. During an arthroscopic surgery, a shaped bore can be created using a shaped coring device (259 and 268), a photoactive dye can be applied in the shaped bore and on the circumferential surface of the cartilage graft, cartilage graft can be inserted into the shaped bore using a insertion device, and an energy source can be applied to activate the photoactive dye to seal the interface between the interface of the recipient cartilage being repaired and the cartilage graft.

Optionally, in addition to sealing the interface between the recipient cartilages being repaired the cartilage graft with photoactivated crosslinking, the bore created on the defect site of the recipient cartilage tissue and the cartilage graft can be coated with additional bonding agents, such as crosslinking agents. Crosslinking agents can be used to facilitate integration of the cartilage graft and the surrounding tissue after implantation and to restore the normal fluid dynamics environment of the cartilage tissue. The crosslinking agents can be chemical or enzymatic and can be, but are not limited to, glutaraldehyde; glyceraldehyde; genipin; glucose or ribose; poly(ethylene glycol) diepoxide crosslinker; poly(ethylene glycol) diglycidyl ether; EDC and NHS, transglutaminase; lysyl oxidase family; hexamethylene diisocyanate (HMDIC); dimethyl suberimidate (DMS); dimethyl-3-3'-dithiobispropionimidate (DTBP), or acryl azide.

EXAMPLES

Example 1

Osteochondral Plug, Straight, Step, or Dumbbell Shape

The distal end of a human femur was procured from a suitable donor, transported on wet ice to the processing facility. A picture was taken and was superimposed on a customer made grid/coordinate system to create a map of the human femoral condyle. The femoral condyle end was "cored" with a coring device or drilled with a hollow cylindrical drill bit to produce multiple cylindrical osteochondral plugs with diameter range from 5-20 mm and the length of the bone portion from 5-20 mm. The coordinate of each individual cylindrical plug was recorded according to the map. The cylindrical plugs were rinsed with isotonic saline. Then one of the cylindrical plugs was inserted into a holder, such as illustrated in FIG. 7, with the cartilage cap positioned face down and supported by the custom made bolt (60) as illustrated in FIG. 7(d, e and f). The length of the bone portion of the osteochondral plug protruding above the top of the holder was adjusted by the custom made bolt. Then set screws (57), preferably to be oriented 90 degrees apart, were engaged to further secure the osteochondral plug within the holder (63) and to adjust the centerline of the osteochondral plug to be parallel to the cutting tool centerline or cutting direction. The holder was fit into the headstock on a lathe. The end of the bone portion was trimmed so that the bottom surface of the bone portion was parallel to the superficial surface of the cartilage cap.

For crafting a dumbbell shape osteochondral plug, 5 mm length of the bone portion right underneath of the cartilage cap of the straight osteochondral plug was cut on a lathe so that the diameter of cut portion was about 70% of the rest part of the osteochondral plug. For crafting a step cylindrical shape osteochondral plug, the entire bone portion of the straight osteochondral plug was cut on a lathe so that the diameter of the bone portion was smaller than that of the cartilage cap of the osteochondral plug. During crafting, isotonic saline was sprayed on the graft through a cooling system installed on the lathe.

Example 2

Osteochondral Plug with Gaps, Hollow Cylinder, or Multiple Small Cylindrical Channels The osteochondral plugs, crafted to be straight, step cylindrical, or dumbbell shape as illustrated in Example 1 can be further crafted to have channels, gaps, or slots, such as osteochondral plugs (8a, 8b, 10, or 14; 22a, 22b, 23, or 25; 30a, 30b, 31, or 33) illustrated in FIG. 2-FIG. 4. Before being inserted into a holder (63 in FIG. 7), the length of the bone portion of the osteochondral plug was measured. Then, an osteochondral plug, e.g. a dumbbell shape cylindrical plug with 14 mm maximum diameter and 10 mm minimum diameter, was inserted into a holder with the cartilage cap positioned to face down and supported by the custom made bolt (60), as illustrated in FIG. 7(f).

The length of the bone portion of the osteochondral plug protruding above the top of the holder was adjusted by the custom made bolt (60). Then set screws (57), preferably to be oriented 90 degrees apart, were engaged to further secure the osteochondral plug within the holder (63) and to adjust the centerline of the osteochondral plug to be parallel to the cutting tool centerline or cutting direction. The holder was fit vertically, i.e., with the osteochondral bone portion facing up, into the clamp fixed on the x-y table of the drilling/milling machine so that it could move in a horizontal or cross direction.

An osteochondral plug with gaps as illustrated in 22a in FIG. 3 was crafted by adjusting the holder's height so that the cartilage and bone interface of the osteochondral plug was at the same height of the end of the endmill. Alternatively, the end of the endmill may be adjusted to be at the same height as the position chosen at the deep, middle or superficial region of the cartilage cap of the osteochondral plug, if the gaps are designed to occupy portion of the cartilage cap. The diameter of the endmill was 5 mm and smaller than the width of the slots (64) on the holder. By moving the holder (63) horizontally along the x direction, the endmill moved through the slots created on the holder and cut through the bone portion of the osteochondral to obtain a gap (9). Again, by moving the holder along the y direction, the endmill moved through the slots (64) created on the holder and cut through the bone portion of the osteochondral to obtain another gap (9) so that two gaps form 90 degree angles along the entire length of the bone portion up to the cartilage and osteochondral bone interface. Similar milling procedures were conducted to craft gaps that were parallel to the center line of the osteochondral plug and parallel to each other (22b) as illustration in FIG. 3.

The osteochondral plug with a hollow cylinder on the bone portion (23) as illustration in FIG. 3 was crafted by adjusting the holder fixed on a clamp on an x-y table so that the centerline of the cylindrical bone portion of the osteochondral plug was the same as that of the drilling bit. The diameter of the drill bit was chosen to be 8 mm. The center hole was first crafted by drilling down with a drill bit. The depth of the drill bit traveled was set to be the same as the length of the bone of portion of the osteochondral plug. After finishing drilling, the flat end of the center hole was created by milling with an endmill that has the same diameter as the drill bit. Alternatively, the end of the endmill may be adjusted to be at the same height as the position chosen at the deep, middle or superficial region of the cartilage cap of the osteochondral plug, if the center hole is designed to occupy portion of the cartilage cap.

The osteochondral plug with multiple small channels (15) along the whole length of the bone portion up to the cartilage and osteochondral bone interface (25) as illustrated in FIG. 3 was crafted by adjusting the holder fixed on a clamp on an x-y table so that the centerline of the cylindrical bone portion of the osteochondral plug was parallel to the drilling bit. The diameter of the drill bit was chosen to be 1 mm. The center of the first drilling was along the centerline of the osteochondral plug. The rest of the drilling centers were on the circle of 6 mm diameter from the first drilling center and 60 degree apart along the circle. The depth of the drill bit traveled was set to be the same as the length of the bone portion of the osteochondral plug. After finishing drilling, the flat end of the channels was created by milling with an endmill that has the same diameter as the drill bit. Alternatively, the end of the endmill may be adjusted to be at the same height as the position chosen at the deep, middle or superficial region of the cartilage cap of the osteochondral plug, if the channels are designed to occupy portion of the cartilage cap. During crafting, isotonic saline was sprayed on the graft through a cooling system installed on the milling/drilling machine.

Example 3

Osteochondral Plug with Channels at the Cartilage/Bone Interface

The osteochondral plugs, crafted to be straight, step cylindrical, or dumbbell shape as illustrated in Example 1 can be further crafted to have channels at the cartilage cap and bone portion interface, such as osteochondral plugs (12, 24, or 32) illustrated in FIG. 2-FIG. 4. Before being inserted into a holder, the length of the bone portion of the osteochondral plug was measured. Then, the osteochondral plug, e.g. a step cylindrical plug with 10 mm diameter at the bone portion, was inserted into a holder (61), with the cartilage cap positioned to face up and the bottom of the bone portion was supported by the custom made bolt (60) as illustrated in FIG. 8(*e*). The length of the osteochondral plug protruding above the top of the holder was adjusted by the custom made bolt. Then four set screws (57), preferably oriented 90 degrees apart, were engaged to further secure the osteochondral plug within the holder (61) and to adjust the superficial surface of the cartilage cap on the osteochondral plug to be parallel to the bottom surface of the custom made bolt (60). The holder was fixed horizontally, i.e. with centerline of the osteochondral plug being parallel to the horizontal direction, into the clamp that was fixed on the x-y table of the drilling/milling machine so that it can move in a horizontal or cross direction. One set of slots (62) on the holder (61) was positioned directly facing the drill bit. The diameter of the drill bit was chosen to be 5 mm. The center of the drilling on the graft was set to be 3 mm lower than the cartilage/bone interface along the longitudinal direction of the osteochondral plug. The drill bit passed the top slot and drilled through the bone portion to form a through channel. Then the channel was further milled to obtain a flat surface within the channel at the cartilage/bone interface to expose the deep region of the cartilage cap.

After finishing crafting the first channel, the holder with osteochondral plug inside was rotated 90 degrees to expose the second set of slots (62). Then the second channel was crafted using the same procedure that was used to cut the first channel. During crafting, isotonic saline was sprayed on the graft through a cooling system installed on the milling/drilling machine.

Example 4

Osteochondral Plug with Multiple Channels or a Slot at the Cartilage/Bone Interface The osteochondral plugs, crafted to be straight, step cylindrical, or dumbbell shape as illustrated in Example 1 can be further crafted to have multiple channels or a slot at the cartilage cap and bone portion interface, such as osteochondral plugs (16 or 18; 26 or 27; 34 or 35) illustrated in FIG. 2-FIG. 4. Before being inserted into a holder, the length of the bone portion of the osteochondral plug was measured. Then, the osteochondral plug, e.g. a step cylindrical plug with 10 mm diameter at bone portion, was inserted into a holder (54), with the cartilage cap positioned to face up and the bottom of the bone portion was supported by the custom made bolt (60) as illustrated in FIG. 9(*e*). The length of the osteochondral plug which protruded above the top of the holder was adjusted by the custom made bolt. Then four set screws (57), preferably oriented 90 degrees apart, were engaged to further secure the osteochondral plug within the holder (54) and to adjust the superficial surface of the cartilage cap on the osteochondral plug to be parallel to the bottom surface of the custom made bolt (60). The holder was fixed horizontally, i.e. with centerline of the osteochondral plug being parallel to the horizontal direction, into the clamp that was fixed on the x-y table of the drilling/milling machine so that it can move in a horizontal or cross direction. The set of slots (56) was positioned directly facing the drill/mill bit. The diameter of the drill bit was chosen to be 2 mm. For osteochondral plugs with multiple channels (16, 26, or 34) as illustrated in FIG. 2-FIG. 4, the center of the first drilling on the graft was set to be the cross of the center along the length of the slot (56) on the holder and 1 mm lower than the cartilage/bone interface along the longitudinal direction of the osteochondral plug. The drill bit passed through the slot (56) and drilled through the bone portion at the cartilage/bone interface.

Then the rest of the channels were created along the length of the slot. The distance between the centers of the channels was kept at 2.5 mm. For osteochondral plugs with a slot (18, 27, or 35) as illustrated in FIG. 2-FIG. 4, the center of the first drilling on the graft was set to be the cross of the center along the length of the slot on the holder and 1 mm lower than the cartilage/bone interface along the longitudinal direction of the osteochondral plug. The drill bit passed though the slot (56) and drilled through the bone portion at the cartilage/bone interface. Then the drill bit was replaced with a same diameter mill bit. The slot (19) on the osteochondral plug (18, 27, or 35) was created by milling along the length of the slot (56) on the holder. The total length of the slot on the osteochondral plug was 6 mm.

Example 5

Embossing of Circumferential Surface of the Cartilage Cap

The circumferential area of the cartilage portion of an osteochondral plug (as illustrated in example 1-4) or a cartilage disc can be further crafted to maximize the circumferential surface and contact areas between the recipient articular cartilage being repaired and the articular cartilage graft, as illustrated in FIG. 6, to facilitate integration of the graft tissue to the recipient tissue. A crafted osteochondral plug, such as plug (38), with tapered cylindrical cartilage cap, was further crafted to maximize circumferential surface area by embossing. A custom made tapered cylindrical stainless steel die, which had a cross line pattern along the longitudinal and the circumferential direction and with 1 mm distance between the lines, was mounted on the cutting tool fixture of the lathe. The osteochondral plug was fixed in a holder that held the bone portion of the plug inside. The entire cartilage cap protruded outside of the holder. The holder was fixed on the headstock of the lathe. The headstock was set to turn at low speed and the die was push against the cartilage cap until a 360 degree rotation was obtained.

Example 6

Microperforation of Circumferential Surface of the Cartilage Cap

The circumferential area of the cartilage portion of an osteochondral plug (as illustrated in Example 1-Example 4) or a cartilage disc can be microperforated to facilitate in situ cell migration from the surrounding tissue to the cartilage graft. The osteochondral plug was fixed in a holder that held the bone portion of the plug inside. The entire cartilage cap protruded outside of the holder. The holder was fixed horizontally, i.e. with centerline of the osteochondral plug being parallel to the horizontal direction, into the clamp fixed on the x-y table of the drilling/milling machine so that it could move horizontal or cross direction. A comb of custom made needles, with outer diameter of 350 μm and 1 mm apart, was fixed on the chuck of the drilling/milling machine with a custom made adaptor. The total width of the comb was 9 mm. The punch line was set to be the half of the depth of the cartilage cap and parallel to the cartilage/bone interface. The comb of needles passed through the entire cartilage cap.

Example 7

Cleaning and Disinfecting an Osteochondral Plug Using Centrifugal Force

The distal end of a human femur was procured from a suitable donor, transported on wet ice to the processing facility. A picture was taken and was superimposed on a customer made grid/coordinate system to create a map of the human femoral condyle. The femoral condyle end was "cored" with a coring device or drilled with a hollow cylindrical drill bit to produce multiple cylindrical osteochondral plugs with diameter range from 5-20 mm and the length of the bone portion from 5-20 mm. The coordinate of each individual cylindrical plug was recorded according to the map. The osteochondral plugs were further crafted into step cylindrical shape and with a slot at the cartilage and bone interface as illustrated in Example 4. The crafted osteochondral plugs with diameters of 14 mm at the cartilage portion and diameter of 10 mm at the bone portion were placed in a processing chamber (75 in FIG. 13*a*). The inferior surface facing the osteochondral bone portion of the cartilage cap was placed against the top surface the porous ring (85) as illustrated in FIG. 13*a*.

The bone portion of each osteochondral plug was inserted through the center hole of the porous ceramic ring (85) and fit into the bottom portion of the step cylinder hole with the rubber ring (89) on the peripheral surface that created a tight seal. After closing two caps (76 and 79) at the top and bottom of the processing chamber, the chamber was centrifuged at 1000 rcf for 15 minutes at ambient temperature. The bone marrow contained in the cancellous bone part of the osteochondral plug was induced to migrate into the bottom of the processing chamber and discarded. Two hundred and fifty milliliters of AlloWash® solution was transferred into the top portion of the processing chamber. The chamber was centrifuged at 1000 rcf for 1 hour to force the fluid pass through the grafts. Then the solution in both the top and the bottom portion of the chamber was removed and the bottom cap was closed. Two hundred and fifty milliliters of sterile distilled water containing antibiotics were transferred into the top portion of the chamber. The chamber was centrifuged at 1000 rcf for 30 minutes. The solution in both the top and the bottom portion of the chamber was removed and the bottom cap was closed. Two hundred and fifty milliliters of isotonic saline solution was transferred into the top portion of the processing chamber. The chamber was centrifuged at 1000 rcf for 15 minutes. After twice saline wash, the osteochondral plugs were ready for devitalization process.

Example 8

Cleaning and Disinfecting a Hemicondyle Using Vacuum Pressure and Sonication

The distal end of a human femur was procured from a suitable donor, transported on wet ice to the processing facility, and the condyle end was bisected into two hemicondyles. Each hemicondyle was placed in a glass container containing 1 liter of AlloWash® solution and sonicated at 100 Hz for 2 hours. After sonication, the hemicondyle and AlloWash® solution was transferred into a processing chamber similar to the one shown in FIG. 14. The bone portion of each hemicondyle was inserted into an insert that had a large center hole with the rubber ring (created a tight seal). The entire hemicondyle was immersed in the processing solution. The bottom port of the chamber (78) was connected to tubing that led to a collection beaker (94), which was connected to a pump (95). The pump applied a vacuum pressure between about 0 to about 20 MPa to the space inside of the chamber. After vacuuming for 2 hours, all AlloWash® solution was pulled out of the chamber. One liter of sterile ultra-pure water containing antibiotics was transferred into the top portion of the chamber. Vacuum pressure between about 0 to about 20 MPa was applied to the chamber for 1 hour. The solution was pulled into the bottom portion of the chamber and removed by vacuuming. One liter of sterile ultra-pure water was transferred into the top portion of the processing chamber. Vacuum pressure between about 0 to about 20 MPa was applied to the chamber for 30 minutes. The solution was pulled into the bottom portion of the chamber and removed by vacuuming. After washing for two more times, the hemicondyle was ready for devitalization process.

Example 9

Devitalizing an Osteochondral Plug Using Centrifugal Force

Ten cleaned and disinfected step cylindrical osteochondral plugs with channels as illustrated in Example 2, with diameter of 14 mm at the cartilage portion and diameter of 10 mm at the bone portion, were positioned in a processing chamber (75 in FIG. 13*a*). The bone portion of each osteochondral plug was inserted through the center hole of the porous ceramic ring (85) and fit into the bottom portion of the step cylinder hole with the rubber ring (89) on the peripheral surface to create a tight seal. One hundred milliliters of pretreatment solution containing 1 unit/mL of chondroitinase ABC in Tris/NaAc buffer was transferred into the top part of the chamber. The chamber was centrifuged at 1000 rcf for 6 hours at 37° C. The pretreatment solution in both the top and the bottom portion of the chamber was removed and the bottom cap (79) was closed.

One hundred milliliters of isotonic saline solution was transferred into the top portion of the processing chamber. The chamber was centrifuged at 1000 rcf for 15 minutes. After two more saline washes, five hundred milliliters of extracting solution was transferred into the top portion of the processing chamber (FIG. 13a). The extracting solution consisted of 50 mM Tris-HCl/Tris base (pH 8.0), 2 mM $MgCl_2$, 16 mM N-lauroyl sarcosinate, 12 units/mL of endonuclease (Benzonase®, EM Industries, Inc.), and antibiotics sufficient to disinfect the tissue. The amount of endonuclease included in the solution was calculated based on the weight of tissue to be devitalized and the total volume of the extracting solution. The processing chamber containing osteochondral plugs was centrifuged at 37° C. for 12 hours utilizing 1000 rcf to facilitate penetration of the fluid into the osteochondral plugs. Following completion of the devitalization process, the chamber was drained of extracting solution and replaced with 500 mL of isotonic saline. The chamber was centrifuged at 1000 rcf for 30 minutes. The saline wash was repeated two more times.

Next, the chamber was drained of saline and 250 mL of 77% (v/v) glycerol was transferred into the top portion of the chamber. The chamber was incubated and centrifuged at 1000 rcf for 2 hours at ambient temperature. The glycerol was drained from the chamber. The devitalized osteochondral plugs were transferred into an inner bag (145 in FIG. 18b(e)) with two ports (147) that sealed with Luer lock caps (148), sealed under vacuum on one edge (146), placed in an outer bag (150) and sealed. Then, the osteochondral plugs in storage bags were sent for gamma irradiation at about 15 to about 18 kGy or stored at −80° C. Samples from devitalized osteochondral plugs were used for histology assessment, DNA quantification, or sulfated glycosaminoglycan (GAG) quantification.

Example 10

Devitalizing a Fibrocartilage Disc Using a Fluid Flow Through System

Ten fibrocartilage discs isolated from menisci of a cadaver donor, 10 mm in diameter, were positioned into the slots on the stainless steel porous platens on an insert (274) in a processing chamber as illustrated in FIG. 16a. The superficial surfaces of all discs were parallel to the fluid flow direction. The processing chamber was connected to the medical grade disposable tubing with 3-way stopcocks inserted in-line, a peristaltic pump and, processing solution reservoirs. The Luer lock (92) and the lid (97) were screwed down tightly to engage the o-ring thereby eliminating leakage from the chamber (96). The hydrophobic adsorbent resin and anion exchange resin were added to the resin chamber (102). There was an o-ring at the top and bottom of the resin chamber to ensure a secure fit between the resin chamber and the resin housing to force the flow of sterile ultra-pure water through the resin chamber. The tubing was attached to the sipper devices (106 and 109) such that the return flow entered the side with the shortest spout and the outbound flow was pulled through the longest spout. The tubing was placed on the rollers of the peristaltic pump and clamp lowered to hold the tubing in place.

Then, five hundred milliliters of pretreatment solution containing 1 unit/mL of chondroitinase ABC in Tris/NaAc buffer in solution reservoir (103) was drawn up from the long spout of the sipper (106), proceeded through the port (105), continued past stopcock (113) and tubing through the roller assembly of the pump (95) through port (98), proceeded through the cartilage graft and insert, then out the bottom of the chamber and through port (78) and continues past stopcocks (114 and 115 and 116), then into the sipper (106) through the short spout and port (107) by using a second pump (117). This cycle continued at 250 mls/minute for 16 hours at 37° C. Then one pump (95) was stopped and another pump (117) was on until the processing chamber was empty. Stopcocks (113, 114, 115, and 116) were turned to redirect the flow to and from the sterile ultra-pure water reservoir (104) and to direct the flow through the resin housing chamber (102). The pumps (95 and 117) were turned on again and the chamber was filled by water exiting sipper (108) out the long spout, into the tubing through stopcock (113), and through the roller pump (95), into the processing chamber (96) through port (98) and proceeds through the cartilage graft and insert, then out the bottom of the chamber and through port (78) and continued past stopcock (114) which directs the flow of water into the resin chamber (102) and out of port (111) and stopcocks (115 and 116) through the tubing and into sipper (109) via the short spout and port (110) and into the water reservoir (104) by using a second pump (117). This cycle continued at 250 mls/minute for 16 hours at ambient temperature. The pressure within the processing chamber was monitored by a pressure gauge (100) that was connected to a port (99). The pretreatment solution reservoir was replaced by an extracting solution reservoir. After removing water from processing chamber, the stopcocks connected to the reservoir containing 500 milliliters of extracting solution was opened and the extracting solution proceeded through the processing chamber at 250 mls/minute for 16 hours at ambient temperature.

The extracting solution consisted of 50 mM Tris-HCl/Tris Base (pH 8.0), 2 mM $MgCl_2$, 0.5% CHAPS, 12 units/mL of endonuclease (Benzonase™, EM Industries, Inc.), and antibiotics sufficient to disinfect the tissue.

Following completion of the devitalization process, the chamber was drained of extracting solution and the stopcock connected to the reservoir containing sterile ultra-pure water was opened. Ultra-pure water proceeded through the processing chamber at 250 mls/minute for 16 hours at ambient temperature. The processing chamber was drained of water and the water reservoir was replaced by a storage solution reservoir. The stopcock connected to the reservoir containing 500 mL of 77% (v/v) glycerol was opened. Glycerol proceeded through the processing chamber at 50 mls/minute for 6 hours at ambient temperature. Then glycerol was drained from the chamber. The devitalized fibrocartilage discs were transferred into an inner bag (145 in FIG. 18b(e)) with two ports (147) that sealed with Luer lock caps (148), sealed under vacuum on one edge (146), placed in an outer bag (150) and sealed. Then, the fibrocartilage discs in storage bags were sent for gamma irradiation at about 15 to about 18 kGy and stored at −80° C. Samples from devitalized fibrocartilage discs were used for histology assessment, DNA quantification, or sulfated glycosaminoglycan (GAG) quantification.

Example 11

Devitalizing Articular Cartilage Slices in an Orbital Shaker

Twenty articular cartilage slices isolated from femoral condyle and cut to be 350-500 micrometer in thickness and 5 to 10 mm in diameter were individually placed in 20 microcentrifuge tubes separately. One milliliter of isotonic saline solution was transferred into each tube. The microcentrifuge tubes were incubated at 37° C. in an orbital shaker for 15 minutes at 1000 rpm. After two more saline washes, one milliliter of extracting solution was transferred into each microcentrifuge tube. The extracting solution consisted of 50 mM Tris-HCl/Tris Base (pH 8.0), 2 mM $MgCl_2$, 16 mM N-lauroyl sarcosinate, 12 units/mL of endonuclease (Benzonase®, EM Industries, Inc.), and antibiotics sufficient to disinfect the tissue. The microcentrifuge tubes containing articular cartilage slices were incubated at 37° C. in an orbital shaker for 16 hours at 1000 rpm.

Following completion of the devitalization process, the tubes were drained of the extracting solution and replaced with 1 mL of isotonic saline. The tubes were incubated at 37° C. in an orbital shaker for 15 minutes at 1000 rpm. The saline wash was repeated two more times. The tubes were drained of extracting solution and replaced with 1 mL of 77% (v/v) glycerol. The tubes were incubated at 37° C. in an orbital shaker for 2 hours at 1000 rpm at ambient temperature.

The devitalized articular cartilage slices were then transferred into an inner bag (145 in 18b(e)) with two ports (147) that sealed with Luer lock caps (148), sealed under vacuum on one edge (146), placed in an outer bag (150) and sealed. Samples from devitalized fibrocartilage discs were used for histology assessment, DNA quantification, or sulfated glycosaminoglycan (GAG) quantification.

Example 12

Devitalizing Osteochondral Plugs and Cartilage Slices Using Cyclic Hydrodynamic Pressure Five cleaned and disinfected osteochondral plugs, with diameter of 14 mm at the cartilage portion and diameter of 10 mm at the bone portion, and ten articular cartilage slices, with diameter of 14 mm and thickness of 500 micrometer each, were positioned in a processing chamber (FIG. 17a). The cartilage slices were stacked together between two ceramic porous platens that had the curvature of target defect site, and placed within a confining ring (124). The bone portion of each osteochondral plug was inserted through the center hole of the porous stainless steel platen and fit into the bottom portion of the step cylinder hole with the rubber ring on the peripheral surface to create a tight seal. Five hundred milliliters of pretreatment solution containing 1 unit/mL of chondroitinase ABC in Tris/NaAc buffer was transferred into the processing chamber, as well as the rigid tubing and the bottom part of the pressurization chamber (FIG. 17a). Compressed air/gas was driven by a piston (132) and passed through the connector (286) to compress the flexible membrane (193). The piston was driven by a computer controlled cam to move up and down to create a cyclic pressure on the flexible membrane that transferred the pressure to the processing chamber. The pressure was monitored using two pressure gauges (100) and regulated by two valves (131). The compressed air/gas was made of sterile 5% $CO_2$ in air.

The osteochondral plugs and cartilage discs were pretreated with chondroitinase ABC under cycles of hydrodynamic pressure of 0 and 6 MPa for 6 hours at frequency of 1 Hz and at 37° C. The pretreatment solution in the processing chamber was removed. Five hundred milliliters of isotonic saline solution was transferred into the processing chamber. The grafts were then pressurized again under cyclic hydrodynamic pressure for 1 hour. After the saline drained from the processing chamber, five hundred milliliters of extracting solution was transferred into the processing chamber. The extracting solution consisted of 50 mM Tris-HCl/Tris Base (pH 8.0), 2 mM $MgCl_2$, 0.5% CHAPS, 12 units/mL of endonuclease (Benzonase®, EM Industries, Inc.), and antibiotics sufficient to disinfect the tissue. The osteochondral plugs and cartilage slices were processed under cycles of hydrodynamic pressure of 0 and 6 MPa for 16 hours at ambient temperature.

Following completion of the devitalization process, the processing chamber was drained of extracting solution and replaced with 500 mL of isotonic saline. The grafts were pressurized again under cyclic hydrodynamic pressure for 1 hour. The saline wash was repeated two more times. The chamber was drained of saline and 500 mL of 77% (v/v) glycerol was transferred into the processing chamber. The grafts were pressurized again under cyclic hydrodynamic pressure for 2 hours at ambient temperature. Then, the glycerol was drained from the chamber.

Figure 18B:
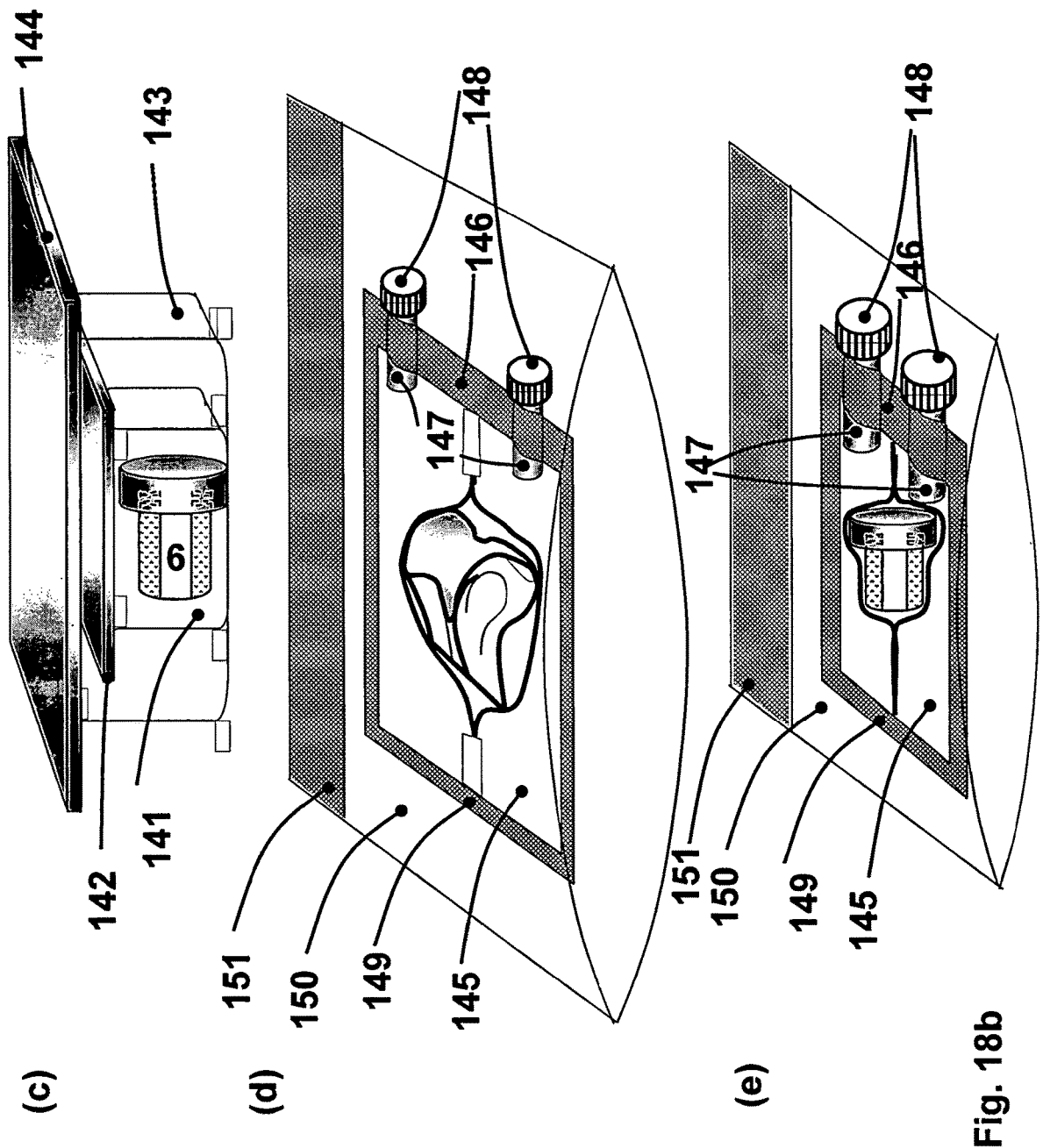
FIG. 18b illustrates an embodiment of packaging device where excess storage solution is removed and the wet cartilage grafts are packaged with or without vacuum and stored.

The devitalized osteochondral plugs or the stack of cartilage slices along with the contoured porous platen were transferred into an inner sealed box (141) and the inner box was placed in an outer box (143) and sealed (c in FIG. 18b). The osteochondral plugs in storage boxes were sent for gamma irradiation at about 15 to about 18 kGy and/or stored at −80° C. Samples from devitalized osteochondral plugs or cartilage slices were used for histology assessment, DNA quantification, or sulfated glycosaminoglycan (GAG) quantification.

Example 13

Devitalization of Articular Cartilage Using Chondroitinase ABC and/or CHAPS Made of Benzonase on a Shaker Frozen human articular cartilage obtained from cadaver with donor consent was used for the experiments. The 5-7 mm diameter cartilage discs without subchondral bone were pretreated with a pretreatment solution composed of 1 unit/mL of chondriotinase ABC in 50 mM Tris/60 mM NaAc buffer supplemented with protease inhibitors and bovine serum albumin at 37° C. and 1,000 rpm on a shaker for 24 hours. The cartilage discs were washed with isotonic saline for 15 minutes at 37° C. for a total of three times. Two samples were stored at 4° C. as chondroitinase controls. The rest of samples were devitalized in an extracting solution, composed of 0.5% CHAPS, 11.5 units/mL Benzonase, 50 mM Tris, and 2 mM $MgCl_2$, at 37° C. and 1000 rpm in a shaker for 24 hours. The cartilage samples were washed twice with isotonic saline for 1 hour at 37° C.

Figure 38:
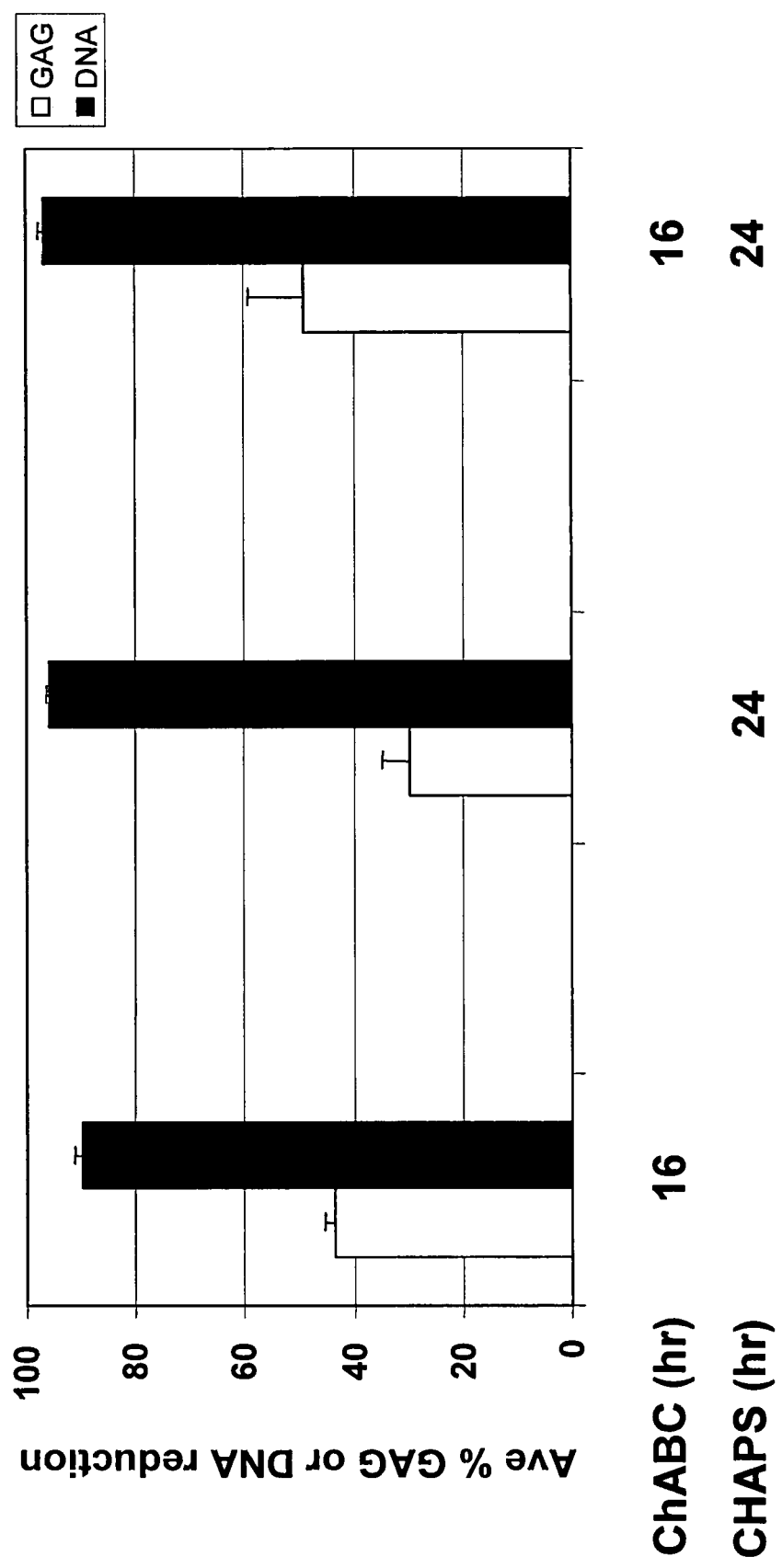
FIG. 38 illustrates the percentage of DNA and proteoglycan reduction in cartilage discs after devitalization with 0.5% CHAPS in combination with or without pretreatment with chondroitinase ABC.

The resulting cartilage was used for DNA, GAG quantification, Haematoxylin & Eosin and Safranin O staining. A Quant-it PicoGreen dsDNA kit was used to quantify the residual DNA in the cartilage. The GAG content was quantified by dimethylmethylene blue (DMMB) assay. FIG. 38 illustrates the amount of dsDNA in cartilage detected with PicoGreen reagents. The percentage of DNA reduction was relative to the cryopreserved cartilage grafts from the same donor.

The groups treated with chondroitinase or CHAPS/Benzonase showed significantly lower residual dsDNA compared to cryopreserved control. The combination of chondroitinase ABC and CHAPS/Benzonase gave the most DNA reduction (>98%).

Figure 39:
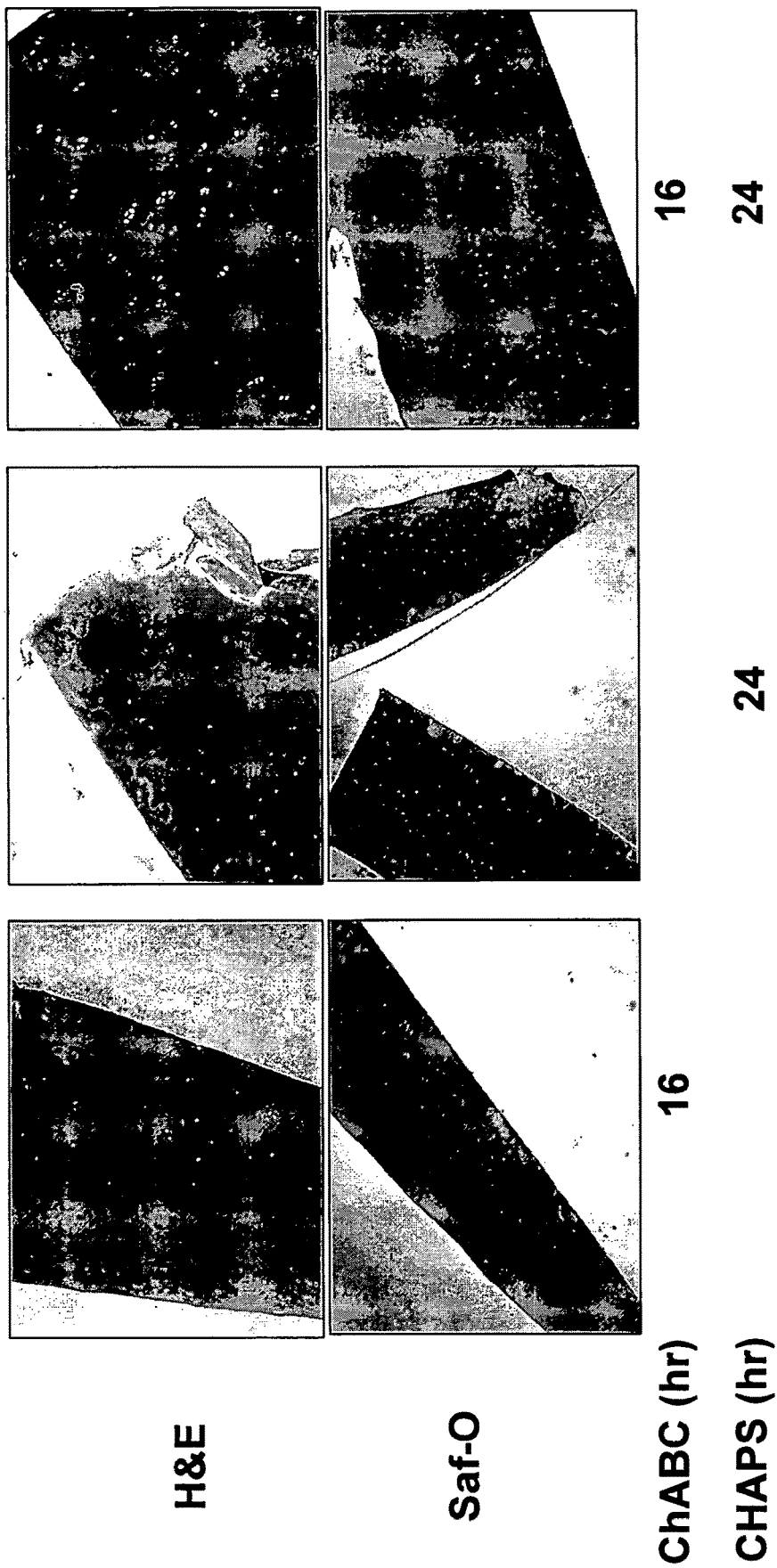
FIG. 39 illustrates the H&E and Safranin O staining of cartilage discs after devitalization with 0.5% CHAPS in combination with or without pretreatment of chondroitinase ABC.

The histology sections, stained with Haematoxylin & Eosin and Safranin O, showed that significant reduction of nucleus staining was found in cartilage groups treated with chondroitinase ABC and CHAPS/Benzonase. Inter-territorial matrix removal was found in cartilage treated with chondroitinase ABC and CHAPS/Benzonase, while territorial matrix reduction was found at the surfaces that were exposed to the pretreatment or extracting solution directly (FIG. 39).

Example 14

Microperforation of the Cartilage Cap with Agarose Bead Immobilized TPCK Trypsin after Devitalization After devitalization, the cartilage portion of an osteochondral plug (as illustrated in Example 1-Example 4) or a cartilage disc can be microperforated to facilitate recellularization in vitro, vivo, and in situ. Five cylindrical osteochondral plugs, 7 mm in diameter and 10 mm in length, were placed in a sterile glass beaker. Five milliliters of agarose beads immobilized with TPCK trypsin (Pierce, Rockford, Ill.) were washed with a 0.1 $NH_4HCO_3$ (pH 8.0) digesting buffer. The beads were then resuspended in 14 ml of the digest buffer, mixed, and transferred into a beaker with osteochondral plugs. The beaker was then placed on an orbital shaker at 37° C. for 60 minutes.

During the incubation period, the beaker was taken out of the incubator every 15 minutes, sonicated for 2 minutes at 37° C., and returned back to the orbital shaker in the incubator. After 60 minutes of incubation and agitation, the osteochondral plugs were removed from the trypsin bead solution and placed individually in a clean 15 ml conical tube with cartilage cap facing down. The osteochondral plugs were spun at 400 rcf for 10 minutes to remove the excessive fluid.

Then the osteochondral plugs were transferred into a clean sterile beaker and incubated with 30 ml of DMEM supplemented with 10% heat inactivated FBS or human serum for 15 minutes to inactivate the trypsin activity. This trypsin inactivation step was repeated twice with fresh DMEM supplemented with 10% heat inactivated FBS or human serum. Next, the osteochondral plugs were washed with phosphate buffered saline three times, and placed individually in a clean 15 ml conical tube with the cartilage cap facing down. The osteochondral plugs were spun at 400 rcf for 10 minute to remove excessive fluid.

Example 15

Bioactive Growth Supplements Coating on an Osteochondral Plug

Carboxylic acid groups of Heparin (sodium alt, 170 USP units/mg, Sigma Aldrich) were activated with EDC (Sigma Aldrich) and NHS (Sigma Aldrich). Ten milligrams of heparin was activated with 10 mg EDC/6 mg NHS in 5 ml of 0.05 M 2-morpholinoethnesulfonic acid (MES) buffer (pH 5.6) for 10 minutes at 37° C. A straight cylindrical osteochondral plug (7 mm in diameter and 10 mm in length) was immersed in the activated heparin solution and shaken at 200 rpm on an orbital shaker at ambient temperature. After 4 hours of reaction, the osteochondral plug was rinsed in 0.05 MES buffer and pH 7.4 phosphate-buffered saline (PBS) three times.

Figure 40:
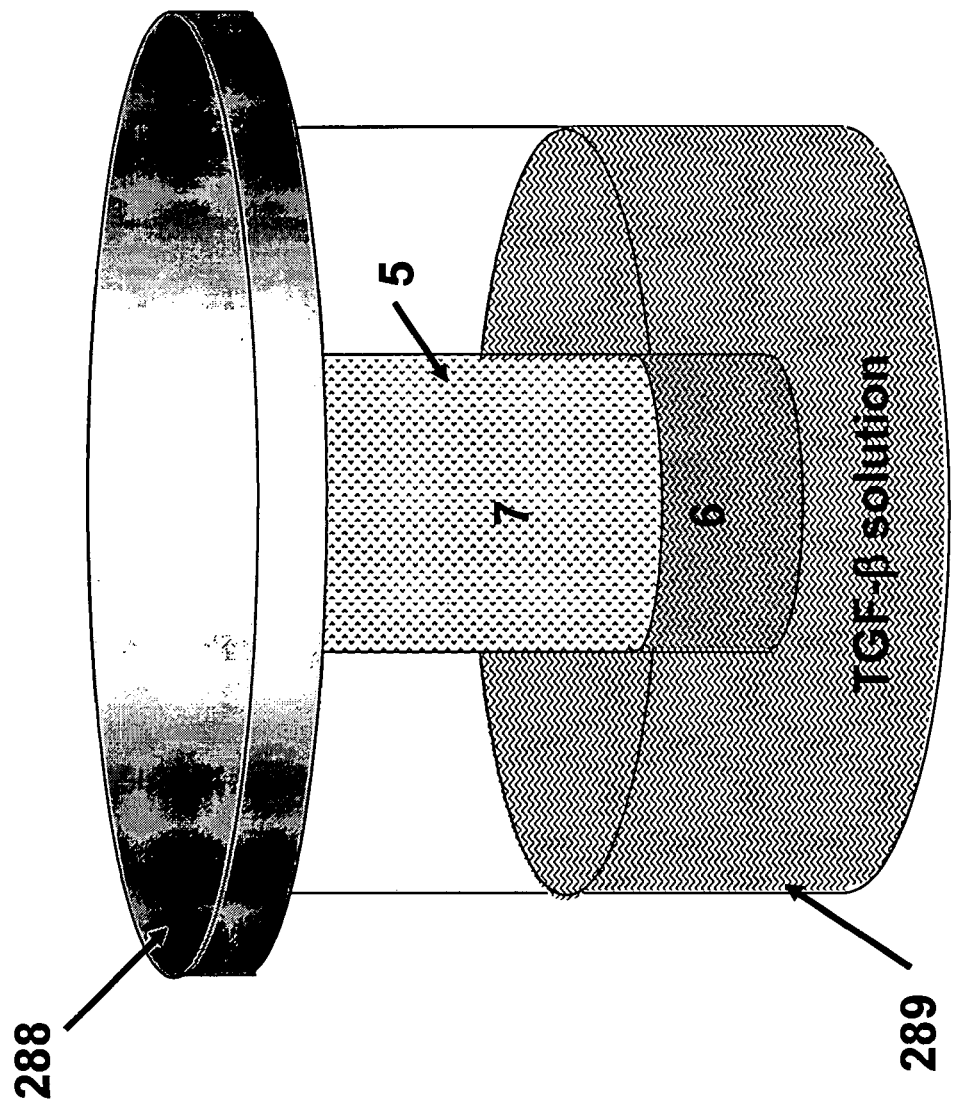
FIG. 40 illustrates a procedure for a coating growth factor on the cartilage portion of an osteochondral plug.

In order to induce chondrogenesis, the bone portion of the heparin immobilized osteochondral plug (5) was fastened onto a plate (288) (FIG. 40). The osteochondral plug was inverted and inserted into a container (289) that contained TGF-β solution. The level of TGF-β solution was adjusted to just cover the entire cartilage cap. The cartilage cap was incubated in the TGF-β solution and agitated at 60 rpm on an orbital shaker for 4 hours at room temperature.

Figure 41:
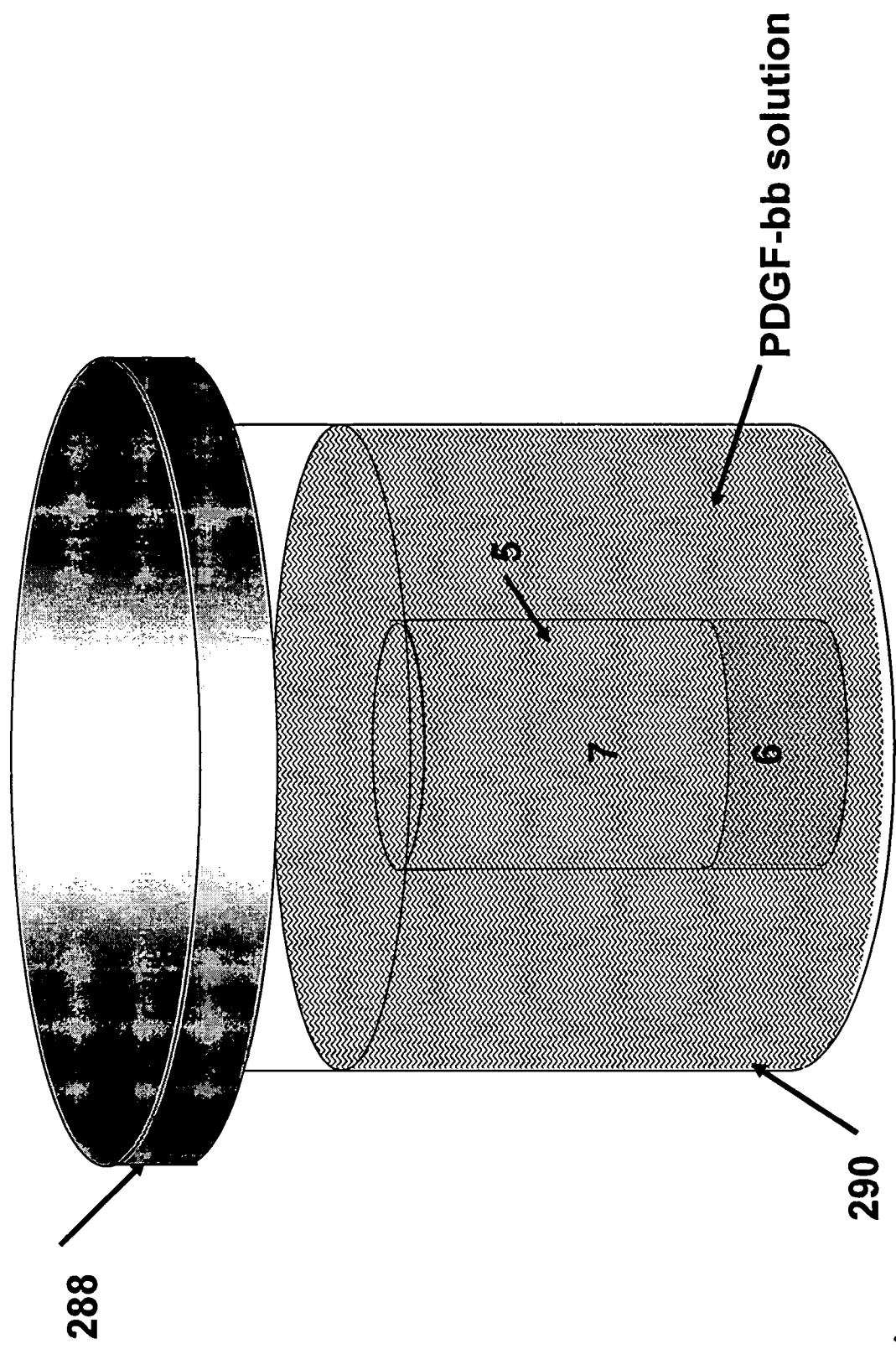
FIG. 41 illustrates a procedure for a coating growth factor on the entire osteochondral plug.

The TGF-β coated osteochondral plug was removed from the plate and transferred into a container (290) that contained PDGF-bb in PBS solution (0.2 mg/ml) (FIG. 41). The whole osteochondral plug was incubated with PDGF-bb solution and agitated at 200 rpm on an orbital shaker for 4 hours at room temperature. The bioactive growth supplement coated osteochondral plug was transferred into a clean 15 ml centrifuge tube and spun quickly to remove excessive fluid. Then the osteochondral plug was freeze dried, placed in a bottle, sealed, placed in an outer container, sealed again, and stored at −80° C.

Example 16

Recellularization of Osteochondral Plug In Situ with Bone Marrow

A devitalized osteochondral plug with a slot, such as the plug (35) in FIG. 4, stored in a vacuum sealed bag was retrieved and rinsed with isotonic saline. Freeze dried demineralized bone matrix was prepared. Two or three milliliter of bone marrow aspirate was obtained from the tibia and femur of one or two mice and mixed with 6 ml of heparin in TC 199 and constantly mixed. The bone marrow was then filtered through a double thickness of sterile gauze and through a 100 μm nylon filter. The devitalized osteochondral plug was mixed with 10 ml of the filtered bone marrow until implantation to facilitate the bone marrow stromal cell attachment. The osteochondral plug, secured at the bottom of a 15 ml conical tube and mixed with the bone marrow suspension, was spun under a centrifugal force to promote further cell attachment. The demineralized bone matrix was then mixed with the filtered bone marrow at 1:1 ratio (volume:volume). Next, the demineralized bone matrix and bone marrow mixture was inserted into the slot on the osteochondral plug. Then the osteochondral plug was ready for implantation. Optionally, right before implantation, the demineralized bone matrix and bone marrow mixture can be also inserted into the bore created at the recipient defect site. The amount of cell attachment and cell viability were analyzed.

Example 17

Recellularization Hyaline Cartilage Disc In Situ with Chondrocyte

Autologous or allogeneic chondrocytes were isolated from non-load bearing femoral condyle and propagated in vitro in culture media that was composed of Dulbecco's Modified Essential Medium (DMEM) supplemented with 10% FBS, non-essential amino acid, 40 μg/ml proline, and antibiotics (100 U/ml penicillin and 100 μg/ml streptomycin, Invitrogen) for between 3-5 passages. A devitalized cartilage disc stored in a vacuum sealed bag was retrieved and rinsed with isotonic saline. The cartilage disc has a bore in the center, and the depth of which reaches the middle region along the depth. Cultured chondrocytes were trypsinized from the culture flask and suspended in culture media supplemented with 50 μg/ml ascorbate at $10 \times 10^6$ cell/ml density. The devitalized human hyaline cartilage disc was mixed with the 1.5 ml of the cell suspension in a 2 ml tube on a rotator located in an incubator or water bath. The cartilage and the autologous chondrocyte suspension were spun to promote further cell attachment. In addition, the demineralized bone matrix was then mixed with the chondrocyte at 1:1 ratio (volume:volume). Next, the demineralized bone matrix and chondrocyte mixture was inserted into the bore in the cartilage disc. The in situ recellularized cartilage disc was ready to be implanted. The amount of cell attachment and cell viability were then analyzed.

Example 18

Recellularization Fibrocartilage Cartilage Slices In Situ with Allogeneic Stromal Cells from Adipose Tissue Adipose tissue was obtained from a donor. The adipose tissue was rinsed with Hanks' balanced salt solution containing antibiotics (100 U/ml penicillin and 100 U/ml streptomycin) and 2.5 µg/ml amphotericin B. To isolate stromal cells, the adipose tissue was digested for 2 hours on a shaker at 37° C. in HBSS containing 0.2% collagenase (Sigma, St Louis, Mo.) and centrifuged at 1200 rcf for 10 minutes to obtain a high-density cell pellet. The cell pellet was re-suspended in red blood cell lysis buffer for 10 min at room temperature. The stromal cell pellet was collected by centrifugation, as described above, and re-suspended in a chondrogenic media, which was composed of DMEM (Invitrogen), 10% serum, 10 ng/ml TGF-β1, 1% ITS (10 µg/ml insulin, 5.5 µg/ml transferrin, 5 ng/ml selenium, 0.5 mg/ml BSA, 4.7 µg/ml linoleic acid; Sigma), 50 µg/ml ascorbate-2-phosphate, 40 µg/ml proline, 100 µg/ml pyruvate, and 100 U/ml penicillin and 100 µg/ml streptomycin (all from Invitrogen) at a cell density of $2\times10^6$/ml.

Devitalized human fibrocartilage slices stored in a vacuum sealed bag was retrieved and rinsed with isotonic saline. Each individual slice of cartilage from the same package was placed in each well of the 24-well plate. Optionally, a cloning cylinder with grease was place on top of the cartilage slice to create a seal at the peripheral. Stromal cells from adipose tissue were seeded on top of the cartilage slice within the cloning cylinder. The whole plate was centrifuged at 400 g for 5 min to facilitate the cell attachment. The cartilage slices are bonded between adjacent slices using a bonding agent and stack together. Then, the in situ recellularized cartilage slices were ready for implantation. The amount of cell attachment and cell viability were analyzed.

Example 19

Recellularization Hyaline Cartilage Slices In Situ with Allogeneic Stromal Cells from Fibrous Synovium Fibrous synovium was harvested from the inner side of the lateral joint capsule, which overlays the noncartilage areas of the lateral condyles of the femur from cadaver donors. The tissue was minced to pieces with a surgical blade, washed thoroughly with phosphate buffered saline (PBS), and digested in a collagenase solution (3 mg/ml collagenase D; Roche Diagnostics, Mannheim, Germany) in α-minimum essential medium (Invitrogen, Carlsbad, Calif.) at 37° C. After 3 hours, digested cells were filtered through a 70-µm nylon filter (Becton Dickinson, Franklin Lakes, N.J.). Nucleated cells from the tissues were plated at $10^3$ cells/cm² in a T-75 flask and cultured in DMEM, 10% FBS, 100 U/ml penicillin and 100 µg/ml streptomycin (all from Invitrogen), and 1 ng/mL basic fibroblast growth factor (bFGF) for 14 days before any passages. The same seeding density and media was kept for future passages. Then, passage 3 stromal cells were trypsinized and suspended in chondrogenic media, which was composed of DMEM (Invitrogen), 10% serum, 10 ng/ml TGF-β1, 1% ITS (10 µg/ml insulin, 5.5 µg/ml transferrin, 5 ng/ml selenium, 0.5 mg/ml BSA, 4.7 µg/ml linoleic acid; Sigma), 50 µg/ml ascorbate-2-phosphate, 40 µg/ml proline, 100 µg/ml pyruvate, and 100 U/ml penicillin and 100 µg/ml streptomycin (all from Invitrogen) at a cell density of $2\times10^6$/ml.

Devitalized human hyaline cartilage slices stored in a vacuum sealed bag was retrieved and rinsed with isotonic saline. Each individual slice of cartilage from the same package was placed in each well of the 24-well plate. One milliliter of the stromal cell suspension was added in each well of the 24-well plate. The plate was placed on a shaker and kept at 37° C. until implantation. Optionally, the whole plate was centrifuged at 400 g for 5 min to facilitate cell attachment. Then, the in situ recellularized cartilage slices were ready for implantation. The amount of cell attachment and cell viability were analyzed.

Example 20

Recellularization In Vivo in Muscle

A devitalized rabbit osteochondral plug stored in a vacuum sealed bag is retrieved and rinsed with isotonic saline. The devitalized cartilage graft is implanted in a muscle pouch of a nude mouse for 3 months. Then the cartilage disc is retrieved from the muscle, the excessive fibrous tissue surrounding the recellularized cartilage graft is trimmed off, and rinsed with isotonic saline. The in vivo recellularized rabbit osteochondral plug is analyzed for cellular infiltration by immunostaining.

Example 21

Recellularization In Vivo in a Fat Pad

A devitalized human hyaline cartilage disc without subchondral bone attached and stored in a vacuum sealed bag is retrieved and rinsed with isotonic saline. The devitalized cartilage graft is implanted in the epididymal fat pad of a nude mouse for 3 months. Then the cartilage disc is retrieved from the fat pad, trimmed off the excessive fibrous tissue surrounding the recellularized cartilage graft, and rinsed with isotonic saline. The in vivo recellularized cartilage disc is analyzed for cellular infiltration by immunostaining.

Example 22

Recellularization of Osteochondral Plug In Vitro with Allogeneic Stromal Cells from Synovium A devitalized human osteochondral plug stored in a vacuum sealed bag is retrieved and rinsed with isotonic saline. Each individual osteochondral plug is placed in a 15 ml conical tube with a custom made cap that is connected to an air/gas filter. Allogeneic stromal cells from synovium, as illustrated in Example 19, are suspended in Dulbecco's Modified Essential Medium (DMEM) supplemented with 10% FBS, and antibiotics (100 U/ml penicillin and 100 µg/ml streptomycin, Invitrogen) at a density of $2\times10^6$ cells/ml, and added into the tube to immerse the entire osteochondral plug. Then, the tube is placed on a roller, transferred into an incubator, and cultured for 24 hours. Optionally, the cell suspension and the osteochondral plug are centrifuged to facilitate cell attachment. After 24 hours of culture on a roller, the osteochondral plug is transferred into a bioreactor as illustrated in FIG. 28.

Then, the cartilage cap is placed within a confining ring (204) and sandwiched between a top porous platens (226) made of porous titanium and a bottom porous ring (241) made of cancellous bone. The entire osteochondral plug is supported by the supporting ring (248) and compressed with a loading shaft connected to a damping spring. The cartilage cap is placed within the top well, while the bone portion is placed in the bottom well of the bioreactor. The culture media in the top well of the bioreactor is chondrogenic media, which is composed of DMEM (Invitrogen), 10% serum, 10 ng/ml TGF-β1, 1% ITS (10 µg/ml insulin, 5.5 µg/ml transferrin, 5 ng/ml selenium, 0.5 mg/ml BSA, 4.7 µg/ml linoleic acid; Sigma), 50 µg/ml ascorbate-2-phosphate, 40 µg/ml proline, 100 µg/ml pyruvate, and 100 U/ml penicillin and 100 µg/ml streptomycin. The culture media in the bottom well of the bioreactor is osteogenic, and is composed of DMEM (Invitrogen), 10% serum, 100 nM dexamethasone, 10 mM β-glycerophosphate, 50 µg/ml ascorbate-2-phosphate (Sigma), and antibiotics (100 U/ml penicillin and 100 µg/ml streptomycin, Invitrogen). The compressive stress is cycled between 0-6 MPa that is controlled by the load cell and the movement of the loading shaft through a computer. The entire bioreactor is fit into an incubator. The media is circulated between the bioreactor and two media reservoirs that are pumped with filtered 5% $CO_2$ in air. The cyclic compression is conducted for 8 hrs per day. After 4 weeks of culture, the cartilage graft is ready to be transplanted. The cell morphology, viability, extracellular matrix synthesis are analyzed.

Example 23

Recellularization of Osteochondral Plug In Vitro with Allogeneic Stromal Cells from Adipose Tissue, Create Contour, Load Opposing Plugs with Loading Shaft Two devitalized human osteochondral plug with gaps, as illustrated in FIG. 4 plug (30a) and stored in a vacuum sealed bag, are retrieved and rinsed with isotonic saline. Each individual osteochondral plug is placed in a 15 ml conical tube with a custom made cap that is connected to an air/gas filter. Allogeneic stromal cells from adipose tissue, as illustrated in Example 18, are suspended in Dulbecco's Modified Essential Medium (DMEM) supplemented with 10% FBS, and antibiotics (100 U/ml penicillin and 100 µg/ml streptomycin, Invitrogen) at a density of $2 \times 10^6$ cells/ml, added into the tube to immerse the entire osteochondral plug. Then the tube is placed on a roller, transferred into an incubator, and cultured for 24 hrs. Optionally, the cell suspension and the osteochondral plug are centrifuged to facilitate the cell attachment.

After 24 hrs of culture on a roller, two osteochondral plugs are transferred into a bioreactor as illustrated in FIG. 30. The bottom of the first osteochondral plug is supported by a supporting ring (248) which is screwed into the bottom of the culture well (162) during compression. The second osteochondral plug is placed on top of the first osteochondral plug and the superficial surface of the cartilage cap of the osteochondral plugs are placed opposing each other. In order to obtain congruent contoured surfaces between two osteochondral plugs, a porous platen (279) with the target curvature according to the contour of the recipient joint is manufactured and placed between the cartilage caps of the two opposing osteochondral plugs. For confined compression, cartilage caps from both osteochondral plugs are placed in a confining ring (247) (FIG. 29). The culture media in the top and bottom wells of the bioreactor are chondrogenic media, which is composed of DMEM (Invitrogen), 10% serum, 10 ng/ml TGF-β1, 1% ITS (10 µg/ml insulin, 5.5 µg/ml transferrin, 5 ng/ml selenium, 0.5 mg/ml BSA, 4.7 µg/ml linoleic acid; Sigma), 50 µg/ml ascorbate-2-phosphate, 40 µg/ml proline, 100 µg/ml pyruvate, and 100 U/ml penicillin and 100 µg/ml streptomycin. The loading shaft is directly compressed on the bone portion of the second osteochondral plug, a solid bead (243), and a porous platen (226) to ensure the center line of the loading shaft is parallel to the centerline of the osteochondral plugs to be compressed. The loading shaft is driven by a computer controlled cam and a stepper motor to move up and down to create a cyclic compression within the bioreactor. The compressive stress is cycled between 0-6 MPa and is controlled by the load cell and the movement of the loading shaft through a computer. The entire bioreactor is fit into an incubator. The media is circulated between the bioreactor and two media reservoirs that are pumped with filtered 5% $CO_2$ in air. The cyclic compression is conducted for 8 hrs per day. After 4 weeks of culture, the cartilage graft is ready to be transplanted. The cell morphology, viability, extracellular matrix synthesis are analyzed.

Example 24

Recellularization of Costal Cartilage Disc In Vitro with Chondrocytes, Cultured Under Fluid Pressure Autologous chondrocytes isolated from recipient's non-load bearing femoral condyle or from a allogeneic source were propagated in vitro in culture media that was composed of Dulbecco's Modified Essential Medium (DMEM) supplemented with 10% FBS, non-essential amino acid, 40 µg/ml proline, and antibiotics (100 U/ml penicillin and 100 µg/ml streptomycin, Invitrogen) for between 3-5 passages. A devitalized costal cartilage disc stored in a vacuum sealed bag was retrieved and rinsed with isotonic saline. Cultured autologous chondrocytes were trypsinized from the culture flask and suspended in culture media supplemented with 50 µg/ml ascorbate at a density of $10 \times 10^6$ cell/ml. The devitalized cartilage disc was mixed with 1.5 ml of cell suspension in a 2 ml tube on a thermal mixer at 37° C. for about 1 hour. Then, the cartilage disc was transferred into a confining ring that had a porous platen made of cancellous bone at the bottom and was on top of another porous platen as illustrated in FIG. 24. On top of the disc, a second porous platen made of porous titanium was added. The cartilage disc was compressed by inducing compression on the culture media by a piston in a media reservoir (221), which induced pressure on the cartilage graft in a bioreactor filled with the culture media as illustrated in FIG. 24. The piston was driven by a computer controlled cam. The pressure was cycled between 0-2 MPa. The pressure induced compression was applied for 8 hrs per day. The entire bioreactor assembly was fit into an incubator. After 14 days of culture, the top porous platen was removed. The cartilage disc along with the bottom porous platen formed a coherent cartilage graft and was ready to be transplanted. The cell morphology, viability, extracellular matrix synthesis were analyzed.

Example 25

Recellularization of Hyaline Cartilage Slices In Vitro with Allogeneic Stromal Cells from Synovium with Fluid Pressure Allogeneic stromal cells from synovium, as illustrated in Example 19, were suspended in chondrogenic media, which was composed of DMEM (Invitrogen), 10% serum, 10 ng/ml TGF-β1, 1% ITS (10 µg/ml insulin, 5.5 µg/ml transferrin, 5 ng/ml selenium, 0.5 mg/ml BSA, 4.7 µg/ml linoleic acid; Sigma), 50 µg/ml ascorbate-2-phosphate, 40 µg/ml proline, 100 µg/ml pyruvate, and 100 U/ml penicillin and 100 µg/ml streptomycin. Devitalized human hyaline cartilage slices, stored in a vacuum sealed bag, were retrieved and rinsed with isotonic saline. Each individual slice of cartilage from the same package was placed in each well of a 24-well plate. Optionally, a cloning cylinder with grease was placed on top of the cartilage slice to create a seal at the peripheral. Allogeneic stromal cells from synovium, suspended at $2 \times 10^6$ cells/ml, were seeded on top of the cartilage slice within the cloning cylinder. The whole plate was centrifuged at 400 g for 5 min to facilitate the cell attachment. Each individual cell-seeded slice was transferred into a confining ring that had a porous platen made of cancellous bone at the bottom and was on top of another porous platen as illustrated in FIG. 24. All the slices were stacked within the confining ring. On top of the stack, a second porous platen made of porous titanium was added. The cartilage slices were compressed by inducing compression on the culture media by a piston in a media reservoir (221), which induced pressure on the cartilage graft in a bioreactor filled with the culture media as illustrated in FIG. 24. The piston was driven by a computer controlled cam. The pressure was cycled between 0-6 MPa. The pressure induced compression was conducted for 8 hrs per day. The entire bioreactor assembly was fit into an incubator. After 14 days of culture, the top porous platen was removed. The cartilage slices along with the bottom porous platen formed a coherent cartilage graft and was ready to be transplanted. The cell morphology, viability, extracellular matrix synthesis were analyzed.

Example 26

Recellularization of Hyaline Cartilage Slices In Vitro with Allogeneic Stromal Cells from Bone Marrow to Create a Contour Using Air Pressure Human allogeneic bone marrow stromal cells (BMSCs) were isolated, cultured, expanded and used for recellularization. Frozen allogeneic whole bone marrow obtained from a commercial source was quickly thawed, washed, counted, and suspended in Dulbecco's modified Eagle medium (DMEM), 10% serum, 0.1 mM nonessential amino acids, antibiotics (100 U/ml penicillin and 100 µg/ml streptomycin, Invitrogen) and 1 ng/mL basic fibroblast growth factor (bFGF). The stromal cells were cultured in T-75 flask with cell density of $10^3$/ml for 3 hrs to allow adherent cells to attach. Then the non-adherent cells were washed out with DMEM. The adherent cells were cultured until near confluence. Passage 3 BMSCs were trypsinized and suspended in chondrogenic media, which was composed of DMEM (Invitrogen), 10% serum, 10 ng/ml TGF-β1, 1% ITS (10 µg/ml insulin, 5.5 µg/ml transferrin, 5 ng/ml selenium, 0.5 mg/ml BSA, 4.7 µg/ml linoleic acid; Sigma), 50 µg/ml ascorbate-2-phosphate, 40 µg/ml proline, 100 µg/ml pyruvate, and 100 U/ml penicillin and 100 µg/ml streptomycin.

Devitalized human hyaline cartilage slices, without subchondral bone attached and stored in a vacuum sealed bag, were retrieved and rinsed with isotonic saline. Each individual slice of cartilage, from the same package, was placed in each well of the 24-well plate. Optionally, a cloning cylinder with grease was place on top of the cartilage slice to create a seal at the peripheral. Passage 3 BMSCs, suspended at $2 \times 10^6$ cells/ml, were seeded on top of the cartilage slice within the cloning cylinder. The whole plate was centrifuged at 400 g for 5 min to facilitate cell attachment. The BMSC seeded slices were further culture in a 24-well plate for another 24 hours. Each individual cell-seeded slice was then transferred into a confining ring that had a convex porous platen made of cancellous bone at the bottom and was on top of another porous platen as illustrated in FIG. 23. All the slices were stacked within the confining ring. On top of the stack, a second convex porous platen made of porous titanium was added. The stacked cartilage slices were compressed by inducing compressive air towards two flexible membranes (172 and 193) that induce pressure on the cartilage graft a bioreactor filled with the culture media (same as above) as illustrated in FIG. 23. The pressure was cycled between 0-2 MPa and induced by the filtered 5% $CO_2$ in air driven by the piston and a computer controlled cam. The pressure induced compression was conducted for 8 hrs per day. The entire bioreactor assembly was fit into an incubator. After 14 days of culture, the top convex porous platen was removed. The stack of cartilage slices along with the bottom porous platen formed a coherent cartilage graft and was ready to be transplanted. The cell morphology, viability, extracellular matrix synthesis were analyzed.

Example 27

Recellularization of Costal Cartilage Slices and Bone Plug (to Form Composite Graft) In Vitro with Allogeneic Stromal Cells from Synovium, No Combine Culture Cartilage slices isolated from cadaver costal cartilage, are disinfected, cleaned, devitalized, and recellularized with allogeneic stromal cells from synovium and cultured under mechanical stimuli as illustrated in Example 25 to form a coherent stack of cartilage slices. Parallel to the cartilage slice culture, a hollow cylindrical bone plug (with same outer diameter as the cartilage discs and a center hole in the middle), cleaned, disinfected, freeze dried and sterilized, is soaked in DMEM for 30 min. Allogeneic stromal cells from synovium, suspended at a density of $2 \times 10^6$ cells/ml, are mixed with the bone plug on a thermal mixer overnight at 37° C. On the second day, a highly porous calcium phosphate, obtained from a commercial source, is mixed with the stromal cell suspension. The mixture is inserted into the center of the hollow cylindrical plug. The entire bone plug is further cultured in a roller bottle or under mechanical compression similar to the compression of osteochondral plug as illustrated in Example 22 using osteogenic culture media. The media is composed of DMEM (Invitrogen), 10% serum, 100 nM dexamethasone, 10 mM β-glycerophosphate, 50 µg/ml ascorbate-2-phosphate (Sigma), and antibiotics (100 U/ml penicillin and 100 µg/ml streptomycin, Invitrogen). After 4 weeks of parallel culture of cartilage discs and the bone plug, the grafts are retrieved from corresponding bioreactors and are ready for transplantation. The cell morphology, viability, extracellular matrix synthesis are analyzed.

Example 28

Recellularization of Menisci Cartilage Slices and Bone Plug (to Form Composite Graft) In Vitro with Allogeneic Stromal Cells from Synovium, Combine Cultured Under Loading with Loading Shaft Cartilage slices isolated from cadaver menisci, are disinfected, cleaned, devitalized, and recellularized with allogeneic stromal cells from synovium and cultured under mechanical stimuli as illustrated in Example 25 to form a coherent stack of cartilage slices. Parallel to the cartilage slice culture, a hollow cylindrical bone plug (with same outer diameter as the cartilage discs and a center hole in the middle), cleaned, disinfected, freeze dried and sterilized, is soaked in DMEM for 30 minutes. Allogeneic stromal cells from bone marrow, suspended at a density of $2\times10^6$ cells/ml, are mixed with the bone plug on a thermal mixer over night at 37° C. On the second day, demineralized bone matrix, from the same donor as the bone plug, is mixed with the stromal cell suspension and the mixture is inserted into the center of the hollow cylindrical bone plug. The entire bone plug is further cultured in a roller bottle or under mechanical compression similar to the compression of osteochondral plug as illustrated in Example 22 using osteogenic culture media. The media is composed of DMEM (Invitrogen), 10% serum, 100 nM dexamethasone, 10 mM β-glycerophosphate, 50 µg/ml ascorbate-2-phosphate (Sigma), and antibiotics (100 U/ml penicillin and 100 µg/ml streptomycin, Invitrogen). After 1 weeks of parallel culture of cartilage discs and the bone plug, the grafts are retrieved from corresponding bioreactors and transferred into another bioreactor as illustrated in FIG. 28. The bone plug is supported by the supporting ring (248). The stack of cartilage slices are placed within a confining ring (204) and sandwiched between a top porous platens (226) made of porous titanium and the bone plug. The cartilage slices are placed within the top well, while the bone plug is placed in the bottom well of the bioreactor. The culture media in the top well of the bioreactor is chondrogenic media, which is composed of DMEM (Invitrogen), 10% serum, 10 ng/ml TGF-β1, 1% ITS (10 µg/ml insulin, 5.5 µg/ml transferrin, 5 ng/ml selenium, 0.5 mg/ml BSA, 4.7 µg/ml linoleic acid; Sigma), 50 µg/ml ascorbate-2-phosphate, 40 µg/ml proline, 100 µg/ml pyruvate, and 100 U/ml penicillin and 100 µg/ml streptomycin. The culture media in the bottom well of the bioreactor is osteogenic, which is composed of DMEM (Invitrogen), 10% serum, 100 nM dexamethasone, 10 mM β-glycerophosphate, 50 µg/ml ascorbate-2-phosphate (Sigma), and antibiotics (100 U/ml penicillin and 100 µg/ml streptomycin, Invitrogen). The compressive stress is cycled between 0-6 MPa that is controlled by the load cell and the movement of the loading shaft through a computer. The entire bioreactor is fit into an incubator. The media is circulated between the bioreactor and two media reservoirs that are pumped with filtered 5% $CO_2$ in air. The cyclic compression is applied for 8 hrs per day. After 3 weeks of culture, a composite graft is obtained and ready to be transplanted. The cell morphology, viability, extracellular matrix synthesis are analyzed.

Example 29

Implant Osteochondral Plug

A devitalized rabbit osteochondral plug, recellularized in vivo as illustrated in Example 20, is used for implantation. The osteochondral plug is step cylindrical and has one slot as shown in plug (35) in FIG. 4. Both knee joints of a New Zealand white rabbit are exposed through a medial parapatellar longitudinal incision. The capsule is incised, and the medial femoral condyle exposed. With the knee maximally flexed, a full-thickness bore, 3 mm in diameter and 3 mm in depth, is created in the center of the condyle using a drill with 3 mm outside diameter. A stop is mounted on the drill bit to insure the 3 mm depth of the bore. All debris is removed from the defect with a curette and the edge carefully cleaned with a scalpel blade. The tissue removed from the coring is further crushed and used for later implantation. A bore is created on the opposing leg and remained untreated to serve as a control. The bore on the treated side is filled with 24 mM N-(2'-ethylaminoethyl)-4-amino-1,8-naphthalimide in gelatin solution supplemented with 5 µM lycopene (Sigma) for 10 minutes to stain the cartilage tissue. Meanwhile, the circumferential area of the cartilage cap of the osteochondral plug is treated with the same N-(2'-ethylaminoethyl)-4-amino-1,8-naphthalimide solution. The crushed tissue removed from the coring is inserted into the slot on the osteochondral plug inserted. After finishing staining with the photoactive dye, the bore in the bone portion is rinsed with isotonic saline.

Next, part of the crushed tissue is inserted back into the bore in the recipient joint to fill the gap between the bore and the bone portion of the step cylinder. The osteochondral plug is transferred to the blind bore and pushed slight until interference with the surrounding cartilage tissue. A needle connected to an insertion device is inserted through the cartilage cap. A vacuum device is engaged to remove the air/gas and fluid trapped within the bore and forced the osteochondral plug into the blind bore. After the graft is properly inserted for 2-10 minutes, the photoactivated dye is activated by a laser with 457 nm wave length as illustrated in FIG. 34. A 2.5 mm disc is placed at the center of the cartilage graft to protect it from the laser beam. The laser beam is delivered through an optical fiber with a spot size of 4 mm and an intensity of ~2 $W/cm^2$. The exposure time is about 240 seconds. Then, both knee joints are closed. The graft remains in place for 4 weeks and is analyzed.

Example 30

Implant Cartilage Disc from Menisci

A devitalized rabbit cartilage disc, isolated from menisci, is crafted to star-shaped right before implantation and recellularized in situ as in Example 17. Both knee joints of a New Zealand white rabbit are exposed through a medial parapatellar longitudinal incision. The capsule is incised, and the medial femoral condyle exposed. With the knee maximally flexed, a first full-thickness bore, 3 mm in diameter and 3 mm in depth, is created in the center of the condyle using a drill with 3 mm outside diameter. A stop is mounted on the drill bit to insure the 3 mm depth of the bore. Then a star-shaped second bore is created only at the cartilage portion of the first bore, using a custom designed coring device as illustrated in FIG. 31a. All debris is removed from the defect with a curette and the edge is carefully cleaned with a scalpel blade. A bore is created on the opposing leg and remained untreated to serve as a control. The bore on the treated side is filled with 0.1% Rose Bengal in phosphate buffered saline (PBS) and supplemented with 5 µM lycopene (Sigma) for 5 minutes to stain the cartilage tissue. Meanwhile, the circumferential area of the cartilage disc is treated with the same Rose Bengal solution. After staining with the photoactive dye, the first bore in the bone portion is rinsed with isotonic saline.

Bone filler is made by mixing the freeze dried demineralized bone matrix with the wet homogenized fascia at 1:1 ratio (by weight). Bone filler is packed into the bone portion of the first bore that is created at the defect site to provide support for the cartilage. The cartilage disc is transferred to the blind bore, fit into the star-shaped bore, and pushed slightly until interference with the surrounding cartilage tissue. Next, a needle connected to an insertion device is inserted through the cartilage disc. A vacuum device is engaged to remove the air/gas and fluid trapped within the blind bore and forces the cartilage disc into the blind bore.

After the graft is properly inserted for 2 minutes, the photoactivated dye is activated by a laser as illustrated in FIG. 34 with 564 nm wave length. A 2.5 mm disc is placed at the center of the cartilage graft to protect it from the laser beam. The laser beam is delivered through an optical fiber with a spot size of 5 mm with intensity of ~1 W/cm$^2$. The exposure time is about 250 seconds. Then, both knee joints are closed. The graft is remained in place for 4 weeks and is analyzed.

Example 31

Implant Hyaline Cartilage Slices

Both knee joints of a New Zealand white rabbit are exposed through a medial parapatellar longitudinal incision. The capsule is incised, and the medial femoral condyle exposed. With the knee maximally flexed, a partial-thickness bore, 3 mm in diameter and broke the tide mark in depth, is created in the center of the condyle using a drill with 3 mm outside diameter. A stop is mounted on the drill bit to insure the depth of the bore is slightly deeper than the cartilage tissue depth (~1 mm). All debris is removed from the defect with a curette and the edge carefully cleaned with a scalpel blade. A bore is created on the opposing leg and remained untreated to serve as a control. Devitalized rabbit cartilage slices, of 250 µm thickness, are seeded with allogeneic stromal cells in situ as illustrated in Example 19, and punched to 3 mm diameter. The bore on the treated side is filled with 0.1% riboflavin (10 mg riboflavin 5-phosphate in 10 ml 20% dextran-T-500) supplemented with 5 µM lycopene (Sigma) for 5 minutes to stain the cartilage tissue. Meanwhile, the circumferential area of each of the cartilage slices is treated with the same riboflavin solution. After staining with the photoactive dye, riboflavin is removed from the bore. Each individual cartilage slice is transferred, pushed into the bore against the subchondral bone, and the slices are stacked together until reach the same height as the surrounding tissue. The cartilage slices are boned between adjacent slices using a bonding agent made of MATRI-GEL® and genipin. After the graft is properly inserted, the photoactivated dye is activated by two ultraviolet A diodes as illustrated in FIG. 34 with 370 nm wave length. A 2.5 mm disc is placed at the center of the cartilage graft to protect it from the light beam. The light beam is delivered through an optical fiber with a spot size of 4 mm and intensity of about 3 mW/cm$^2$. The exposure time is about 30 minutes. Then, both knee joints are closed. The graft are remained in place for 4 weeks and analyzed.

Example 32

Implant Cartilage Slices with Bone Plug and Calcium Phosphate Composite Cylinder Both knee joints of a New Zealand white rabbit are exposed through a medial parapatellar longitudinal incision. The capsule is incised, and the medial femoral condyle exposed. With the knee maximally flexed, a full-thickness bore, 3 mm in diameter and 3 mm in depth is created in the center of the condyle using a drill with 3 mm outside diameter. A stop is mounted on the drill bit to insure the 3 mm depth of the bore. All debris is removed from the defect with a curette and the edge carefully cleaned with a scalpel blade. A bore is created on the opposing leg and remained untreated to serve as a control. Devitalized rabbit cartilage slices, of 250 µm thickness, are seeded with allogeneic stromal cells, stacked and cultured to form a viable coherent cartilage graft as illustrated in Example 25, and punched to 3 mm diameter. A bone plug filled with porous tri-calcium phosphate and cultured as illustrated in Example 27 is trimmed to the length of the bone portion of the bore at the defect site. The bore on the treated side is filled with 0.1% riboflavin (10 mg riboflavin 5-phosphate in 10 ml 20% dextran-T-500) supplemented with 5 µm lycopene (Sigma) and 5% genipin for 5 minutes to stain the cartilage tissue. Meanwhile, the circumferential area of each of the cartilage slices is treated with the same riboflavin and genipin solution.

After finishing staining with the photoactive dye and crosslinking agent, riboflavin and genipin solution is removed from the bore. The bone plug is inserted into the bore first. Then the stack of cartilage slices is transferred to the bore, fit into the bore, and pushed slight until reaching the same height as the surrounding tissue. Then, the photoactivated dye is activated by two ultraviolet A diodes as illustrated in FIG. 34 with 370 nm wave length. A 2.5 mm disc is placed at the center of the cartilage graft to protect it from the light beam. The light beam is delivered through an optical fiber with a spot size of 4 mm with intensity of about 3 mW/cm$^2$. The exposure time is 30 minutes. Then, both knee joints are closed. The graft is remained in place for 4 weeks and analyzed.

Example 33

Implant Cartilage Curls with a Cartilage Disc

Both knee joints of a New Zealand white rabbit are exposed through a medial parapatellar longitudinal incision. The capsule is incised, and the medial femoral condyle exposed. With the knee maximally flexed, a full-thickness bore, 3 mm in diameter and 3 mm in depth, is created in the center of the condyle using a drill with 3 mm outside diameter. A stop is mounted on the drill bit to insure the 3 mm depth of the bore. All debris is removed from the defect with a curette and the edge carefully cleaned with a scalpel blade. A bore is created on the opposing leg and remained untreated to serve as a control. The bore on the treated side is filled with 0.1% Rose Bengal in collagen solution supplemented with 5 µM lycopene (Sigma Aldrich) for 5 minutes to stain the cartilage tissue. Meanwhile, the circumferential area of the rabbit cartilage disc is treated with the same Rose Bengal solution. After finishing staining with the photoactive dye, the bore in the bone portion is rinsed with isotonic saline.

Next, devitalized rabbit cartilage curls are mixed with freeze dried rabbit demineralized bone matrix (v/v=1:1). Bone marrow withdraw from the same rabbit is used to hydrate the cartilage and DBM mixture. The hydrated cartilage and DBM mixture is packed into the bottom portion of the bore to about 2 mm in depth. The cartilage disc is transferred to the bore, fit into the bore, and pushed slightly until interference with the surrounding cartilage tissue. A needle connected to an insertion device is inserted through the cartilage disc. A vacuum device is engaged to remove the air/gas and fluid trapped within the blind bore and forces the cartilage disc into the blind bore.

After the graft is properly inserted, the photoactive dye is activated by a laser as illustrated in FIG. 34 with 564 nm wave length. A 2.5 mm diameter non-light penetrable disc is placed at the center of the cartilage graft to protect it from the laser beam. The laser beam is delivered through an optical fiber with a spot size of 5 mm with intensity of ~1 W $cm^2$. The exposure time is about 250 seconds. Then, both knee joints are closed. The graft remains in place for 4 weeks and is the analyzed.

What is claimed:

1. A process for implanting a cartilage graft into a cartilage defect having a size, contour, and location and being surrounded by a cartilage surface, and sealing the implanted cartilage graft with recipient tissue, comprising
   a. creating a cylindrical bore down to a bone portion of the cartilage defect;
   b. selecting a cylindrical osteochondral plug that matches the size, contour, and location of the defect site, said osteochondral plug comprising a cartilage cap having a circumferential area and a superficial surface;
   c. treating the bore at said defect site with a first bonding agent;
   d. treating the circumferential area of said cartilage cap on said osteochondral plug with a second bonding agent; and
   e. inserting said osteochondral plug into said defect site and wherein the superficial surface of said cartilage cap is surrounded by the cartilage surface surrounding the defect site,
   wherein said first and second bonding agents are activated by applying a stimulation agent that induces sealing, integration, and hydrodynamic restoration of the recipient tissue, and
      wherein said first and second bonding agent are independently one or more photoactive dyes selected from the group consisting of bis-diazopyruvamide-N,N9-bis(3-diazopyruvoyl)-2,29-(ethylenedioxy)bis-(ethylamine) (DPD), diazopyruvoyl (DAP), phloxime, thionine, acridine orange, ethyl eosin, eosin Y, and combinations thereof.

2. The process according to claim 1, wherein said stimulation agent is an energy source.

3. The process according to claim 1, wherein the cartilage cap has a gap, bore, channel, or slot on a side opposite the superficial surface and a cartilage filler is inserted into the gap, bore, channel, or slot in said cartilage cap from the bottom of said osteochondral plug, wherein the superficial surface of the cartilage cap is closed.

4. The process according to claim 1, wherein said first or second bonding agent comprises enzymes, bioactive growth supplements, natural polymers, synthetic polymers, photoactive agents, antioxidants, crosslinking agents, vital cells, or any combination thereof.

5. The process according to claim 1, wherein said first or second bonding agent comprises a solution, gel, putty, tape, or sponge.

6. The process according to claim 1, wherein the cartilage graft is cleaned, disinfected, devitalized, and stored.

7. The process according to claim 1, wherein the cartilage graft is cleaned, disinfected, devitalized, recellularized in vitro, and stored.

8. The process according to claim 1, wherein the cartilage graft is cleaned, disinfected, devitalized, stored, and recellularized, wherein said recellularization occurs in vitro, in situ, or in vivo.

9. The process according to claim 1, wherein the cartilage graft is contoured to match the contour of a defect site.

10. The process according to claim 1, wherein said osteochondral plug is inserted into said defect using an insertion device.

11. The process according to claim 1, wherein the first bonding agent and the second bonding agent are crosslinked.

12. The process according to claim 1, wherein the cartilage cap has a gap, bore, channel, or slot on a side opposite the superficial surface and a bone filler is inserted into the gap, bore, channel, or slot in said bone portion from the bottom of said osteochondral plug, wherein the superficial surface of the cartilage cap is closed.

13. A process for implanting a cartilage graft into a cartilage defect having a size, contour, and location and being surrounded by a cartilage surface, and sealing the implanted cartilage graft with recipient tissue, comprising
    a. creating a cylindrical bore down to a bone portion of the cartilage defect;
    b. selecting a cylindrical osteochondral plug that matches the size, contour, and location of the defect site, said osteochondral plug comprising a cartilage cap having a circumferential area and a superficial surface;
    c. treating the bore at said defect site with a first bonding agent;
    d. treating the circumferential area of said cartilage cap on said osteochondral plug with a second bonding agent; and
    e. inserting said osteochondral plug into said defect site and wherein the superficial surface of said cartilage cap is surrounded by the cartilage surface surrounding the defect site,
    wherein said first and second bonding agents are activated by applying a stimulation agent that induces sealing, integration, and hydrodynamic restoration of the recipient tissue, and
    wherein said first and second bonding agent comprise a tethered diazopyruvate composition.

14. The process according to claim 13, wherein said stimulation agent is an energy source.

15. The process according to claim 13, wherein the cartilage cap has a gap, bore, channel, or slot on a side opposite the superficial surface and a cartilage filler is inserted into the gap, bore, channel, or slot in said cartilage cap from the bottom of said osteochondral plug, wherein the superficial surface of the cartilage cap is closed.

16. The process according to claim 13, wherein said first or second bonding agent further comprises enzymes, bioactive growth supplements, natural polymers, synthetic polymers, photoactive agents, antioxidants, crosslinking agents, vital cells, or any combination thereof.

17. The process according to claim 13, wherein said first or second bonding agent further comprises a solution, gel, putty, tape, or sponge.

18. The process according to claim 13, wherein the cartilage graft is cleaned, disinfected, devitalized, and stored.

19. The process according to claim 13, wherein the cartilage graft is cleaned, disinfected, devitalized, recellularized in vitro, and stored.

20. The process according to claim 13, wherein the cartilage graft is cleaned, disinfected, devitalized, stored, and recellularized, wherein said recellularization occurs in vitro, in situ, or in vivo.

21. The process according to claim 13, wherein the cartilage graft is contoured to match the contour of a defect site.

22. The process according to claim 13, wherein said osteochondral plug is inserted into said defect using an insertion device.

23. The process according to claim 13, wherein the first bonding agent and the second bonding agent are crosslinked.

24. The process according to claim 13, wherein the cartilage cap has a gap, bore, channel, or slot on a side opposite the superficial surface and a bone filler is inserted into the gap, bore, channel, or slot in said bone portion from the bottom of said osteochondral plug, wherein the superficial surface of the cartilage cap is closed.

* * * * *